(12) United States Patent
Miyata et al.

(10) Patent No.: US 7,645,882 B2
(45) Date of Patent: Jan. 12, 2010

(54) INHIBITOR OF PROTEIN MODIFICATION PRODUCTS FORMATION

(76) Inventors: Toshio Miyata, 102-Ekuseru Isehara, 16-25, Sakuradai 2-chome, Isehara-shi, Kanagawa 259-1132 (JP); Kiyoshi Kurokawa, Ichigayahills 401, 49, Ichigayayanagi-cho, Sinjyuku-ku, Tokyo 162-0061 (JP)

( * ) Notice: Subject to any disclaimer, the term of this patent is extended or adjusted under 35 U.S.C. 154(b) by 221 days.

(21) Appl. No.: 10/581,255

(22) PCT Filed: Dec. 3, 2004

(86) PCT No.: PCT/JP2004/018038

§ 371 (c)(1),
(2), (4) Date: Jul. 10, 2006

(87) PCT Pub. No.: WO2005/054205

PCT Pub. Date: Jun. 16, 2005

(65) Prior Publication Data
US 2007/0123577 A1    May 31, 2007

(30) Foreign Application Priority Data
Dec. 5, 2003  (JP) .............................. 2003-407834

(51) Int. Cl.
*C07D 271/00*  (2006.01)
*C07D 285/02*  (2006.01)
*C07D 285/04*  (2006.01)

(52) U.S. Cl. .................................................. 548/125
(58) Field of Classification Search ....................... None
See application file for complete search history.

(56) References Cited

FOREIGN PATENT DOCUMENTS

WO        00/10606        3/2000

OTHER PUBLICATIONS

Yanagisawa et. al., Cardioprotective effect of MCI-186 during acute ischemia-reperfusion injury in rats, International Journal of Angiology,1994, 3:12-15.*
Kleinpeter et. al., Journal of Physical Organic Chemistry, 2001, 14:566-576.*
Dorwald F. A. (Side reactions in organic synthesis, 2005, Wiley, VCH, Weinheim, p. IX of Preface).*
Maillard, L. C.et al., "Compt. Rend. Soc. Biol.", 1912, vol. 72, p. 599.
Miyata, T.et al., "Kidney Int.", 1999, vol. 55, p. 389-399.
Esterbauer, H.et al., "Free Radic. Biol Med.", 1991, vol. 11, p. 81-128.
Anderson, M. M.et al., "J Clin. Invest.", 1997, vol. 99(3), p. 424-432.
Sell, D. R.et al., "J. Biol. Chem." 1989, vol. 264(36), p. 21597-21602.
Nakamura, K.et al., "J. Chem. Soc. Chem. Commun.", 1992, vol. 15, p. 992-994.
Hayase, F.et al., "Biosci. Biotech. Biochem.", 1994, vol. 58(10), p. 1936-1937.
Njoroge, F. G.et al., "Carbohyd. Res.", 1987, vol. 167, p. 211-220.
Ahmed, M. U.et al., "J. Biol. Chem.", 1986, vol. 261(11), p. 4889-4894.
Hayase, F.et al., "Biosci. Biotech. Biochem.", 1995, vol. 59(8), p. 1407-1411.
Ahmed, M. U.et al., "Biochem. J.", 1997, vol. 324, p. 565-570.
Brinkmann, E.et al., "J. Chem. Soc. Perkin. Trans. 1", 1995, p. 2817-2818.
Wells-Knecht, K. J.et al., "J. Org. Chem.", 1995, vol. 60, p. 6246-6247.
Nagaraj, R. H.et al., "J. Biol. Chem.", 1996, vol. 271(32), p. 19338-19345.
Shipanova, I. N.et al., "Arch. Biochem. Biophys.", 1997, vol. 344(1), p. 29-36.
Neeper, M.et al., "J. Biol. Chem.", 1992, vol. 267(21), p. 14998-15004.
Suzuki, H.et al., "Nature", 1997, vol. 386, p. 292-296.
Vlassara, H.et al., "Molecular Medicine", 1995, vol. 1(6), p. 634-646.
Lander, H. M.et al., "J. Biol. Chem.", 1997, vol. 272(28), p. 17810-17814.
Chappey, O.et al., "Eur. J. Clin. Invest.", 1997, vol. 27, p. 97-108.
Yamagishi, S.et al., Biochem. Biophys. Res. Commun., 1995, vol. 213(2), p. 681-687.

(Continued)

*Primary Examiner*—Frederick Krass
*Assistant Examiner*—Marcos Sznaidman
(74) *Attorney, Agent, or Firm*—Wenderoth, Lind & Ponack, L.L.P.

(57) ABSTRACT

To provide a inhibitor of protein modification products formation capable of inhibiting of vitamin B6 deficiency disease as a side effect, especially a renal protective agent.

There is provided a use, as an active ingredient, of any of free or salt-form compounds of either of the formulae: (I) (II) [wherein R1 is substituted or unsubstituted aromatic ring; and each of R2, R3 and R4 is a hydrogen atom or monovalent organic group, or alternatively R2 and R3 cooperate to form a condensed ring or R3 and R4 cooperate to represent a divalent organic group, provided that R3 and R4 are not simultaneously hydrogen atoms].

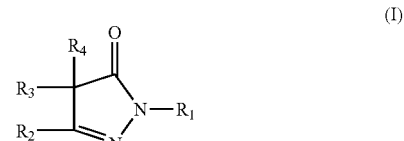

(I)

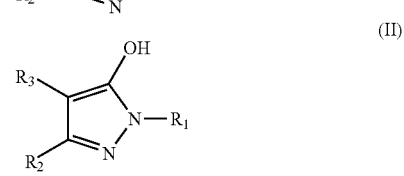

(II)

2 Claims, 19 Drawing Sheets

OTHER PUBLICATIONS

Yamagishi, S. et al., "FEBS Lett.", 1996, vol. 384, p. 103-106.
Doi, T. et al., "Proc. Natl. Acad. Sci. USA", 1992, vol. 89, p. 2873-2877.
Horie, K. et al., "J. Clin. Invest.", 1997, vol. 100(12), p. 2995-3004.
Sugimoto, K. et al., "Diabetologia", 1997, vol. 40, p. 1380-1387.
Park, L. et al., "Nat. Med.", 1998, vol. 4(9), p. 1025-1031.
Miyata, T. et al., "J. Clin. Invest.", 1993, vol. 92, p. 1243-1252.
Smith, M. A. et al., "Proc. Natl. Acad. Sci. USA", 1994, vol. 91, p. 5710-5714.
Miyata, T. et al., "Biochem. Biophys. Res. Commun.", 1998, vol. 244, p. 45-49.
Makita, Z. et al., "N. Engl. J. Med.", 1991, vol. 325(12), p. 836-842.
Bucala, R. et al., "J. Clin. Invest.", 1991, vol. 87, p. 432-438.
Vlassara, H. et al., "Proc. Natl. Acad. Sci. USA", 1994, vol. 91, p. 11704-11708.
Miyata, T. et al., "J. of Am. Soc. Nephrol.", 1996, vol. 7(8), p. 1198-1206.
Sugiyama, S. et al., "J. of Am. Soc. Nephrol.", 1998, vol. 9, p. 1681-1688.
Witko-Sarsat, V. et al., "Kidney Int.", 1996, vol. 49, p. 1304-1313.
Canestrari, F. et al., "Acta Haematol.", 1994, vol. 91, p. 187-193.
Ueda, Y. et al., "Biochem., Biophys. Res. Commun.", 1998, vol. 245, 785-790.
Richard, M. J. et al., "Nephron", 1991, vol. 57, p. 10-15.
Jadoul, M. et al., "Kidney Int.", 1999, vol. 55, p. 2487-2492.
Miyata, T. et al., "Kidney Int.", 1997, vol. 51, p. 1170-1181.
Ulbricht, R. J. et al., "Fund Appl. Toxic.", 1984, vol. 4, p. 843-853.
Miyata, T. et al., "Kidney Int.", 2000, vol. 58, p. 425-435.
Yamada, K. et al., "Clin. Nephrol.", 1994, vol. 42(6), p. 354-361.
Miyata, T. et al., "Nephrol. Dial. Transplant.", 1997, vol. 12, p. 255-258.
Edelstein, D. et al., Diabetologia, 1992, vol. 35, p. 96-97.
Hammes, H.P. et al., "Proc. Natl. Acad. Sci. USA", 1991, vol. 88, p. 11555-11558.
Matsumoto, K. et al., "Biochem. Biophys. Res. Commun.", 1997 vol. 241(2), p. 352-354.
Nakamura, S. et al., "Diabetes", 1997, vol. 46, p. 895-899.
Beisswenger, P. J. et al., Diabetes, 1999, vol. 48, p. 198-202.
Thornalley, P. J. et al., "Endocrinol. Metab.", 1996, vol. 3, p. 149-166.

* cited by examiner

Stability of TM-2002 injectable lyophilized formulation

1. TM-2002 injectable lyophilized formulation-aqueous solution (1ml) diluted with saline (1.5 ml)

2. TM-2002 hydrochloride
   (material; prepared when used for TLC)

3. TM-2002 hydrochloride (material) aqueous solution

Figure 17
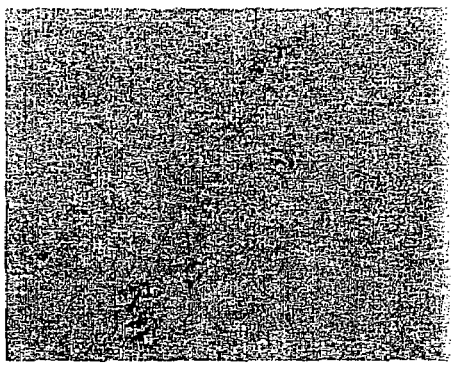
ORP 150 immunostaining in WKY drug free group
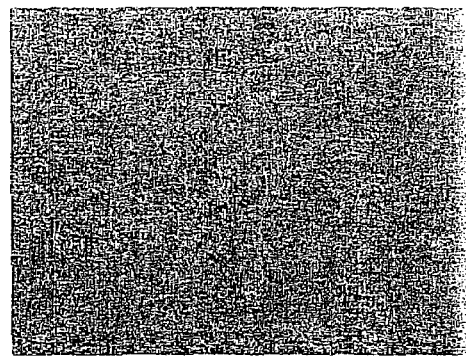
ORP 150 immunostaining in SHR drug free group
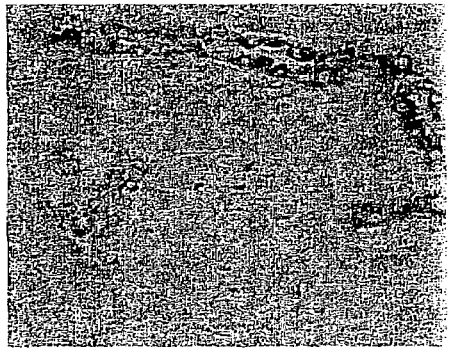
ORP 150 immunostaining in SHR/NDmcr-cp drug free group
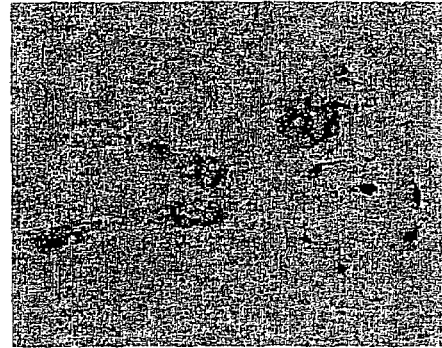
ORP 150 immunostaining in SHR/NDmcr-cp TM-2002 administered group

INHIBITOR OF PROTEIN MODIFICATION PRODUCTS FORMATION

TECHNICAL FIELD OF THE INVENTION

The present invention relates to a inhibitor of protein modification products formation, particularly to a medicament inhibiting the formation of protein modification products such as advanced glycation end products (AGEs) and advanced lipoxidation end products (ALEs), which are formed by the reaction with carbonyl compounds under non-enzymatic conditions.

BACKGROUND OF THE INVENTION

Glycation represents the chain reactions starting from the non-enzymatic reaction between the amino moiety on peptides or proteins and the carbonyl moiety on reducing sugars (Maillard reaction; cf. Reference 1) and are divided roughly into the initial stage and the later stage. The initial stage comprises a reversible reaction depending on the concentration of sugars and the reaction time wherein the amino moiety and the carbonyl moiety are non-enzymatically reacted to form Schiff bases, followed by Amadori rearrangement to form Amadori compounds.

In the later stage, the Amadori compounds formed in the initial stage are irreversibly subjected to dehydration, condensation, cyclization, oxidation, fragmentation, polymerization, rearrangement, etc. to give finally protein modification products called "AGEs". By auto-oxidation of sugars and the like, there are produced highly reactive dicarbonyl compounds such as 3-deoxiglucosone (hereinafter referred to as "3-DG"), glyoxal (hereinafter referred to as "GO") and methylglyoxal (hereinafter referred to as "MGO"), which may be further reacted with proteins to form AGEs modified at the lysine or arginine residues of the proteins in many cases.

Under the oxidation stress conditions, sugars, lipids, amino acids, etc. present abundantly in living bodies are oxidized to highly reactive carbonyl compounds. The thus produced GO, MGO, arabinose, glycol aldehyde, etc. are served as precursors of AGEs. Dehydroascorbic acid, which is formed by oxidation of ascorbic acid, is also served as a precursor of AGEs. These precursors have a carbonyl group, which is reacted non-enzymatically reacted with the amino moiety on proteins to give Schiff's bases and then form AGEs (cf. Reference 2).

Under the oxidation stress condition, lipoperoxidation also proceeds to form various carbonyl compounds such as malondialdehyde, hydroxynonenal and acrolein (cf. Reference 3). These carbonyl compounds react with the amino moiety or the like on proteins to form protein modification products called ALEs such as malondialdehyde-modified lysine and hydroxynonenal modifier (cf. Reference 2).

In addition, amino acids such as serine and threonine are oxidized to form carbonyl compounds such as acrolein and GO, followed by conversion into protein modification products (cf. Reference 4). A large number of carbonyl compounds are formed by the oxidative pathway, but some carbonyl compounds such as 3-DG are formed through the non-oxidative pathway.

As the known pathways for production of AGEs, there are (i) the pathway of conversion of Schiff's bases or Amadori compounds into AGEs through 3-DG, (ii) the pathway of oxidative conversion of Schiff's bases into glycolaldehyde alkylimines, followed by conversion of the latter into AGEs via aldoamines, (iii) the pathway conversion of aldoamines into AGEs via glyoxal monoalkylimines, (iv) the pathway of conversion of Amadori comounds into MGO through 2,3-enediol, followed by conversion of said MGO into AGEs, and (v) others.

It has recently been revealed that carboxymethyl-lysine as one of the AGEs is produced from GO, which is formed by lipoxidation of unsaturated fatty acids. It is thus considered that the glycation/oxidation reaction and the lipoxidation reaction occur on the common basis.

As understood from the above, carbonyl compounds produced through the oxidative or non-oxidative pathway from sugars, lipids, amino acids and ascorbic acid, modify proteins non-enzymatically and finally give protein modification products such as AGEs and ALEs. In particular, the increased state of the protein modification reaction by carbonyl compounds formed via a plurality of reaction pathways is called the protein modification due to excessive carbonyl, i.e. "carbonyl stress".

Known AGEs include pentosidine (cf. Reference 5), crossrine (cf. Reference 6), X1 (fluorolink), pyropyridine (cf. Reference 7), pyrarine (cf. Reference 8), carboxymethyl-lysine (cf. Reference 9), imidazolone compounds (cf. Reference 10), carboxyethyl-lysine (cf. Reference 11), MGO dimer (cf. Reference 12), GO dimer (cf. Reference 13), imidazolysine (cf. Reference 14), argupyrimidine (cf. Reference 15), etc.

AGEs receptors as heretofore cloned include RAGE (cf. Reference 16), macrophage scavenger receptor class A (cf. Reference 17), galectin 3 (cf. Reference 18), OST-48 and 80K-H (cf. Reference 17), etc.

It is reported that in the blood vessel tissue, RAGE (a cellular membrane penetration type protein belonging to the immunoglobulin superfamily) is bonded to AGEs, thereby active oxygen is generated in the cell to activate the p21ras/MAPK pathway (cf. Reference 19) so that the activation of the transcription factor NF-κB is induced to lead the expression of angiopathy associated factors such as VCAM-1 (cf. Reference 20). It is also reported that AGEs control the proliferation of endothelial cells in finer vessels via RAGE, control the proliferation of pericytes playing an important roll in homeostasis and produce a toxic effect (cf. Reference 21).

In addition, it is reported that AGEs act directly onto endothelial cells in finer vessels via RAGE to promote neoangiogenesis and inhibit the production of PG12 for thrombus tendency (cf. Reference 22). For further interests, enhancement of the substrate production in mesanginal cells, enhancement of the monocyte migration ability, release of inflammatory cytokines from macrophages, acceleration of the collagenase production in synovial cells, activation of osteoclasts, proliferation of vascular smooth muscle cells, acceleration of platelet aggregation, NO activity and its suppression of the smooth muscle relaxation are reported as the physiological activities of AGEs and ALEs (cf. Reference 23).

Diseases associated with AGEs include (i) nephropathy as a complication of diabetes (cf. Reference 24), nervous disorder (cf. Reference 25), retinopathy (cf. Reference 21) and cataract, (ii) arteriosclerosis (cf. Reference 26), (iii) dialysis amyloidosis as a complication of dialysis (cf. Reference 27) and peritoneal sclerosis in peritodialysis patients, (iv) Alzheimer's disease as a central neurological disease (cf. Reference 28), Pick's disease and Parkinson disease, (v) rheumatoid arthritis (cf. Reference 29), (vi) sunlight elastic fibrosis, (vii) aging, (viii) renal failure (cf. Reference 30), etc. In addition, it is reported that in case of diabetes, AGEs prevent the vasodilation derived from blood vessel endothelial cells (cf. Reference 31), and promote renal sclerosis (cf. Reference 32).

From the above, it is understood that protein modification products such as AGEs afford an adverse effect on living bodies directly or via receptors.

On the other hand, it is known that the blood concentration of AGEs are increased with the reduction of the renal function. The reduction of the renal function results in the accumulation of carbonyl compounds considered as having a molecular weight of not more than 5 kDa. In case of pentosidine or pyrarine, those can be present in a free form, but a large portion of them present in a binding form to serum albumin or the like (cf. Reference 33). In addition, it is reported that the blood level of pentosidine is strongly affected by the filtration function of glomeruli (cf. Reference 34).

In this way, a large portion of AGEs is eliminated from kidney, and their blood concentration is kept lower during good health. However, when the renal function is reduced, they act as a uremic toxin to produce a chronic bioactivities.

Dialysis therapy can remove AGEs in a free form but hardly remove those in a binding form to proteins or in an intramolecular bridging form (cf. Reference 35). Therefore, the accumulation of modified forms in living bodies is increased with the progression of renal failure. Further, in addition to the fundamental process where sugars are reacted in living bodies, AGEs in a free form supplied by diets as well as highly active intermediates such as 3-DG, GO and MGO formed from Amadori compounds and the like previously produced in living bodies react with proteins in succession to enhance the production of AGEs. Furthermore, the contact of blood to a dialysis membrane results, for instance, in activation of complements and leucocytes to enhance the generation of free radicals. Thus, dialysis therapy itself enhances oxidation and makes one of the causes for production of AGEs.

Accordingly, it is important in dialysis therapy to remove free form substances at an early stage of dialysis and suppress the generation of AGEs in a binding form as much as possible. Since it is difficult to remove AGEs in a binding form by dialysis therapy as stated above, development of a medicament which suppresses formation of protein modification products is highly desired for dialysis therapy.

Further, it is believed that not only reduction of renal function but also fall of anti-oxidation protective mechanism associated with renal failure is concerned with accumulation of protein modification products. In patients with renal failure, unbalance of such anti-oxidation abilities is suggested (cf. Reference 40) as the increase of oxidized glutathione against reducing glutathione in blood (cf. Reference 36), the reduction of activity of glutathione dependent enzymes, the decrease of preservation term renal failure plasma glutathione peroxidase (cf. Reference 37), the decrease of blood glutathione (cf. Reference 38) and the increase of activity of plasma superoxide dismutase against the decrease of selenium concentration in plasma (cf. Reference 39).

Furthermore, it is reported that in patients with chronic renal failure, remarkable amounts of highly reactive carbonyl compounds and AGEs are generally accumulated in blood and tissues regardless of hyperglycemia (cf. Reference 41). In renal failure, carbonyl compounds are placed under a state of high load (carbonyl stress) by non-enzymatic chemical reaction so that protein modification products are increased. This is considered to have been caused by modification of proteins with carbonyl compounds produced from sugars and lipids (cf. Reference 42).

Accordingly, suppression of the production of protein modification products caused by various factors may accomplish alleviation of tissue injury, and prevent or treat the conditions associated with protein modification products such as AGEs.

Dialysis for patients with chronic renal failure includes hemodialysis and peritoneal dialysis. In case of peritoneal dialysis, debris in blood is excreted into peritoneal dialysate through a peritoneal membrane. Peritoneal dialysate of high osmotic pressure, which contains glucose, icodextrin, amino acid or the like, is effective in collecting such highly reactive carbonyl compounds accumulated in blood of patients with renal failure as carbonyl compounds derived from carbohydrates (e.g. arabinose, GO, MGO, 3-DG), carbonyl compounds derived from ascorbic acid (e.g. dehydroascorbic acid) and carbonyl compounds derived from lipids (e.g. hydroxynonenal, malondialdehyde, acrolein) through a peritoneal membrane therein.

Further, it is known that highly reactive carbonyl compounds (e.g. 3-DG, 5-hydroxymethylfurfural, formaldehyde, acetaldehyde, GO, MGO, levulinic acid, furfural, arabinose) are formed in a peritoneal dialysate during the sterilization or storage of the peritoneal dialysate (cf. Reference 43).

Therefore, the concentration of carbonyl compounds in the peritoneal dialysate increases, and formation of protein modification enhances. As the result, the function of the peritoneal membrane is reduced, and thereby reduction of the water removing ability and progression to peritoneal sclerosis would be caused (cf. Reference 44).

In fact, it is demonstrated by the immunohistological study of endothelium and mesothelium that in patients with peritoneal dialysis, introduced glucose makes a carbonyl stress condition in the peritoneal cavity (cf. Reference 45).

In this way, it is presumed that in patients with dialysis, production of protein modification products by carbonyl compounds causes the morphological alteration of peritoneum and the reduction of the function (i.e. water removal function) resulting therefrom.

Taking into consideration the above facts and various morbid conditions such as renal failure in combination, it is believed that the accumulation of carbonyl compounds is one of the causes for enhancement of the AGEs production (cf. Reference 46). Thus, suppression of the AGEs production is considered as an effective measure for treatment of the conditions associated with AGEs.

A typical example of AGEs production inhibitors is aminoguanidine, which is considered to inhibit AGEs production by reaction with dicarbonyl compounds such as 3-DG generated from glucose, Schiff's bases or Amadori compounds to form thiazolines. Analysis using diabetes animal models confirmed that said compound is effective in delaying the progression of diabetic nephropathy (cf. Reference 47), retinopathy (cf. Reference 48) and cataract (cf. Reference 49).

Other examples are pyridoxamine derivatives (e.g. pyridorine). In case of OPB-9195 (i.e. ($\pm$)2-isopropylidene-hydrazon-4-oxo-thiazolydin-5-yl-acetanilide), the nitrogen atom in the hydrazine moiety is reacted with a carbonyl group to form a stable structure. Thus, it captures a reactive carbonyl group in a free form or a binding form to protein (cf. Reference 50) and therefore can prevent the production of not only AGEs but also ALEs in vitro. Since biguanide compounds such as metformin or buformin can also capture carbonyl compounds (cf. Reference 51), they have a possibility of being used as AGEs forming inhibitors. Further, the use of AGEs inhibitors capable of cleaving the bridge as a characteristic of AGEs and the enzymes capable of degrading Amadori compounds (i.e. amadoriase) are proposed.

Study is also made on the possibility of prevention of the AGEs and/or ALEs formation by removal of carbonyl compounds. For removal of carbonyl compounds, there are available several enzymes and enzymatic pathways, of which examples are aldol reducing enzymes and aldehyde dehydrogenase and glyoxalase pathway (cf. Reference 52). Redox co-enzymes such as reducing glutathione (GSH) and NAD(P)H are important factors for activation of those pathways.

Lowering of these removing pathways leads to increasing of numerous carbonyl compounds at the same time. Carbonyl compounds such as MGO and GO react with the thiol group of GSH and, as the result, they are metabolized with an enzyme, i.e. glyoxalase. NAD(P)H activates the glutathione reducing enzyme and enhances the GSH level. Namely, it is believed that the removal system of carbonyl compounds is inhibited by lowering of GSH or NAD(P)H due to unbalance of the intracellular redox mechanism, which leads to accumulation of AGEs and ALEs. In case of diabetes, it is suggested that the polyol pathway is activated by hyperglycemia, NAD(P)H and GSH are reduced and the removal system of carbonyl compounds is lowered.

If reduction in the concentration of thiols such as GSH and NAD(P)H lowers the removal of carbonyl compounds, and thereby causes the production of AGEs or ALEs as stated above, there is a possibility that carbonyl compounds would be decreased by increasing the thiol level. For this purpose, the supplementation of thiol groups with GSH, cysteine, acetylcysteine, etc., the lowering of the GSH demand with vitamin E, ubiquinol, etc. and the inhibition of the polyol system with aldose reducing enzyme inhibitors are proposed. Trapping of carbonyl compounds by the use of aminoguanidine, pyridoxamine, hydrazine, biguanide compounds or SH-containing compounds is also proposed (cf. Patent Reference 1).

As stated above in detail, the inhibitions of production of AGEs and ALEs are the way for prevention and treatment of diseases associated with them.

Patent Reference 1: WO 00/10606
Reference 1: Maillard, L. C. et al., "Compt. Rend. Soc. Biol.", (FR), 1912, Vol. 72, p 599
Reference 2: Miyata, T. et al., "Kidney Int.", (US), 1999, Vol. 55, p 389-399
Reference 3: Esterbauer, H. et al., "Free Radic. Biol. Med.", (US), 1991, Vol. 11, p 81-128
Reference 4: Anderson, M. M. et al., "J. Clin. Invest.", (US), 1997, Vol. 99, p 424-432
Reference 5: Sell, D. R. et al., "J. Biol. Chem.", (US), 1989, Vol. 264, p 21597-21602
Reference 6: Nakamura, K. et al., "J. Chem. Soc. Chem. Commun.", (GB), 1992, Vol. 15, p 992-994
Reference 7: Hayase, F. et al., "Biosci. Biotech. Biochem.", (JP), 1994, Vol. 58, p 1936-1937
Reference 8: Njoroge, F. G. et al., "Carbohyd. Res.", (NL), 1987, Vol. 167, p 211-220
Reference 9: Ahmed, M. U. et al., "J. Biol. Chem.", (US), 1986, Vol. 261, p 4889-4894
Reference 10: Hayase, F. et al., "Biosci. Biotech. Biochem.", (JP), 1995, Vol. 59, p 1407-1411
Reference 11: Ahmed, M. U. et al., "Biochem. J.", (GB), 1997, Vol. 324, p 565-570
Reference 12: Brinkmann, E. et al., "J. Chem. Soc. Perkin. Trans.", (GB), 1995, Vol. 2, p 1-2
Reference 13: Well-Knecht, K. J. et al., "J. Org. Chem.", (US) 1995, Vol. 60, p 6246-6247
Reference 14: Nagaraj, R. H. et al., "J. Biol. Chem.", (US), 1996, Vol. 271, p 19338-19345
Reference 15: Shipanova, I. N. et al., "Arch. Biochem. Biophys.", (US), 1997, Vol. 334, p 29-36
Reference 16: Neeper, M. et al., "J. Biol. Chem.", (US), 1992, Vol. 267, p 14998-15004
Reference 17: Suzuki, H.) et al., "Nature", (GB) 1997, Vol. 386, p 292-295
Reference 18: Vlassara, H et al., "Molecular Medicine", (US), 1995, Vol. 1, p 634-646
Reference 19: Lander, H. M. et al., "J. Biol. Chem.", (US), 1997, Vol. 272, p 17810-17814
Reference 20: Chappey, O. et al., "Eur. J. Clin. Invest.", (GB), 1997, Vol. 27, p 97-108
Reference 21: Yamagishi, S. et al., "Biochem. Biophys. Res. Commun., (US), 1995, Vol. 213, p 681-687
Reference 22: Yamagishi, S. et al., "FEBS Lett.", (NL), 1996, Vol. 384, p 103-106
Reference 23: Doi, T. et al., "Proc. Natl. Acad. Sci. USA)", (US), 1992, Vol. 89, p 2873-2877
Reference 24: Horie, K. et al., "J. Clin. Invest.", (US), 1997, Vol. 100, p 2995-3004
Reference 25: Sugimoto, K. et al., "Diabetologia", (DE), 1997, Vol. 40, p 1380-1387
Reference 26: Park, L. et al., "Nat. Med.", (US), 1998, Vol. 4, p 1025-1031
Reference 27: Miyata, T. et al., "J. Clin. Invest.", (US) 1993, Vol. 92, p 1243-1252
Reference 28: Smith, M. A. et al., "Proc. Natl. Acad. Sci. USA", (US), 1994, Vol. 91(12), p 5710-5714
Reference 29: Miyata, T. et al., "Biochem. Biophys. Res. Commun.", (US), 1999, Vol. 244, p 45-49
Reference 30: Makita, Z. et al., "N. Engl. J. Med.", (US), 1991, Vol. 325, p 836-842
Reference 31: Bucala, R. et al., "J. Clin. Invest.", (US), 1991, Vol. 87, p 432-438
Reference 32: Vlassara, H. et al., "Proc. Natl. Acad. Sci. USA", (US), 1994, Vol. 91, p 11704-11708
Reference 33: Miyata, T. et al., "J. Am. Soc. Nephrol.", (US), 1996, Vol. 7, p 1198-1206
Reference 34: Sugiyama, S. et al., "J. Am. Soc. Nephrol.", (US), 1998, Vol. 9, p 1681-1688
Reference 35: Miyata, T. et al., "Kidney Int.", (US), 1996, Vol. 49, p 1304-1313
Reference 36: Canestrari, F. et al., "Acta Haematol.", (CH), 1994, Vol. 91, p 187-193
Reference 37: Ueda, Y. et al., "Biochem. Biophys. Res. Commun.", (US), 1998, Vol. 245, p 785-790
Reference 38: Canestrari, F. et al., "Acta Haematol.", (CH), 1994, Vol. 91, p 187-193
Reference 39: Richard, M. J. et al., "Nephron", (CH), 1991, Vol. 57, p 10-15
Reference 40: Jadoul, M. et al., "Kidney Int.", (US), 1999, Vol. 55, p 2487-2492
Reference 41: Miyata, T. et al., "Kidney Int.", (US) 1997, Vol. 51, p 1170-1181
Reference 42: Miyata, T. et al., "Kidney Int.", (US), 1999, Vol. 55, p 389-399
Reference 43: Richard, J. U. et al., "Fund. Appl. Toxic.", (US), 1984, Vol. 4, p 843-853
Reference 44: Miyata, T. et al., "Kidney Int.", (US), 2000, Vol. 58, p 425-435
Reference 45: Yamada, K. et al., "Clin. Nephrol.", (DE), 1994, Vol. 42, p 354-361
Reference 46: Miyata, T. et al., "Nephrol. Dial. Transplant.", (GB), 1997, Vol. 12, p 255-258
Reference 47: Edelstein, D. et al., "Diabetologia, (DE), 1992, Vol. 35, p 96-101
Reference 48: Hammes, H. P. et al., "Proc. Natl. Acad. Sci. USA", (US), 1991, Vol. 88, p 11555-11561

Reference 49: Matsumoto, K. et al., "Biochem. Biophys. Res. Commun.", (US), 1997 Vol. 241, p 352-354

Reference 50: Nakamura, S. et al., "Diabetes", (US), 1997, Vol. 46, p 895-899

Reference 51: Beisswenger, P. J. et al., "Diabetes, (US), 1999, Vol. 48, p 198-202

Reference 52: Thornalley, P. J. et al., "Endocrinol. Metab.", (US), 1996, Vol. 3, p 149-166

SUMMARY OF THE INVENTION

Problems

Based on the above finding, a further study was conducted to provide a medicament for preventing and treating a disease associated with a protein modification product (s) (i.e., AGEs and/or ALEs) produced by reacting with a carbonyl compound under the non-enzymatic condition. As the result, the present inventors found that 3-methyl-1-phenyl-2-pyrazolin-5-one and their pharmaceutically acceptable salts inhibit effectively the production of protein modification products such as AGEs, ALEs, etc., and on the basis of this finding, an invention on inhibitor of protein modification products formation comprising said compounds as the active ingredient was completed (Japanese Patent Application No. 2003-076955).

The present inventors conducted a further study and found that analogs which are converted phenyl moiety at 1-position and methyl moiety at 3-position of said 3-methyl-1-phenyl-2-pyrazolin-5-one to another substituents also represent similar activity and that said 3-methyl-1-phenyl-2-pyrazolin-5-one or analogs thereof cause vitamin B6 deficiency when they are administered in organisms. A further study was conducted to solve this problem. As the result, the present inventors found that such vitamin B6 deficiency is caused by the capturing of vitamin B6 molecules in blood by 2-pyrazolin-5-one ring, which is basic skeleton of 3-methyl-1-phenyl-2-pyrazolin-5-one or analogs thereof. Also it was found that such capturing is caused by the binding of methylene moiety at 4-position of said 2-pyrazolin-5-one ring to vitamin B6 molecules.

Means for Solving Problems

Based on the fact, the present invention was completed and its purpose is inhibiting the vitamin B6 deficiency, which is unavoidable side effect relating to 3-methyl-1-phenyl-2-pyrazolin-5-one or analogs thereof, which are useful as inhibitor of protein modification products formation. This purpose was completed by the present invention, i.e. introducing a substituent which inhibit the binding of vitamin B6 molecules, to 3-methyl-1-phenyl-2-pyrazolin-5-one or analogs thereof on said methylene moiety at 4-position.

Provided that, the substituent introduced to methylene at 4-position are not always present stably depending on the variation. For example, when to introduce pyridoxal residue to methylen at 4-position, 3-methyl-1-phenyl-2-pyrazolin-5-one is reacted with pyridoxal, then actually obtain not 4-(3-hydroxy-5-hydroxymethyl-2-methylpyridin-4-yl-methylene)-1-phenyl-2-pyrazolin-5-one, but 1-(5-hydroxy-3-methyl-1-phenyl-1H-4-yl)-6-methyl-1,3-dihydrofuro[3,4-c]pyridin-7-ol.

The reason is considered that once the former is formed followed by intramolecular rearrangement to form the latter as depicted following scheme:

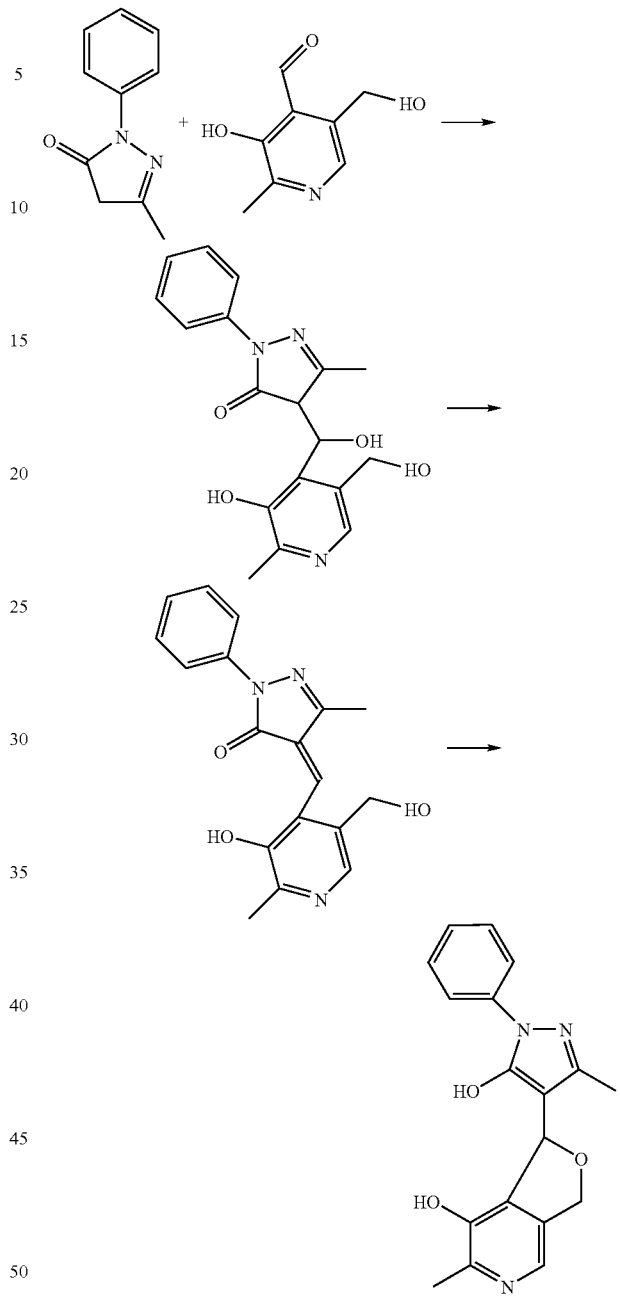

According to the previous study, the compounds introduced to the methylene moiety at 4-position to prevent the binding of vitamin B6 molecules represent generally the formation of protein modification products inhibiting effect regardless of their intramolecular rearrangement as described above.

DETAILED DESCRIPTION OF THE PREFERRED EMBODIMENTS

Namely, the present invention provides a inhibitor of protein modification products formation comprising as an active ingredient a compound having a formation of protein modification products inhibiting effect with suppress of vitamin B6 deficiency as an adverse effect. The scope of this invention covers specifically following technical embodiments:spects:
(i) a inhibitor of protein modification products formation comprising as an active ingredient a compound which is introduced a substituent that inhibit the binding of vitamin B6 molecules (comprising of that derived from vitamin B6 molecules itself) to 1-substituted-, unsubstituted-3-substituted- or unsubstituted-2-pyrazolin-5-one at the 4-position in free form or salt form or intramolecular rearranged bodies thereof;
(ii) a inhibitor of protein modification products formation according to (i), wherein the compound as the active ingredient is selected from compounds of formula (I):

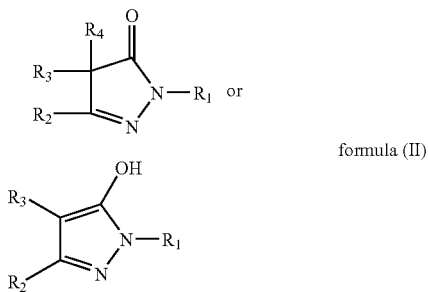

[wherein R1 is substituted or unsubstituted aromatic ring; and each of R2, R3 and R4 is a hydrogen atom or monovalent organic group, or alternatively R2 and R3 cooperate to form a condensed ring or R3 and R4 cooperate to represent a divalent organic group, provided that R3 and R4 are not simultaneously hydrogen atoms]
in free or salt form;
(iii) a inhibitor of protein modification products formation according to (ii), wherein the R1 aromatic ring moiety is up to 20-membered carbocyclic or heterocyclic aromatic ring group optionally comprising of up to 4 hetero atoms and optionally comprising up to 3 substituents.
(iV) a inhibitor of protein modification products formation according to (ii) or (iii), wherein each of R2, R3 or R4 monovalent organic group independently straight chain or cyclic aliphatic, alicyclic or aromatic hydrocarbon group having up to 30 carbon atoms optionally comprising of up to 3 substituents, or halogen, nitro, amino, hydroxy, thiol, carboxy, carboxy (lower) alkyl, lower alkoxycarbonyl, formyl, lower alkanoyl, lower alkylamino, di(lower) alkylamino, lower alkanoylamino, aryl (lower) alkanoyl, aryloxy-amino, sulfonic acid or 3- to 7-membered heterocyclic group optionally comprising of substituents;
(v) a protein modification products according to (ii) or (iii), wherein the R2 and the R3 cooperate to form a condensed ring which is 5- or 6-membered saturated carboncyclic ring optionally comprising of substituents;
(vi) a inhibitor of protein modification products formation according to (ii) or (iii), wherein the R3 and the R4 cooperate to form bivalent organic group which is selected from phenylmethylene, phenyl-alkenylmethylene, quinolinyl-methylene, furanyl-methylene, diazolyl-methylene, aminomethylene, di (lower) alkylamino-methylene, pyridyl-methylene and thio-phenylmethylene optionally comprising of substituents;
(7) a inhibitor of protein modification products formation according to any one of (iii) to (vii), wherein the substituents are selected from lower alkyl, lower alkenyl, lower alkoxy, lower alkenyloxy, lower alkanoyl, halo (lower) alkyl, carboxyl, lower alkoxycarbonyl, carboxy (lower) alkyl, halogen, nitro, amino, lower alkylamino, di (lower) alkylamino, lower alkanoylamino, hydroxy, thiol, hydroxysulfonyl, aminosulfonyl, aryl (lower) alkanoyl, aryloxyamino, aryl, aryl (lower)alkyl, cycro (lower) alkyl, cycro (lower) alkenyl, cycro (lower) alkyl (lower) alkyl and 3- to 7- membered heterocyclic group;
(viii) a inhibitor of protein modification products formation according to (ii), wherein the R1 is phenyl group, the R2 is methyl group, the R3 and the R4 cooperate to form 3-hydroxy-5-hydroxymethyl-2-methylpyridin-4-yl-methylene in formula (I);
(ix) a inhibitor of protein modification products formation according to (ii), wherein the R1 is phenyl group, the R2 is methyl group, the R3 is 6-methyl-1,3-dihydrofuro-[3,4-c]-pyridin-7-ol group in formula (II);
(x) a inhibitor of protein modification products formation according to any one of (i) to (ix), wherein the protein modification products is selected from AGEs, ALEs and combination thereof;
(xi) a inhibitor of protein modification products formation according to (x), wherein the protein modification products is AGEs;
(xii) a inhibitor of protein modification products formation according to (xi), wherein the AGEs is pentosidine;
(xiii) a renal tissue protecting agent comprising the inhibitor of protein modification products formation according to any one of (i) to (xii);
(xiv) a peritoneal dialysate comprising the inhibitor of protein modification products formation according to any one of (i) to (xii);
(xv) a hemodialysis fluid comprising the inhibitor of protein modification products formation according to any one of (i) to (xii);
(xvi) a method for reduction of the amount of a carbonyl compound(s) in a liquid sample, which comprises contacting the inhibitor of protein modification products formation according to any one of (i) to (xii) with the liquid sample;
(xvii) a method for suppression of the formation of a protein modification products in the blood or peritoneal dialysate of a patient, which comprises contacting the inhibitor of protein modification products formation according to any one of (i) to (xii) with said blood or peritoneal dialysate;
(xviii) a method for suppression of the vitamin B6 deficiency caused by said inhibitor of protein modification products formation, which comprises introducing a substituent that inhibit the binding of vitamin B6 molecules (comprising of that derived from vitamin B6 molecules itself) to 1-substituted-, unsubstituted-3-substituted- or unsubstituted-2-pyrazolin-5-one at the 4-position in free form or salt form, which is useful as protein modification products production inhibiting agent;
(xix) a method according to (xviii), wherein the 1-substituted-, unsubstituted-3-substituted- or unsubstituted-2-pyrazolin-5-one is formula:

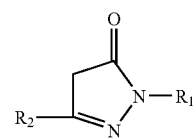

[wherein R1 is hydrogen atom or substituted or unsubstituted aromatic ring; and R2 is hydrogen atom or monovalent organic group];

(xx) a method according to (xvi), wherein the substituent, which is introduced at 4-position and inhibits binding of vitamin B6 molecules, is selected from organic group;

(xxi) a compound introduced a substituent that inhibit the binding of vitamin B6 molecules (comprising of that derived from vitamin B6 molecules itself) to 1-substituted-, unsubstituted-3-substituted- or unsubstituted-2-pyrazolin-5-one at the 4-position in free form or salt form, or intramolecular rearranged bodies thereof;

(xxii) a compound of

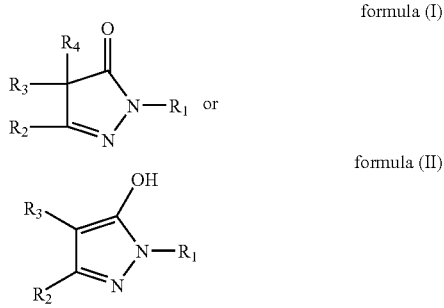

formula (I)

or formula (II)

[wherein R1 is substituted or unsubstituted aromatic ring; and each of R2, R3 and R4 is a hydrogen atom or monovalent organic group, or alternatively R2 and R3 cooperate to form a condensed ring or R3 and R4 cooperate to represent a divalent organic group, provided that R3 and R4 are not simultaneously hydrogen atoms] in free or salt form;

(xxiii) a compound according to (xxii), wherein the R1 is phenyl group, the R2 is methyl, the R3 and the R4 cooperate to form 3-hydroxy-5-hydroxymethyl-2-methylpyridin-4-yl-methylene group;

(xxiv) a compound according to (xxii), wherein the R1 is phenyl group, the R2 is methyl group, the R3 is 6-methyl-1,3-dihydrofuro-[3,4-c]-pyridin-7-ol group;

(xxv) use of the compound according to any one of (xxi) to (xxiv) for preparation of inhibitor of protein modification products formation;

(xxvi) a method for treatment of a disease mediated by the production of a protein modification products, which comprises administering a therapeutically effective amount of the compound according to any one of (xxi) to (xxiv) to a patient in need of such treatment.

The term "protein modification products" herein used is intended to mean a protein modification products (e.g., AGEs, ALEs, etc.) produced by the reaction with a carbonyl compound under a non-enzymatic condition formed by the reaction with carbonyl compounds under the non-enzymatic condition and cover AGEs and ALEs unless otherwise stated specifically. The protein modification products may be thus AGEs or ALEs, or their combination. Examples of AGEs are pentosidine, crossrine, X1 (fluorolink), pyropyridine, pyrarine, carboxymethyl-lysine, imidazolone compounds, carboxyethyl-lysine, MGO dimer, GO dimer, imidazolidine and argupyrimidine. Examples of ALEs are malondialdehydolysine, modified hydroxynonenal, etc.

The term "carbonyl compound" is intended to mean a compound having a carbonyl group causing protein modification regardless of being derived from organisms or non-organisms and covers dicarbonyl compounds. Examples of the carbonyl compound include arabinose, GO, MGO, 3-DG, glycolaldehyde, dehydroascorbic acid, hydroxynonenal, marondialdehyde, acrolein, 5-hydroxy-methylfurfural, formaldehyde, levulinic acid, furfural, etc.

The term "vitamin B6 deficiency" refers to several disease caused by the deficiency of vitamin B6, and includes angular cheilitis, mouth inflammation, glossitis, chelitis, acute and chronic eczema, contact dermatitis, peripheral neuritis, anemia, hypolymphemia and nerve disorder.

A compound as an active ingredient of "inhibitor of protein modification products formation" which is introduced a substituent that inhibit the binding of vitamin B6 molecules (comprising of that derived from vitamin B6 molecules itself) to 1-substituted-, unsubstituted-3-substituted- or unsubstituted-2-pyrazolin-5-one at the 4-position in free form or salt form, or rearranged bodies thereof may finally suppress the production of protein modification products regardless of in vivo, ex vivo and/or in vitro. The term "finally suppress" may caused by their effect to trap the carbonyl compounds or by suppressing the reaction to form protein modification products. It allows any mechanism to suppress finally the production of protein modification products, there is no limitation of their mechanism. In addition, the term "inhibitor" or "protectant" includes medicament for preventive and/or therapeutic use.

An active ingredient of inhibitor of protein modification products formation according to the present invention is a compound of formula (I) or (II).

In formula (I) and (II), R1 represents hydrogen atom or unsubstituted or substituted aromatic ring (includes heterocyclic ring) group. "aromatic ring group" involves not more than 20 ring constituent atom (hetero atoms such as oxygen, sulfate or nitrogen may be present therein and the number of them is not more than 4), in particular are preferred aryl comprising 6 to 10 ring constituent carbon atoms (for example phenyl or naphthyl).

The substituents may be selected from one or more of for example, lower alkyl, lower alkenyl, lower alkoxy, lower alkenyloxy, lower alkanoyl, halo (lower) alkyl, carboxyl, lower alkoxycarbonyl, carboxy (lower) alkyl, halo (such as chlorine, bromide, iodine, fluorine), nitro, amino, lower alkylamino, di (lower) alkylamino, lower alkanoylamino, hydroxy, thiol, hydroxysulfonyl, aminosulfonyl, aryl (lower) alkanoyl, aryloxyamino, aryl, aryl (lower) alkyl, cycro (lower) alkyl, cycro (lower) alkenyl, cycro (lower) alkyl (lower) alkyl, 3- to 7-membered hetero cyclic (such as oxadiazolyl, thiadiazolyl). The number of substituents is not limited, however, usually not more than 3.

The substituted or unsubstituted aromatic ring group R1 covers following examples: phenyl, naphthyl, o-, m- or p-lower alkylphenyl (such as o-methylphenyl, p-methylphenyl, p-ethylphenyl), o-, m- or p-lower alkoxyphenyl (such as o-, m- or p-methoxyphenyl, o-, m- or p-ethoxyphenyl), o-, m- or p-aminophenyl, o-, m- or p-nitrophenyl, o-, m- or p-halophenyl (such as o-, m- or p-chlorophenyl, o-, m- or p-fluorophenyl), o-, m- or p-halo-(lower)-alkylphenyl (such as o-, m- or p-trifluoromethyl-phenyl), o-, m- or p-sulfamoylphenyl, o-, m- or p-carboxyphenyl, o-, m- or p-lower alkoxycarbonyl-phenyl (such as o-, m- or p-methoxycarbonyl-phenyl, o-, m- or p-ethoxycarbonylphenyl, o-, m- or p-isopropoxy-carbonylphenyl), o-, m- or p-lower alkanoylphenyl (such as o-, m- or p-acetylphenyl), di (lower) alkylphenyl (such as 3,4-dimethylphenyl), dihydroxyphenyl (such as 2,4-dihydroxyphenyl), 2-amino-4-carboxyphenyl, 3-amino-5-carboxyphenyl, 3-lower alkoxy-4-hydroxyphenyl (such as 3-methoxy-4-hydroxyphenyl), 3-carboxy-4-halophenyl (such as 3-carboxy-4-chlorophenyl).

Each of R2, R3 and R4 represent independently hydrogen atom or monovalent organic group. The term "monovalent organic group" covers substituted or unsubstituted hydrocarbon, halo, nitro, amino, hydroxy, thiol, carboxy, carboxy (lower) alkyl, lower alkoxycarbonyl, formyl, lower alkanoyl, lower alkylamino, di (lower) alkylamino, lower alkanoylamino, aryl (lower) alkanoyl, aryloxyamino, sulfonic acid and 3- to 7-membered heterocyclic group. The term "hydrocarbon group" covers straight chain or cyclic aliphatic, alicyclic or aromatic hydrocarbon group comprising not more than 30, preferably not more than 8 carbon atoms. In particular, for example alkyl, alkenyl, alkynyl, cycroalkyl, cycroalkenyl and aryl group are included. The term "3- to 7-membered heterocyclic group" comprises of not more than 3 hetero atoms as ring constituent atom. For example, pyrrolidino, piperidino, morpholino and thiamorpholino are included. The variety and number of the substituent is as defined in R1. Provided that, R3 and R4 are not simultaneously hydrogen atoms.

Alternatively, R2 and R3 cooperate to form a condensed ring. In said condensed ring, 5- or 6-membered saturated carbon ring (i.e. R2+R3=trimethylene or tetramethylene) are preferred, optionally comprising of substituents. Furthermore, R3 and R4 cooperate to form divalent organic group. In said divalent organic group, for example, methylene-type and spiro-type are included. In methylene-type, for example phenylmethylene, phenyl-alkenylmethylene, quinolinyl-methylene, furanyl-methylene, diazolyl-methylene, aminomethylene, di (lower) alkylamino-methylene, pyridyl-methylene and thiophenyl-methylene are included, optionally comprising of substituents. The variety and number of substituent in such condensed ring or divalent organic group is as defined in R1.

The term "lower" in relations to alkyl, alkoxy, alkanoyl and etc. herein above means the group comprising up to 8 carbon atoms, preferably up to 5 carbon atoms.

The compounds (I) or (II) of this invention are exemplified as follows:

1. 2-(3-amino-5-oxo-1-phenyl-4,5-hydro-1H-pyrazol-4-yl)-2-oxo-N-phenyl-acetamide;
2. 2-(3-amino-5-oxo-1-phenyl-4,5-hydro-1H-pyrazol-4-yl)-2-oxo-N-thiazol-2-yl-acetamide;
3. 2-(3-amino-5-oxo-1-phenyl-4,5-hydro-1H-pyrazol-4-yl)-2-oxo-acetamide;
4. 2-(3-amino-5-oxo-1-phenyl-4,5-hydro-1H-pyrazol-4-yl)-N-(3,4-dimethyl-phenyl)-4-oxo-butylamide;
5. 2-(4-amino-phenyl)-4-(2-hydroxy-ethyl)-5-methyl-2,4-hydro-pyrazol-3-one;
6. 5-amino-2-phenyl-4-(1-phenyl-1H-tetrazol-5-yl-sulfanil)-2,4-dihydro-pyrazol-3-one;
7. 3-(3-methyl-5-oxo-1-penyl-4,5-dihydro-1H-pyrazol-4-yl)-propionic acid;
8. N-(3-methyl-5-oxo-1-phenyl-4,5-dihydro-1H-pyrazol-4-yl)-acetamide;
9. 4-[(5-hydroxy-3-methyl-1-phenyl-1H-pyrazol-4-yl)-phenyl-methyl]-5-methyl-2-phenyl-2,4-dihydro-pyrazol-3-one;
10. 2-phenyl-3a,4,5,6-tetrahydro-2H-cycropentapyrazol-3-one;
11. 4-methyl-N-(3-methyl-5-oxo-1-phenyl-4,5-dihydro-1H-pyrazol-4-yl)-benzenesulfonamide;
12. N-(3-methyl-5-oxo-1-phenyl-4,5-dihydro-1H-pyrazol-4-yl)-acetamide;
13. 5-methyl-2-(3-nitro-phenyl)-4-(1-phenyl-1H-tetrazol-5-yl-sulfanil)-2,4-dihydro-pyrazol-3-one;
14. N-[5-oxo-1-phenyl-4-(1-phenyl-1H-tetrazol-5-yl-sulfanil)-4,5-dihydro-1H-pyrazol-3-yl]-benzamide;
15. 4-(hydroxy-phenyl-methyl)-2-phenyl-5-trifluoromethyl-2,4-dihydro-pyrazol-3-one;
16. 4-(1-hydroxyimino-ethyl)-2,5-diphenyl-2,4-dihydro-pyrazol-3-one;
17. 5,5'-dimethyl-2,2'-diphenyl-2,4,2',4'-tetrahydro-[4,4']-bipyrazol-3,3'-dione;
18. 2-(4-chloro-phenyl)-4-ethyl-5-methyl-2,4-dihydro-pyrazol-3-one;
19. 4-[4-(4-methoxy-phenyl)-thiazole-2-yl-sulfanil]-5-methyl-2-phenyl-2,4-dihydro-pyrazol-3-one;
20. 4-(2-oxo-2-phenyl-ethyl)-2-phenyl-5-propyl-2,4-dihydro-pyrazol-3-one;
21. 5-methyl-2-phenyl-4-(4-p-toluyl-thiazole-2-yl-sulfanil)-2,4-dihydro-pyrazol-3-one;
22. 2-(4-fluoro-phenyl)-4-[[1-(4-fluoro-phenyl)-5-hydroxy-3-methyl-1H-pyrazol-4-yl]-(2-hydroxy-phenyl)-methyl]-5-methyl-2,4-dihydro-pyrazol-3-one;
23. N-(3,4-dimethyl-phenyl)-2-(3-methyl-5-oxo-1-phenyl-4,5-dihydro-1H-pyrazol-4-yl)-2-oxo-acetamide;
24. 5-(4-chloro-benzoyl)-4,4-dihydroxy-2-phenyl-2,4-dihydro-pyrazol-3-one;
25. sodium; 4-hydroxy-3-methyl-5-oxo-1-phenyl-4,5-dihydro-1H-pyrazol-4-sulfonate;
26. 5-methyl-4,4-di-morpholin-4-yl-2-phenyl-2,4-dihydro-pyrazol-3-one;
27. sodium 3-benzoylamino-4-hydroxy-5-oxo-1-phenyl-4,5-dihydro-1H-pyrazol-4-sulfonate;
28. 3-methyl-1-phenyl-5-oxo-4-spiro-(3-oxo-2,3-dihydro-benzo[b]thiophen-2-yl)-4,5-dihydro-1H-pyrazol;
29. 4,4,5-trimethyl-2-phenyl-2,4-dihydro-pyrazol-3-one;
30. 4,10-dimethyl-2,8, 1 1-triphenyl-2,3,8,9-tetraza-dispiro [4.0.4.1]undeca-3,9-diene-1,7-dione;
31. 2-(2-chloro-phenyl)-4-(3-ethoxy-4-hydroxy-benzylidene)-5-methyl-2,4-dihydro-pyrazol-3-one;
32. 2-(2-chloro-phenyl)-4-(4-dimethylamino-benzylidene)-5-methyl-2,4-dihydro-pyrazol-3-one;
33. 5-methyl-4-(3-phenyl-allylidene)-2-(3-trifluoromethyl-phenyl)-2,4-dihydro-pyrazol-3-one;
34. 3-{5-[3-methyl-5-oxo-1-(4-sulfamoyl-phenyl)-1,5-dihydro-pyrazol-4-ylidene-methyl]-furan-2-yl}-benzoic acid;
35. 4-(4-dimethylamino-benzylidene)-2-(3-fluoro-phenyl)-5-methyl-2,4-dihydro-pyrazol-3-one;
36. 3-{4-[4-(3-chloro-4,5-dihydro-pyrazol-1-yl)-benzylidene]-3-methyl-5-oxo-4,5-dihydro-pyrazol-1-yl}-benzoic acid;
37. 3-[4-(2-hydroxy-benzylidene)-5-oxo-3-phenyl-4,5-dihydro-pyrazol-1-yl]-benzoic acid;
38. 3-[1-(3-chloro-phenyl)-3-methyl-5-oxo-1,5-dihydro-pyrazol-4-ylidene-methyl]-1H-quinolin-2-one;
39. 3-{5-[3-methyl-5-oxo-1-(4-sulfamoyl-phenyl)-1,5-dihydro-pyrazol-4-ylidene-methyl]-furan-2-yl}-benzoic acid-methyl ester;
40. 4-(4-benzo[1,3]dioxol-5-ylmethylene-3-methyl-5-oxo-4,5-dihydro-pyrazol-1-yl)-benzoic acid-methyl ester;
41. 4-{3-methyl-5-oxo-4-[5-(4-sulfamoyl-phenyl)-furan-2-yl-methylene]-4,5-dihydro-pyrazol-1-yl}-benzoic acid-methyl ester;
42. 2-(4-chloro-phenyl)-4-(2,4-dihydroxy-benzylidene)-5-methyl-2,4-dihydro-pyrazol-3-one;
43. 2-(4-chloro-phenyl)-4-(3-hydroxy-benzylidene)-5-methyl-2,4-dihydropyrazol-3-one;
44. 4-(3,4-dihydroxy-benzylidene)-5-methyl-2-p-toluyl-2,4-dihydro-pyrazol-3-one;
45. 3-[1-(4-acetyl-phenyl)-3-methyl-5-oxo-1,5-dihydro-pyrazol-4-ylidene]-1,3-dihydro-indol-2-one;

46. 2-(4-fluoro-phenyl)-4-(5-hydroxy-3-methyl-1-o-toluyl-1H-pyrazol-4-yl-methylene)-5-methyl-2,4-dihydro-pyrazol-3-one;
47. 2-(4-chloro-phenyl)-4-(4-hydroxy-3-methoxy-benzylidene)-5-trifluoromethyl-2,4-dihydro-pyrazol-3-one;
48. 2-(4-ethyl-phenyl)-4-(4-hydroxy-benzylidene)-5-methyl-2,4-dihydro-pyrazol-3-one;
49. 4-[4-(4-hydroxy-benzylidene)-3-methyl-5-oxo-4,5-dihydro-pyrazol-1-yl]-benzenesulfonamide;
50. 4-(5-oxo-4-thiophene-2-yl-methylene-3-trifluoromethyl-4,5-dihydro-pyrazol-1-yl)-benzoic acid-ethyl ester;
51. 4-[4-(4-dimethylamino-benzylidene)-5-oxo-3-trifluoromethyl-4,5-dihydro-pyrazol-1-yl]-benzenesulfonamide;
52. 4-isopropylidene-5-methyl-2-phenyl-2,4-dihydro-pyrazol-3-one;
53. 4-(4-hydroxy-benzylidene)-2-phenyl-5-trifluoromethyl-2,4-dihydro-pyrazol-3-one;
54. 4-(2,4-dihydroxy-benzylidene)-2-(3,4-dimethyl-phenyl)-5-methyl-2,4-dihydro-pyrazol-3-one;
55. 3-[4-(3-ethoxy-4-hydroxy-benzylidene)-3-methyl-5-oxo-4,5-dihydro-pyrazol-1-yl]-benzoic acid;
56. 4-[4-(3,5-di-tert-butyl-4-hydroxy-benzylidene)-3-methyl-5-oxo-4,5-dihydro-pyrazol-1-yl]-benzoic acid;
57. 3-[3-(4-hydroxy-3-methoxy-benzylidene)-3-methyl-5-oxo-4,5-dihydro-pyrazol-1-yl]-benzoic acid;
58. 3-[3-hydroxy-4-(4-hydroxy-3-methoxy-benzylidene)-5-oxo-pyrazolidin-1-yl]-benzoic acid;
59. 4-(3-hydroxy-2,4-dimethoxy-benzylidene)-5-methyl-2-phenyl-2,4-dihydro-pyrazol-3-one;
60. 4-[4-(4-hydroxy-3-methoxy-benzylidene)-3-methyl-5-oxo-pyrazolidin-1-yl]-benzoic acid-isopropyl ester;
61. 2-chloro-5-[4-(2-chloro-4-hydroxy-5-methoxy-benzylidene)-3-methyl-5-oxo-4,5-dihydro-pyrazol-1-yl]-benzoic acid;
62. 4-[4-(4-hydroxy-benzylidene)-3-methyl-5-oxo-4,5-dihydro-pyrazol-1-yl]-benzoic acid-ethyl ester;
63. 4-[4-(4-hydroxy-benzylidene)-5-oxo-3-trifluoromethyl-4,5-dihydro-pyrazol-1-yl]-benzoic acid-ethyl ester;
64. 4-[4-(4-hydroxy-benzylidene)-3-methyl-5-oxo-4,5-dihydro-pyrazol-1-yl]-benzoic acid;
65. 4-dimethylaminomethylene-5-methyl-2-phenyl-2,4-dihydro-pyrazol-3-one;
66. 4-(5-hydroxy-3-methyl-1-phenyl-1H-pyrazol-4-yl-methylene)-5-methyl-2-phenyl-2,4-dihydro-pyrazol-3-one;
67. 4-(4-chloro-benzylidene)-5-methyl-2-phenyl-2,4-dihydro-pyrazol-3-one;
68. 1-(5-hydroxy-3-methyl-1-phenyl-1H-pyrazol-4-yl)-6-methyl-1,3-dihydro-furo[3,4-c]pyridin-7-ol;
69. 1-(5-hydroxy-3-methyl-1-phenyl-1H-pyrazol-4-yl)-6-methyl-1,3-dihydro-furo[3,4-c]pyridin-7-ol (hydrochloric acid salt);
70. 4-(4-hydroxy-benzylidene)-5-methyl-2-phenyl-2,4-dihydro-pyrazol-3-one;
71. 2-(3-chloro-phenyl)-4-(4-hydroxy-benzylidene)-5-methyl-2,4-dihydropyrazol-3-one;
72. 4-(4-benzyloxy-benzylidene)-5-methyl-2-phenyl-2,4-dihydropyrazol-3-one;
73. 2-(3-chloro-phenyl)-5-methyl-2H-pyrazol-3,4-dione 4-oxym;
74. 5-(5-oxo-1,3-diphenyl-1,5-dihydro-pyrazol-4-ylidene)-4-phenyl-4,5-dihydro-[1,3,4]thiazole-2-carboxilic acid-ethyl ester;
75. 4-[1,3]dithioran-2-ylidene-5-methyl-2-phenyl-2,4-dihydro-pyrazol-3-one;
76. 5-(4-chloro-phenylsulfanilmethyl)-2-phenyl-4-[N'-(3-trifluoromethyl-phenyl)-hydrazino]-2,4-dihydro-pyrazol-3-one;
77. 4-(5-benzoyl-3-phenyl-3H-[1,3,4]thiadiazol-2-ylidene)-2,5-diphenyl-2,4-dihydro-pyrazol-3-one;
78. phosphoric acid mono-[5-hydroxy-6-methyl-4-(3-methyl-5-oxo-1-phenyl-1,5-dihydro-pyrazol-4-ylidene-methyl)-pyridin-3-yl-methyl]ester.

To prepare the interest compound (I) of this invention, 1-substituted-, unsubstituted-3-substituted- or substituted-2-pyrazolin-5-one (III) as depicted following formula is generally subjected to appropriate chemical reaction known per se depending upon the variety of substituent which should introduced on 4-position:

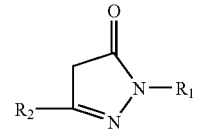

[wherein R1 is hydrogen atom or substituted or unsubstituted aromatic ring; and R2 is hydrogen atom or monovalent organic group].

For example, the compound (III) is reacted with aldehyde of formula: R3-CHO (IV) to form the compound (I). The compound (I) may afford as the compound (II) by intramolecular rearrangement. The reaction is usually carried out by treating the compound (III) and aldehyde (IV) in aqueous vehicle under alkalies condition, or in organic solvent (such as tetrahydrofuran, dioxan), in presence of organic or inorganic base at −120 to 100° C.

The compound (III), the starting material, is known per se or may be prepared by any conventional chemical reaction. For example, 3-methyl-1-phenyl-2-pyrazolin-5-one (in the compound (III), R1 is phenyl and R2 is methyl) is referred to edaravone as its general name. The compound has free radical deleting activity, and is known as a medicament such as brain function normalizing agent (Japan patent publication No. 5-31523), peroxidized lipid production suppressing agent (Japan patent publication No. 5-35128), anti-ulcer agent (Japan patent No. 2906512), hyperglycemic suppressing agent (Japan patent No. 290651 3). However, it has not been known before Japan patent application 2003-076955 that edaravone traps carbonyl compound, improves carbonyl stress condition, therefore is effective to prevent or treat several disease caused by carbonyl stress, namely useful as inhibitor of protein modification products formation.

As described above, the compound (I) or (II) itself shows formation of protein modification products inhibiting effect without vitamin B6 deficiency as an adverse effect in organisms. The fact can be confirmed by the following test:

(A) Test to prove that the compound (I) itself exhibits a formation of protein modification products inhibiting effect:

(1) To a plasma sample taken from a dialysis patient without diabetes, the compound of this invention is added, and after a certain period of time, an amount of pentosidine formed is determined using pentosidine, a typical example of AGEs, as an index.

(2) Phenylalanine reacts with OH radical in presence of hydroxy radical to form o- or m-tyosine. Further, tyrosine reacts with NO radical in presence of peroxynitrite to form nitrotyrosine. A radical causes disorder of kidney in organisms. Accordingly, the radical capturing ability of the compound of this invention in phenylalanine-radical reacting system is determined.

(B) Test to prove that the compound (I) does not cause vitamin B6 deficiency:

(1) To a solution of vitamin B6, the compound of this invention is added, and after a certain period of time, an amount of vitamin B6 remained is determined.

(2) To a normal rat, the compound of this invention is administered, and after a certain period of time, a presence or absence of vitamin B6 deficiency is determined.

The inhibitor of protein modification products formation of this invention comprising the compound (I) or (II) as an active ingredient is usable to prevent and/or treat for following conditions: renal failure, diabetic complication (nephropathy, nerve disorder, retinopathy, cataract, etc.), arteriosclerosis, dialysis amyloidosis which is complication of dialysis, and peritoneal sclerosis in peritoneal dialysis patient, Alzheimer's disease which is central neurological disease, Pick's disease and Parkinson disease, rheumatoid arthritis, sunlight erastic fibrosis, aging and etc. Said inhibitor is particularly usable to prevent and/or treat renal disorder.

The compound (I) of this invention may directly or with treatment such as dilution with water, use when it is used as preventive agent or therapeutic agent, and may use in combination with medicinal drugs or quasi drugs. The blending quantity in this case is selected suitable depending on the condition or the product and 0.001 to 50% by weight, especially 0.01 to 10% by weight of the compound is usually suitable when it is administered systemically. Since sufficient preventive or therapeutic effect may not achieve when it comprises less than 0.001% by weight, or since property of the product such as stability or flavor may be impaired when it comprises more than 5% by weight, they are not preferred.

The compound (I) of this invention may be comprised in free or salt form. The salt includes pharmaceutically acceptable salt, for example salt with inorganic or organic base, acid addition salt such as inorganic acid, organic acid, and basic or acidic aminoic acid addition salt. The salt with inorganic base includes for example alkali metal (such as sodium or potassium) salt, alkali earth metal (such as calcium, magnesium) salt, alminum salt and ammonium salt. The salt with organic base includes for example salts with primary amine (such as ethanol amine), secondary amine (such as diethyl amine, diethanol amine, dicyclohexyl amine, N,N'-dibenzylethylen diamine),and tertiary amine (such as trimethylamine, triethylamine, biridine, picoline, triethanol amine).

The salt with inorganic acid is exemplified salts with hydrochloric acid, hydrobromic acid, nitric acid, sulfuric acid and phosphoric acid, and the salt with organic acid is exemplified salts with formic acid, acetic acid, lactic acid, trifluoro acetic acid, fumaric acid, oxalic acid, tartaric acid, maleic acid, benzoic acid, citric acid, succinic acid, malic acid, methanesulfonic acid, ethanesulfonic acid, benzenesulfonic acid and p-toluenesulfonic acid. In addition, the salt with basic aminoic acid is exemplified salts with arginine, lysine and ornithine, and the acidic aminoic acid is exemplified salts with aspargine acid and glutamic acid.

The compound (I) or (II) of this invention is optionally used in combination with known agent such as amino guanidine, pyridoxamine derivative, OPB-9195, biguanide compound, bridge formation inhibitor, enzyme degrading Amadori compounds, GSH, cystein, acetyl cystein, vitamin E, ubiquinol, aldose reduction enzyme inhibitor, carbonyl compounds trapping agent to enhance sustentation of protein modification products formation inhibiting effect. In addition, identify material(s) which deactivate or degrade the compound (I) or (II), select materials which inhibit the identified materials and selected material are used together of blended to obtain the stability of active ingredient in the composition.

The administration route of the medicament of this invention may be selected from transmucosal, transdermal, intramuscular, subcutaneous or intrarectal administration other than oral or intravenous administration, and depending on the administration route, several preparations may be used. Each preparation is described herein after, but formulation used in this invention is not limited thereto, any kind of formulation used in pharmaceutical preparation may be used.

Used as preventive agent or therapeutical agent for condition associated with protein modification products, an oral dose of the compound (I) or (II) is generally range of preferably 0.3 mg/kg to 300 mg/kg, more preferably 1 mg/kg to 100 mg/kg. In systemic administration, especially in intravenous administration, dose will vary depending on their sex, age, body weight or etc. but usually administer to make available blood level in the range of 2 µg/mL to 200 µg/mL, more preferably 5 µg/mL to 100 µg/mL Dosage form of oral administration includes powder, granule, capsule, pill, tablet, elixir, suspension, emulsion and syrup, and selects suitably. Further, dosage form of intraorally local administration includes masticatory, sublingual formulation, buccals, lozenge, ointment, adhesive preparation and liquid, and selects suitably. Besides, some modifications such as sustained release, stable, ease disintegrate, hard disintegrate, enteric, ease absorption may be done.

Any known drug delivery system (DDS) may be adopted to each preparations sited above. DDS preparation herein means the most suitable preparation form such as sustained release preparation, topical applicable preparation (such as lozenge, buccals and sublingual formulation), controlled release preparation, enteric preparation and gasteric preparation based on administration route, bioavailability, adverse effect and etc.

The component of DDS includes essentially medicament, medicament release module, encapsulating body and therapeutic program. For each component, in particular, the medicament whose blood level goes down quickly when stopped the release and which has a short half life is preferred, the encapsulating body which does not react with living tissue of administration site is preferred, in addition, the therapeutic program which maintain the best drug level in given period is preferred. The medicament release module comprise essentially medicament container, release controlling part, energy source and release hole or release surface. Such essential component is not needed getting together all of them, thus the best form can be selected by suitable addition or deletion.

Materials for DDS include high molecule, cyclodextrin derivative, and lecithin. The high molecule are selected from insoluble high molecule (such as silicon, ethylene-acetic vinyl copolymer, ethylene-vinylalcohol copolymer, ethylcellulose and cellulose acetate), soluble high molecule and hydroxyl gel forming high molecule (such as polyacrylamide, polyhydroxyethyl methacrylate cross-linked material, polyacryl cross-linked material, polyvinylalcohol, polyethylene oxide, water-soluble cellulose derivative, cross-linked poloxamer, chitin, chitosan), sustained soluble high molecule (such as ethylcellulose, partial ester of methylvinyl ether-maleic acid anhydride copolymer), gastric high molecule (such as hydroxypropylmethyl cellulose, hydroxy propylcellulose, carmellose sodium, macrogol, polyvinyl pyrolidone, methacrylic acid dimethylaminoethyl-methacrylic acid methyl copolymer), enteric high molecule (such as hydroxypropylmethyl cellulose phthalate, acetic acid phthalcellulose, hydroxypropylmethyl cellulose acetate succinate, carboxymethylethyl cellulose, acrylic acid group polymer), biodegradable high molecule (such as thermocoagulation or cross-linked albumin, cross-linked gelatin, collagen, fibrin, polycyanoacrylate, polyglycolic acid, polylactic acid, poly β-hydroxy acetic acid, polycaprolactam).

Particularly, silicon, ethylene-acetic acid vinyl copolymer, ethylenevinylalcohol copolymer and partial ester of methylvinyl ether-maleic acid anhydride copolymer may use for release control of drug, and cellulose acetate may use as a material of osmotic pump, ethylcellulose, hydroxypropylmethyl cellulose, hydroxypropyl cellulose and methylcellulose may use for membrane material of sustained release preparation, polyacryl cross-linked material may use for adhesive preparation for oral or ocular mucosa.

In addition, depending on the formulation (such as formulation for oral administration, injection, suppository), the preparation may be added suitable additives, for example solvent, diluent, coating agent, base, binding agent, lubricant, disintegrant, solubilizing agent, suspending agent, thickener, emulsifier, stabilizer, buffer, tonicity agent, soothing agent, preservative, flavoring agent, aromatic agent and/or colorant. For such additives, examples are listed following after, but not limited to.

The solvent includes purified water, injection solvent, saline, arachis oil, ethanol and glycerin. The diluent includes starch, lactose, glucose, sucrose, crystalline cellulose, calcium sulfate, calcium carbonate, talc, titanic oxide, trehalose and xylitol. The coating agent includes sucrose, gelatin, cellulose acetate phthalate and high molecule as sited above. The base includes petrolatum, vegetable oil, macrogol, oil in water emulsifier base and water in oil emulsifier base.

The binding agent includes starch and derivatives thereof, cellulose and derivative thereof, gelatin, alginate sodium, tragacanth, nature high molecules such as gum acacia, synthetic high molecules such as polyvinyl pyrrolidone, dextrin and hydroxypropyl starch. The lubricant includes stearic acid and salt thereof, talc, wax, wheat starch, macrogol, hydrogenated vegetable oil, sucrose fatty acid ester and polyethylene glycol. The disintegrant includes starch and derivative thereof, agar, gelatin powder, sodium hydrogen carbonate, cellulose and derivative thereof, carmellose calcium, hydroxypropyl starch, carboxymethyl cellulose and salt thereof as well as cross-linked structure there of and lower substituted hydroxypropyl cellulose.

The solubilizing agent includes cyclodextrin, ethanol, propylene glycol and polyethylene glycol. The suspending agent includes gum acacia, tragacanth, alginate sodium, alminum monostearate, citric acid and several surfactants. The viscose includes carmellose sodium, polyvinyl pyrrolidone, methylcellulose, hydroxypropylmethyl cellulose, polyvinylalcohol, tragacanth, gum acacia and alginate sodium. The emulsifier includes gum acacia, cholesterol, tragacanth, methylcellulose, various surfactants and lecithin.

The stabilizer includes bisulfite sodium, ascorbic acid, tocopherol, chelate agent, innert gas and reducing material. The buffer includes hydrogen phosphate sodium, acetic acid sodium and boric acid. The tonicity agent includes sodium chloride and glucose. The soothing agent includes procaine hydrochloride, lidocaine and benzyl alcohol. The preservative includes benzoic acid and salt thereof, p-hydroxybenzoic esters, chloro butanol, cationic soap, benzyl alcohol, phenol and methyl salicylate. The flavoring agent includes sucrose, saccharine, licorice extract, sorbitol, xylitol and glycerin. The aromatic agent includes spruce tincture and rose oil. The colorant includes water solubility food colorant and lake dye.

As described above, continuance of available blood level, enhanced bioavailability and etc. may predict by preparing DDS preparation such as sustained release preparation, enteric preparation or controlled drug release preparation. However, the compound (I) or (II) is deactivated or degraded in an organism, and as the result, there is possibility that desired effect may reduce or disappear. Accordingly, material(s) which inhibit the deactivator or degradator of the compound (I) or (II) are combined with the composition for prevention of treatment for the condition associated with protein modification products of this invention to continue the effect of the ingredient. Such material(s) may mix in preparation, and may administer separately. The material(s) which deactivate or degrade the compound (I) or (II) are identified, inhibitor of it such material(s) may be selected, and mixed or used together by a person skilled in the art suitably.

In the preparation, any ingredient used in normal composition as additives other than described above may be used, and an amount of such ingredient is selected in the range that the effect of this invention is not prevented.

The compound (I) or (II) of this invention may be also used to suppress the disorder from protein modification products in peritoneal dialysis and hemodialysis. Namely, the compound (I) or (II) as protein modification products formation inhibitor is added to conventional peritoneal dialysate or hemodialysate.

The method to reduce an amount of carbonyl compound in liquid sample according to this invention comprises the step that said liquid sample are contacted with the compound (I) or (II) as protein modification products formation inhibitor.

In addition, the method to suppress the formation of protein modification products according to this invention comprises the step that blood from patient or peritoneal dialysate is contacted with the compound (I) or (II) as protein modification products formation inhibitor. The protein modification products in dialysis includes protein modification products that is formed by the carbonyl compound derived from patient with peritoneal dialysis or hemodialysis and the protein modification products that is formed by carbonyl compound derived from peritoneal dialysate or hemodialysate themselves.

The composition of peritoneal dialysate or hemodialysate that is added the compound (I) or (II) according to this invention is selected from known one. Common peritoneal dialysate are composed of osmo-regulator (such as glucose), buffer (such as lactose, citric acid, malic acid, acetic acid, pyruvic acid, succinic acid and sodium hydrogencarbonate), and inorganic salts (such as sodium ion, potassium ion, magnesium ion, calcium ion and chloride ion). The peritoneal dialysate or hemodialysate that was added the compound (I) or (II) may be sealed off directly to sterilize by heat. By so doing, the formation of protein modification products from main ingredients accompanied with sterilization by heat or preservation.

In addition, liquid such as peritoneal dialysis is packed in separated container that consists of first chamber and second chamber, reducing sugar is packed in the first chamber and the compound (I) or (II) is packed in the second chamber, and all of them may be mixed before use. When aminoic acid is comprised, a person skilled in the art may adopt the best constitution such as third chamber.

Since the compound (I) or (II) suppresses the formation of protein modification products by intraperitoneal or intravascular administration, adverse effects such as peritoneal sclerosis may alleviated. Furthermore, it can be expected to work prevention and/or therapy of other conditions (such as diabetic complication). The dialysate may involve known agent such as amino guanidine other than the compound (I) or (II). Alternatively, it can be adopted in powdered dialysis agent.

The compound (I) or (II) may be injected to dialysis circuit that is equipped with suitable connector for coinjection. Alternatively, the compound (I) or (II) is directly injected into peritoneal cavity to mix with peritoneal dialysate in the peritoneal cavity. Alternatively, before peritoneal dialysate is injected to patient or while it collects in a peritoneal cavity, the compound (I) or (II) may be injected intravenously to suppress the formation of protein modification products effectively.

The dialysate is filled in suitable sealing container and sterilized. The sterilization by high-pressure steam and by hot-water is effective. In this case, the container that toxic substances are not eluted at high temperature and that have enough hardness to endure carriage after sterilization is used. In particular, commutative plastic bag that is made from for example polyvinyl chloride, polypropylene, polyethylene, polyester, ethylene acetate vinyl copolymer are included. In addition, to avoid degradation of liquid due to the effect of ambient air, the container that is filled with dialysate are further packed by packing materials which has high gas barrier property.

When sterilization is carried out by heat including high-pressure heat, if the compound (I) or (II) used has enough stability against treatment such as heat, the compound (I) or (II) is added previously to dialysate and then the mixed dialysate is sterilized. If the compound (I) or (II) used does not have stability against sterilization by heat, sterilization without heat can be carried out. Such sterilization includes, for example sterilization by filtration.

For example, such sterilization can be carried out by filtration with fine filter that is equipped with membrane filter having pore diameter about 0.2 μm. The dialysate that is sterilized by filtration is filled in the container such as flexible plastic bag, and then it is sealed. In addition, to peritoneal dialysate that is previously sterilized by heat may add the compound (I) or (II).

The timing of addition is not limited. Whether after or before sterilization, the compound (I) or (II) may be added, may be added just before or together with dialysis and may inject into peritoneal cavity directly after dialysate is injected.

The peritoneal dialysate of this invention is used for dialysis as current peritoneal dialysate or hemodialysate. Namely, for peritoneal dialysis, suitable amount of the peritoneal dialysate according to this invention is injected into peritoneal cavity of patient with dialysis to transfer low molecular weight ingredient in an organism into peritoneal dialysate through peritonea. The peritoneal dialysate is intermittently circulated and dialysis is continued depending on the condition of patient. At this stage, the compound (I) or (II) suppresses the formation of protein modification products in the dialysate or an organism. The carbonyl compounds transfer from blood or intraperitonea to peritoneal dialysate together with dialysis ingredient such as creatinine, inorganic salts or chlorine ion. Accordingly, adverse effect on an organism by protein modification products is reduced.

The compound (I) or (II) is used for not only dialysate, but also any liquid medicament such as nutrient infusion, electrolyte infusion or enteral or tube feeding.

The compound of this invention is usable to therapy as injection, however, involves a compound which start degrading immediately in solution and degrades about 40% after 12 hours (at 25° C.). The present inventors conducted a further study to provide injection which is administered in stable condition, comprising the compound of this invention. Accordingly, the present inventions provide also an injection which is administered in stable condition, comprising the compound of this invention.

Effect of the Present Invention

The present invention provides a inhibitor of protein modification products formation, which effectively suppresses the formation of protein modification products, such as AGEs or ALEs. Particularly, the present invention provides a medicament to prevent and/or treat for renal failure, diabetic complication such as nephropathy, nerve disorder, retinopathy, cataract and etc., arteriosclerosis, dialysis amyloidosis which is complication of dialysis, and peritoneal sclerosis in peritoneal dialysis patient, Alzheimer's disease which is central neurological disease, Pick's disease and Parkinson disease, rheumatoid arthritis, sunlight elastic fibrosis, aging and etc. In particular, a renal protective agent is provided which is applicable to renal failure and diabetic nephropathy, which is diabetic complication, as renal protective agent for depressor. The agent is usable to many patients in wide range without blood pressure-lowering effect as its medicinal properties. In addition, from the point that the compound of this invention suppresses endoplasmic reticulum stress (ER stress), the compound of this invention may use to treat for diseases, such as diabetes, Parkinson disease, rheumatoid arthritis.

EXAMPLES

This invention will be hereinafter illustrated more in details by way of Examples, but the scope of this invention should not be understood to be limited to these Examples.

Preparation Example 1

Preparation of 1-(5-hydroxy-3-methyl-1-phenyl-1H-pyrazol-4-yl)-6-methyl-1,3-dihydro-furo[3,4-c]pyridin-7-ol

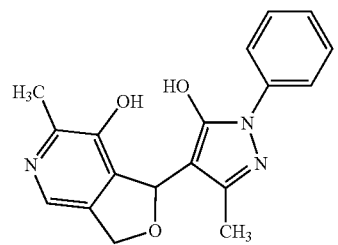

To a stirring solution of 3-methyl-1-phenyl-2-pyrazolin-5-one (1.74 g) (hereinafter, referred to edaravone) in 0.1M of NaOH (100 mL) at room temperature, were added dropwise a solution of pyridoxal hydrochloride (2.44 g) in water (100 mL) with stirring and then reacted. After dropwise, the mixture was stirred for 30 minutes and the reaction was stopped when it was appeared to finish deposition of white precipitate. The mixture was cooled to 4° C. in refrigerator to deposit sufficiently the precipitate. The reaction solution was stood to cool overnight, the white precipitate was filtered off to give crude (wet) of 1-(5-hydroxy-3-methyl-1-phenyl-1H-pyrazol-4-yl)-6-methyl-1,3-dihydro-furo[3,4-c]pyridin-7-ol (23.7 g).

Said crude was suspended in methanol (50 mL) and stirred at 50° C. for 60 minutes in supersonic stirrer, and then residual insoluble matter was filtered off and the filtrate was concentrated to 10 mL, followed by standing to cool at 4° C. in refrigerator overnight to precipitate crystals. Said crystals was filtered off and dried in vacuum desiccator under light interception to give purified crystal of 1-(5-hydroxy-3-methyl-1-phenyl-1H-pyrazol-4-yl)-6-methyl-1,3-dihydro-furo

[3,4-c]pyridin-7-ol (0.22 g). Yield: 6.8%. Appearance: crystal powder, pale yellow white. Melt point: 207-209° C. (browning melting).

Preparation Example 2

Preparation of 1-(5-hydroxy-3-methyl-1-phenyl-1H-pyrazol-4-yl)-6-methyl-1,3-dihydro-furo[3,4-c]pyridin-7-ol hydrochloride

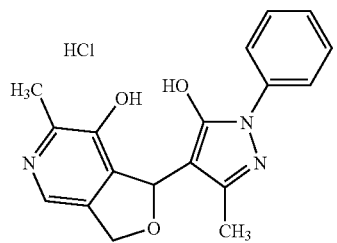

0.5006 g of 1-(5-hydroxy-3-methyl-1-phenyl-1-H-pyrazol-4-yl)-6-methyl-1,3-dihydro-furo[3,4-c]pyridin-7-ol was solved in 150 mL of methanol, and 2N of methanol hydrochloride (1.65 mL) was added and stirred. The solution was concentrated to about 20 mL, and when crystals were precipitate, 50 mL of ethanol was added and concentrated to substitute the crystal solvent, and continued this operation twice and concentrated to about 5 mL. This concentrated solution was stood to cool in refrigerator (4° C.) overnight, the precipitate was filtered off and dried in vacuum desiccator to give 1-(5-hydroxy-3-methyl-1-phenyl-1-H-pyrazol-4-yl)-6-methyl-1,3-dihydro-furo[3,4-c]pyridin-7-ol hydrochloride (0.5011 g). Yield 90.0%. Appearance: crystal powder, pale yellow white. Melting point: 247-249° C. (browning melt).

Test Example 1

Examination of the Pentosidine Formation Inhibiting Effect

For 1-(5-hydroxy-3-methyl-1-phenyl-1H-pyrazol-4-yl)-6-methyl-1,3-dihydro-furo[3,4-c]pyridin-7-ol (hereinafter, referred to "TM-2002"), the pentosidine, which is a typical AGEs, formation inhibiting effect was examined.

Fresh heparinized plasma samples were obtained after informed consent from hemodialysis patients prior to the dialysis session, and filtrated and sterilized. To the plasma (450 μL), there was added the solution of TM-2002 in dimethylsurphoxide (50 μL) (final concentration: 0.8, 2.0, 5.0 mM) incubated at 37° C. for one week. Then, the amount of pentosidine was measured.

Measurement of the amount of pentosidine was made as follows: to each incubated sample (50 μL) was added an equal volume of 10% trichloroacetic acid, followed by centrifugation at 5000 g for 5 minutes; after removal of the supernatant, the pellet was washed by 5% trichloroacetic acid (300 μL); the pellet was dried under reduced pressure and then subjected to hydrolysis in 6N HCl solution (100 μL) at 110° C. under nitrogen atmosphere for 16 hours; to the hydrolysate, 5N NaOH (100 μL) and 0.5 M phosphate buffer (pH 7.4) (200 μL) were added, followed by filtration through a porefilter with a pore size of 0.5 μm and dilution with PBS. The concentration of free pentosidine was determined by reversed-phase HPLC using a fluorescence detector (Miyata, T. et al.: Proc. Natl. Acad. Sci. USA, Vol. 93, p. 2353-2358, 1996). The effluent was monitored at 335/385 nm of excitation/emission wavelength. Synthetic pentosidine was used as the standard. The detection limit of pentosidine was 0.1 pmol/mg protein.

The inhibiting effect was estimated by comparing with positive control (pyridoxamine (Sigma)) reacted in the same manner as TM-2002. In addition, the inhibiting effects of aminoguanidine, olmesartan and edaravone were measured in the same manner. The result (the amount of pentosidine nmol/ml) was shown in FIG. 1 (In the figure, the term "control" means negative control as only solvent. Hereinafter, as same). It is understood from this result that TM-2002 inhibits significantly pentosidine formation compared to pyridoxamine as positive control.

Test Example 2

Phenylalanine Hydroxylation Inhibiting Effect with Hydroxy Radical

Phenylalanine (final concentration: 1 mM), TM-2002 (final concentration: 0.1, 0.5, 2.5 mM), hydrogen peroxide (final concentration: 5 mM) and cupric sulfate (final concentration: 0.1 mM) were dissolved in 200 mM of phosphate buffer (pH7.4) (total volume 500 μL), followed by incubation at 37° C. for 4 hours. Then, DTPA (final concentration: 1 mM) and 260 unit of catalase were added thereto to interrupt the reaction. The amounts of o-tyrosine and m-tyrosine formed were determined by HPLC in the following manner: after a predefined time, the reaction mixture was diluted to 100 folds; 20 μL of the dilution was injected onto HPLC, separation was made with C18 column (4.6×250 mm, 5 μm; Nomura Kagaku) and detection was effected using a fluorescence detector (RF-10A: Shimazu Seisakusho) under the condition of an excitation wavelength of 275 nm and a fluorescence wavelength of 305 nm. In the mobile phase, the flow rate was 0.6 mL/min and the concentration of buffer B was varied from 6.5% to 10% in 25 minutes (buffer A: 0.10% trifluoroacetic acid; buffer B: 80% acetonitrile containing 0.08% trifluoroacetic acid). The result is shown in FIGS. 2 and 3 with the result of aminoguanidine, pyridoxamine and olmesartan.

Test Example 3

The Suppressing Effect on the Nitration of Tyrosine with Peroxynitrite

According to the method of Pannala, A. S. et al. (Free Radic. Biol. Med., 24:594-606, 1998), the examination was carried out. Namely, tyrosine (final concentration: 100 μM), TM-2002 (final concentration: 0.1, 0.5, 2.5 and 5 mM) and peroxynitrite (Dojin Kagaku) (final concentration: 500 μM) were dissolved in 200 mM of phosphate buffer (pH7.4) (liquid volume 500 μL) and incubated at 37° C. for 15 minutes. After incubation, the nitrotyrosine formation was determined with HPLC in the following manner: after a predefined time, the reaction mixture (20 μL) was injected onto HPLC, separation was made with C18 column (4.6×250 mm, 5 μm: Waters) and the detection was effected using a ultraviolet detector (RF-10A: Shimazu Seisakusho) at a wavelength of 280 nm. In the mobile phase, the flow rate was 0.6 mL/min and the concentration of buffer B was varied from 5.0% to 30% in 30 minutes (buffer A: 0.10% trifluoroacetic acid; buffer B: 80% acetonitrile containing 0.08% trifluoroacetic acid). 4-Hydroxy-3-nitrobenzoic acid (100 μM) was used as the internal standard. The result is shown in FIG. 4 with the result of aminoguanidine, pyridoxamine and olmesartan.

Test Example 4

The plasma from patients was substituted to BSA and arabinose, and the pentosidine production inhibiting effect of another compounds (I) or (II) was measured in the same manner as [Test Examination 1]. The result is shown in Table 1. Therein, "-" means that the examination was not carried out.

TABLE 1

| NO | Chemical name | Chemical structure | Pentosidine production rate in 5 mM of medicament (%) |
|---|---|---|---|
| 1 | 2-(3-amino-5-oxo-1-phenyl-4,5-hydro-1H-pyrazol-4-yl)-2-oxo-N-phenyl-acetamide | 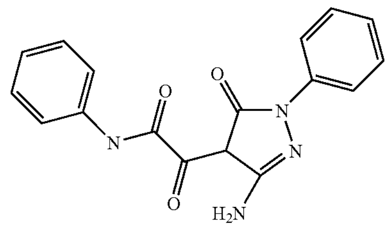 | — |
| 2 | 2-(3-amino-5-oxo-1-phenyl-4,5-hydro-1H-pyrazol-4-yl)-2-oxo-N-thiazol-2-yl-acetamide | 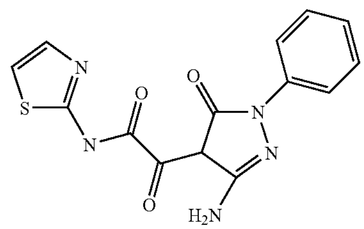 | — |
| 3 | 2-(3-amino-5-oxo-1-phenyl-4,5-hydro-1H-pyrazol-4-yl)-2-oxo-acetamide | 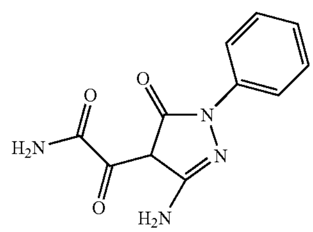 | — |
| 4 | 2-(3-amino-5-oxo-1-phenyl-4,5-hydro-1H-pyrazol-4-yl)-N-(3,4-dimethyl-phenyl)-4-oxo-butylamide | 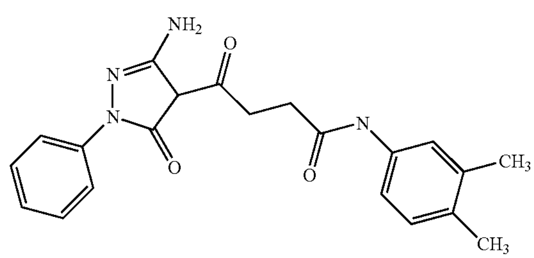 | — |
| 5 | 2-(4-amino-phenyl)-4-(2-hydroxy-ethyl)-5-methyl-2,4-hydro-pyrazol-3-one | 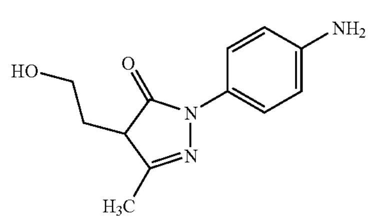 | — |
| 6 | 5-amino-2-phenyl-4-(1-phenyl-1H-tetrazol-5-yl-sulfanil)-2,4-dihydro-pyrazol-3-one | 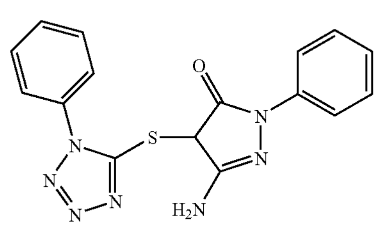 | — |

TABLE 1-continued

| NO | Chemical name | Chemical structure | Pentosidine production rate in 5 mM of medicament (%) |
|---|---|---|---|
| 7 | 3-(3-methyl-5-oxo-1-penyl-4,5-dihydro-1H-pyrazol-4-yl)-propionic acid | 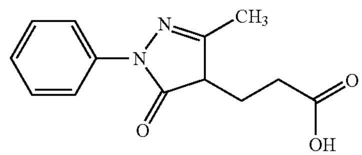 | 64.64 |
| 8 | N-(3-methyl-5-oxo-1-phenyl-4,5-dihydro-1H-pyrazol-4-yl)-acetamide | 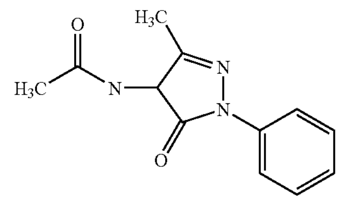 | — |
| 9 | 4-[(5-hydroxy-3-methyl-1-phenyl-1H-pyrazol-4-yl)-phenyl-methyl]-5-methyl-2-phenyl-2,4-dihydro-pyrazol-3-one | 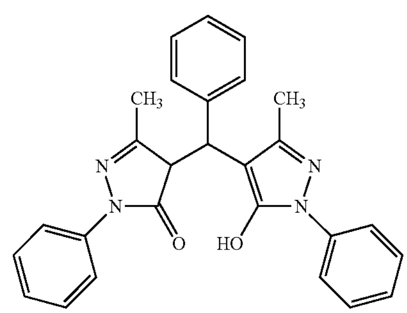 | 7.52 |
| 10 | 2-phenyl-3a,4,5,6-tetrahydro-2H-cycropentapyrazol-3-one | 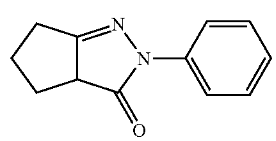 | — |
| 11 | 4-methyl-N-(3-methyl-5-oxo-1-phenyl-4,5-dihydro-1H-pyrazol-4-yl)-benzenesulfonamide | 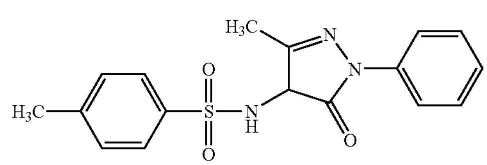 | — |
| 12 | N-(3-methyl-5-oxo-1-phenyl-4,5-dihydro-1H-pyrazol-4-yl)-acetamide | 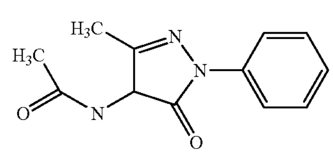 | 54.21 |
| 13 | 5-methyl-2-(3-nitro-phenyl)-4-(1-phenyl-1H-tetrazol-5-yl-sulfanil)-2,4-dihydro-pyrazol-3-one | 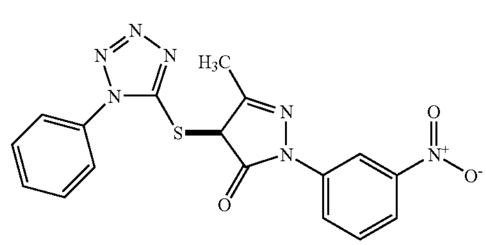 | 74.66 |

TABLE 1-continued

| NO | Chemical name | Chemical structure | Pentosidine production rate in 5 mM of medicament (%) |
|----|---------------|--------------------|-----|
| 14 | N-[5-oxo-1-phenyl-4-(1-phenyl-1H-tetrazol-5-yl-sulfanil)-4,5-dihydro-1H-pyrazol-3-yl]-benzamide | 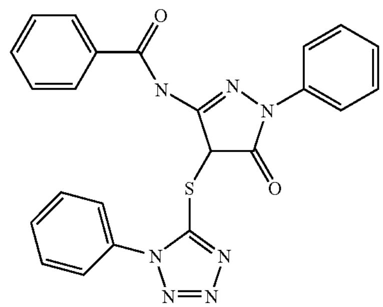 | 61.27 |
| 15 | 4-(hydroxy-phenyl-methyl)-2-phenyl-5-trifluoromethyl-2,4-dihydro-pyrazol-3-one | 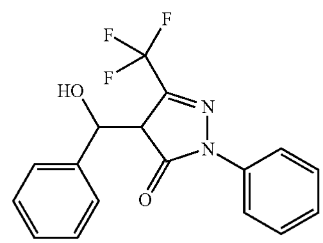 | — |
| 16 | 4-(1-hydroxylmino-ethyl)-2,5-diphenyl-2,4-dihydro-pyrazol-3-one | 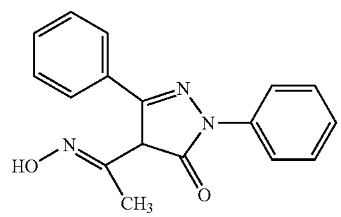 | — |
| 17 | 5,5'-dimethyl-2,2'-diphenyl-2,4,2',4'-tetrahydro-[4,4']-bipyrazol-3,3'-dione | 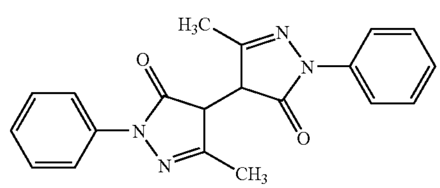 | 60.96 |
| 18 | 2-(4-chloro-phenyl)-4-ethyl-5-methyl-2,4-dihydro-pyrazol-3-one | 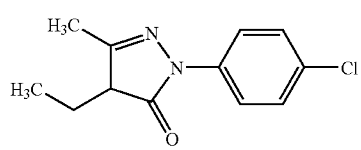 | — |
| 19 | 4-[4-(4-methoxy-phenyl)-thiazole-2-yl-sulfanil]-5-methyl-2-phenyl-2,4-dihydro-pyrazol-3-one | 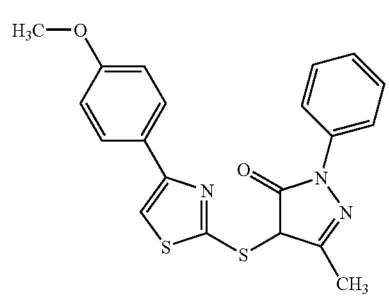 | 40.19 |

TABLE 1-continued

| NO | Chemical name | Chemical structure | Pentosidine production rate in 5 mM of medicament (%) |
|---|---|---|---|
| 20 | 4-(2-oxo-2-phenyl-ethyl)-2-phenyl-5-propyl-2,4-dihydro-pyrazol-3-one | 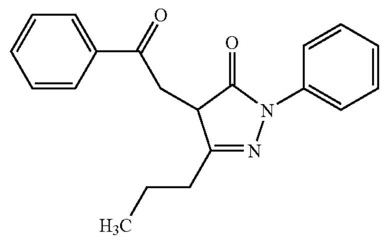 | 83.12 |
| 21 | 5-methyl-2-phenyl-4-(4-p-toluyl-thiazole-2-yl-sulfanil)-2,4-dihydro-pyrazol-3-one | 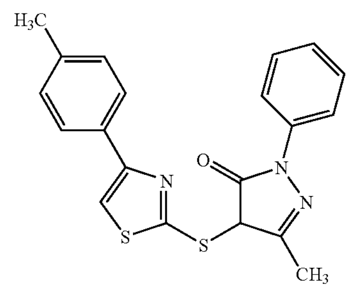 | 42.07 |
| 22 | 2-(4-fluoro-phenyl)-4-[[1-(4-fluoro-phenyl)-5-hydroxy-3-methyl-1H-pyrazol-4-yl]-(2-hydroxy-phenyl)-methyl]-5-methyl-2,4-dihydro-pyrazol-3-one | 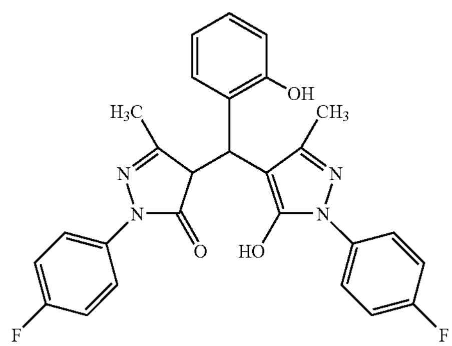 | 2.9 |
| 23 | N-(3,4-dimethyl-phenyl)-2-(3-methyl-5-oxo-1-phenyl-4,5-dihydro-1H-pyrazol-4-yl)-2-oxo-acetamide | 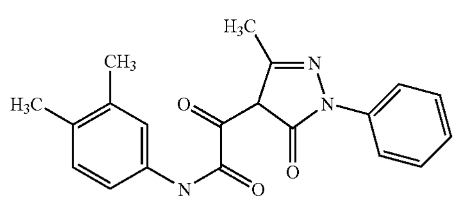 | — |
| 24 | 5-(4-chloro-benzoyl)-4,4-dihydroxy-2-phenyl-2,4-dihydro-pyrazol-3-one | 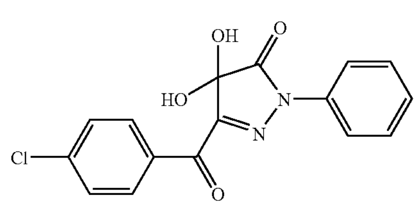 | — |
| 25 | sodium; 4-hydroxy-3-methyl-5-oxo-1-phenyl-4,5-dihydro-1H-pyrazol-4-sulfonate | 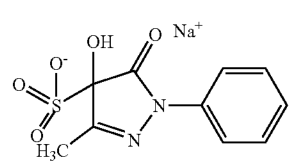 | 38.80 |

TABLE 1-continued

| NO | Chemical name | Chemical structure | Pentosidine production rate in 5 mM of medicament (%) |
|----|---------------|--------------------|---|
| 26 | 5-methyl-4,4-di-morpholin-4-yl-2-phenyl-2,4-dihydro-pyrazol-3-one | 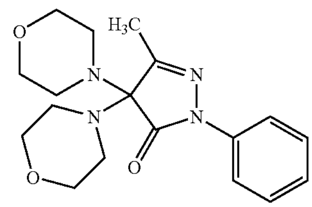 | 50.68 |
| 27 | sodium 3-benzoylamino-4-hydroxy-5-oxo-1-phenyl-4,5-dihydro-1H-pyrazol-4-sulfonate | 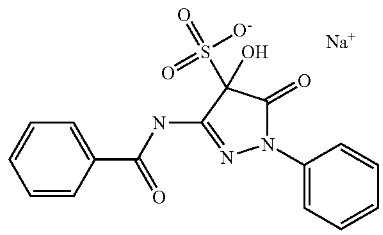 | 2.83 |
| 28 | 3-methyl-1-phenyl-5-oxo-4-spiro-(3-oxo-2,3-dihydro-benzo[b]thiophen-2-yl)-4,5-dihydro-1H-pyrazol | 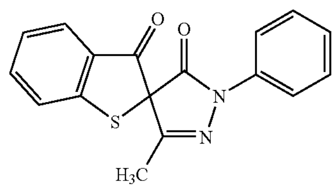 | 22.83 |
| 29 | 4,4,5-trimethyl-2-phenyl-2,4-dihydro-pyrazol-3-one | 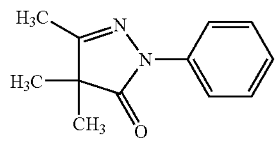 | — |
| 30 | 4,10-dimethyl-2,8,11-triphenyl-2,3,8,9-tetraza-dispiro[4.0.4.1]undeca-3,9-diene-1,7-dione | 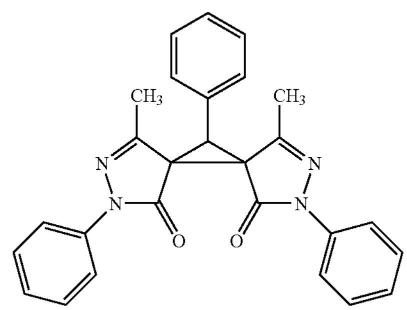 | 62.43 |
| 31 | 2-(2-chloro-phenyl)-4-(3-ethoxy-4-hydroxy-benzylidene)-5-methyl-2,4-dihydro-pyrazol-3-one | 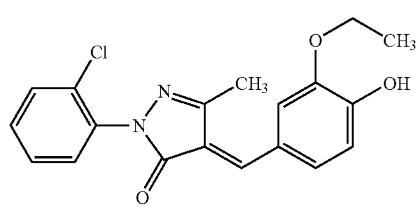 | 15.57 |
| 32 | 2-(2-chloro-phenyl)-4-(4-dimethylamino-benzylidene)-5-methyl-2,4-dihydro-pyrazol-3-one | 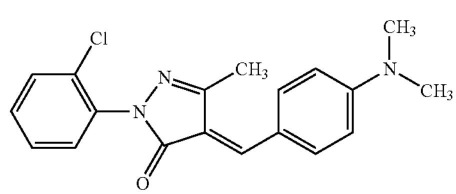 | 8.7 |

TABLE 1-continued

| NO | Chemical name | Chemical structure | Pentosidine production rate in 5 mM of medicament (%) |
|----|---------------|--------------------|---|
| 33 | 5-methyl-4-(3-phenyl-allylidene)-2-(3-trifluoromethyl-phenyl)-2,4-dihydro-pyrazol-3-one | 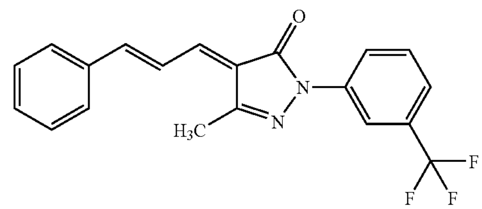 | 80.08 |
| 34 | 3-{5-[3-methyl-5-oxo-1-(4-sulfamoyl-phenyl)-1,5-dihydro-pyrazol-4-ylidene-methyl]-furan-2-yl}-benzoic acid | 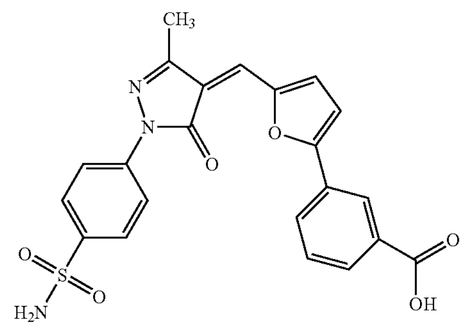 | — |
| 35 | 4-(4-dimethylamino-benzylidene)-2-(3-fluoro-phenyl)-5-methyl-2,4-dihydro-pyrazol-3-one | 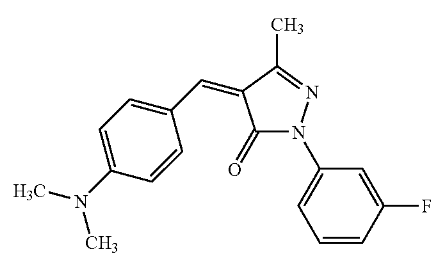 | 76.31 |
| 36 | 3-{4-[4-(3-chloro-4,5-dihydro-pyrazol-1-yl)-benzylidene]-3-methyl-5-oxo-4,5-dihydro-pyrazol-1-yl}-benzoic acid | 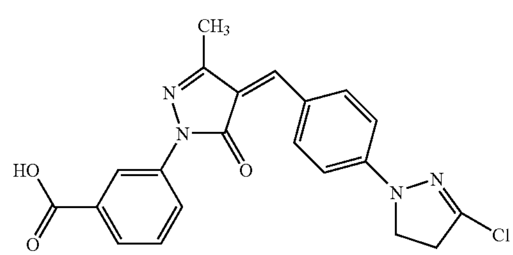 | 26.37 |
| 37 | 3-[4-(2-hydroxy-benzylidene)-5-oxo-3-phenyl-4,5-dihydro-pyrazol-1-yl]-benzoic acid | 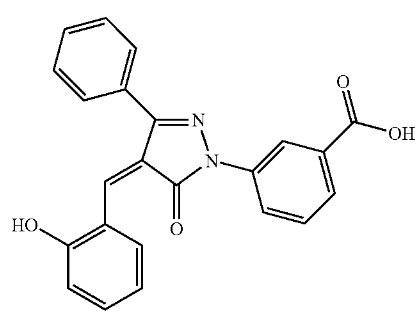 | 0.02 |

TABLE 1-continued

| NO | Chemical name | Chemical structure | Pentosidine production rate in 5 mM of medicament (%) |
|---|---|---|---|
| 38 | 3-[1-(3-chloro-phenyl)-3-methyl-5-oxo-1,5-dihydro-pyrazol-4-ylidene-methyl]-1H-quinolin-2-one | 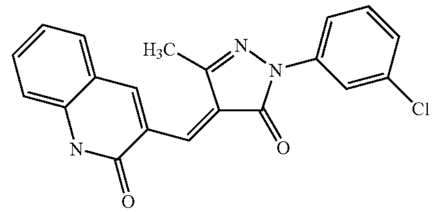 | 84.95 |
| 39 | 3-{5-[3-methyl-5-oxo-1-(4-sulfamoyl-phenyl)-1,5-dihydro-pyrazol-4-ylidene-methyl]-furan-2-yl}-benzoic acid-methyl ester | 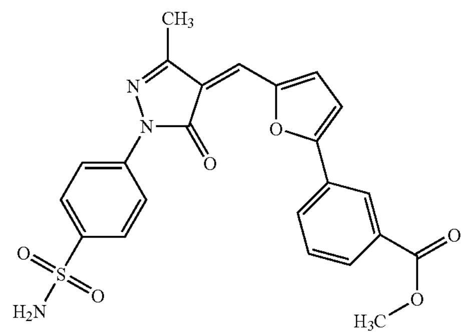 | 16.87 |
| 40 | 4-(4-benzo[1,3]dioxol-5-ylmethylene-3-methyl-5-oxo-4,5-dihydro-pyrazol-1-yl)-benzoic acid-methyl ester | 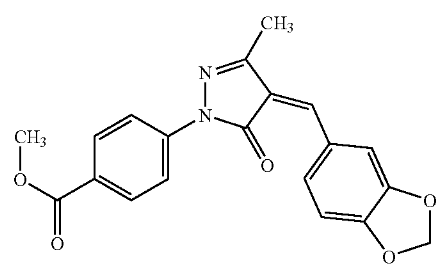 | 32.37 |
| 41 | 4-{3-methyl-5-oxo-4-[5-(4-sulfamoyl-phenyl)-furan-2-yl-methylene]-4,5-dihydro-pyrazol-1-yl}-benzoic acid-methyl ester | 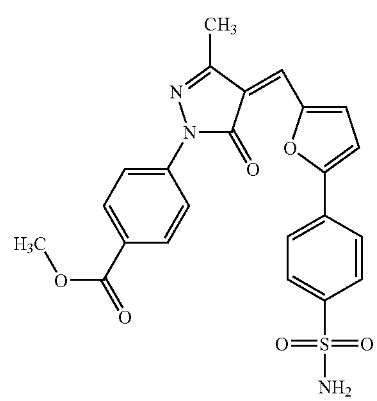 | 37.81 |
| 42 | 2-(4-chloro-phenyl)-4-(2,4-dihydroxy-benzylidene)-5-methyl-2,4-dihydro-pyrazol-3-one | 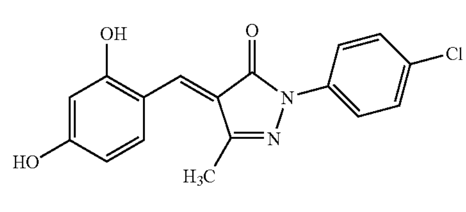 | 68.32 |

TABLE 1-continued

| NO | Chemical name | Chemical structure | Pentosidine production rate in 5 mM of medicament (%) |
|----|---------------|--------------------|-------------------------------------------------------|
| 43 | 2-(4-chloro-phenyl)-4-(3-hydroxy-benzylidene)-5-methyl-2,4-dihydropyrazol-3-one | 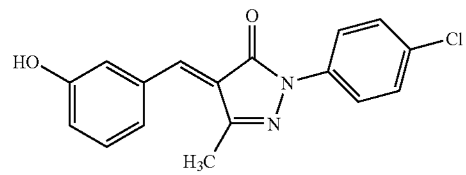 | 3.00 |
| 44 | 4-(3,4-dihydroxy-benzylidene)-5-methyl-2-p-toluyl-2,4-dihydro-pyrazol-3-one | 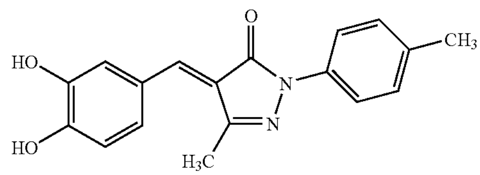 | 66.19 |
| 45 | 3-[1-(4-acetyl-phenyl)-3-methyl-5-oxo-1,5-dihydro-pyrazol-4-ylidene]-1,3-dihydro-indol-2-one | 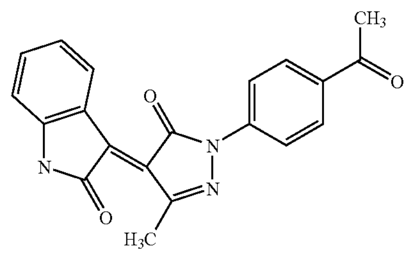 | 19.22 |
| 46 | 2-(4-fluoro-phenyl)-4-(5-hydroxy-3-methyl-1-o-toluyl-1H-pyrazol-4-yl-methylene)-5-methyl-2,4-dihydro-pyrazol-3-one | 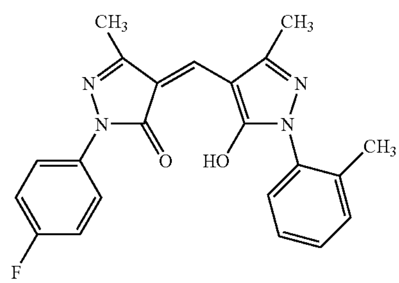 | 15.69 |
| 47 | 2-(4-chloro-phenyl)-4-(4-hydroxy-3-methoxy-benzylidene)-5-trifluoromethyl-2,4-dihydro-pyrazol-3-one | 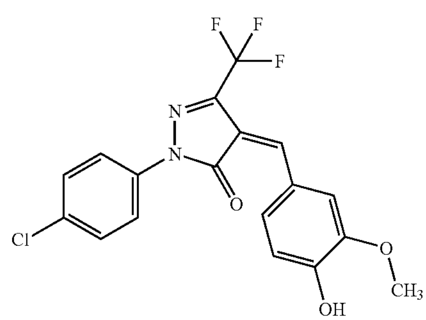 | 28.86 |
| 48 | 2-(4-ethyl-phenyl)-4-(4-hydroxy-benzylidene)-5-methyl-2,4-dihydro-pyrazol-3-one | 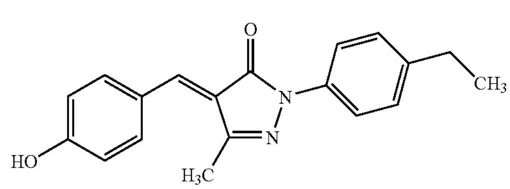 | 0.02 |

TABLE 1-continued

| NO | Chemical name | Chemical structure | Pentosidine production rate in 5 mM of medicament (%) |
|---|---|---|---|
| 49 | 4-[4-(4-hydroxy-benzylidene)-3-methyl-5-oxo-4,5-dihydro-pyrazol-1-yl]-benzenesulfonamide | 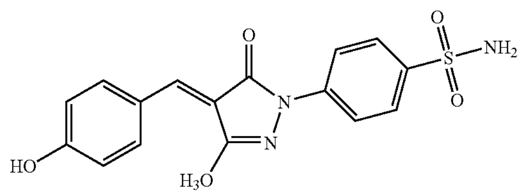 | 7.09 |
| 50 | 4-(5-oxo-4-thiophene-2-yl-methylene-3-trifluoromethyl-4,5-dihydro-pyrazol-1-yl)-benzoic acid-ethyl ester | 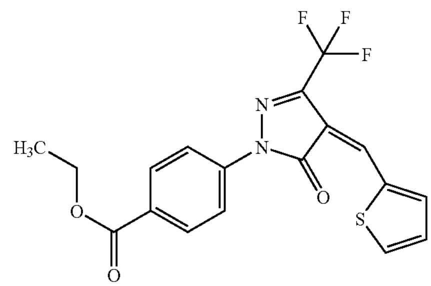 | 63.17 |
| 51 | 4-[4-(4-dimethylamino-benzylidene)-5-oxo-3-trifluoromethyl-4,5-dihydro-pyrazole-1-yl]-benzenesulfonamide | 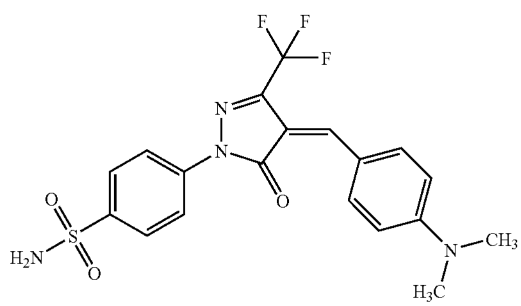 | 41.68 |
| 52 | 4-isopropylidene-5-methyl-2-phenyl-2,4-dihydro-pyrazol-3-one | 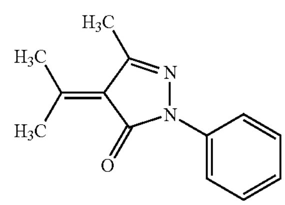 | — |
| 53 | 4-(4-hydroxy-benzylidene)-2-phenyl-5-trifluoromethyl-2,4-dihydro-pyrazol-3-one | 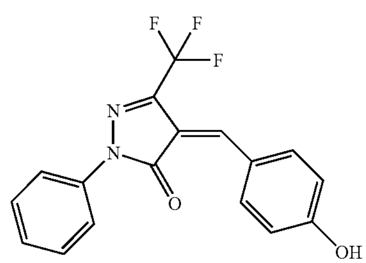 | 66.76 |
| 54 | 4-(2,4-dihydroxy-benzylidene)-2-(3,4-dimethyl-phenyl)-5-methyl-2,4-dihydro-pyrazol-3-one | 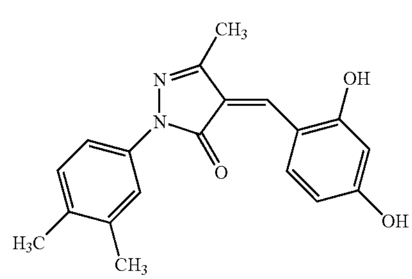 | 73.48 |

TABLE 1-continued

| NO | Chemical name | Chemical structure | Pentosidine production rate in 5 mM of medicament (%) |
|---|---|---|---|
| 55 | 3-[4-(3-ethoxy-4-hydroxy-benzylidene)-3-methyl-5-oxo-4,5-dihydro-pyrazol-1-yl]-benzoic acid | 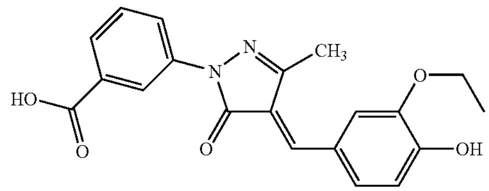 | — |
| 56 | 4-[4-(3,5-di-tert-butyl-4-hydroxy-benzylidene)-3-methyl-5-oxo-4,5-dihydro-pyrazol-1-yl]-benzoic acid | 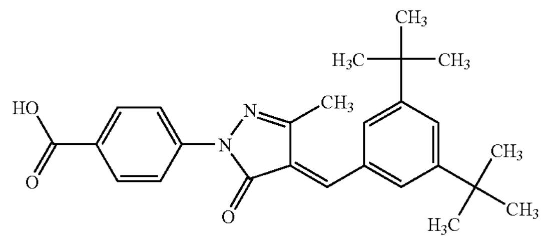 | — |
| 57 | 3-[3-(4-hydroxy-3-methoxy-benzylidene)-3-methyl-5-oxo-4,5-dihydro-pyrazol-1-yl]-benzoic acid | 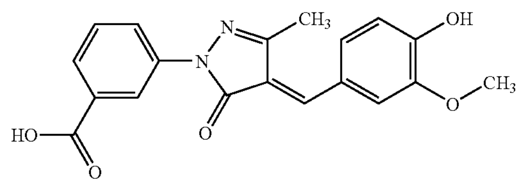 | — |
| 58 | 3-[3-hydroxy-4-(4-hydroxy-3-methoxy-benzylidene)-5-oxo-pyrazolidin-1-yl]-benzoic acid | 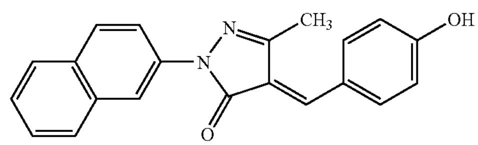 | 0.07 |
| 59 | 4-(3-hydroxy-2,4-dimethoxy-benzylidene)-5-methyl-2-phenyl-2,4-dihydro-pyrazol-3-one | 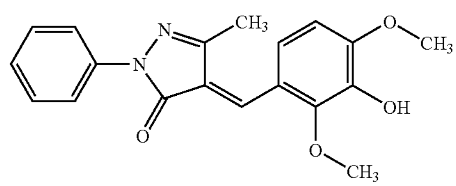 | 5.3 |
| 60 | 4-[4-(4-hydroxy-3-methoxy-benzylidene)-3-methyl-5-oxo-pyrazolidin-1-yl]-benzoic acid-isopropyl ester | 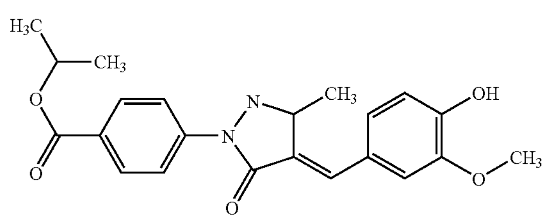 | 9.02 |
| 61 | 2-chloro-5-[4-(2-chloro-4-hydroxy-5-methoxy-benzylidene)-3-methyl-5-oxo-4,5-dihydro-pyrazol-1-yl]-benzoic acid | 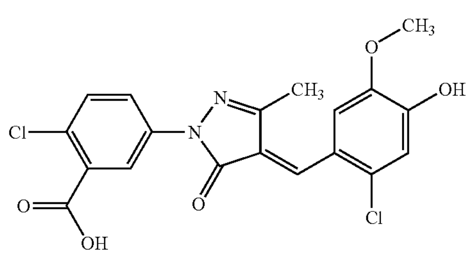 | 46.25 |

TABLE 1-continued

| NO | Chemical name | Chemical structure | Pentosidine production rate in 5 mM of medicament (%) |
|---|---|---|---|
| 62 | 4-[4-(4-hydroxy-benzylidene)-3-methyl-5-oxo-4,5-dihydro-pyrazol-1-yl]-benzoic acid-ethyl ester | 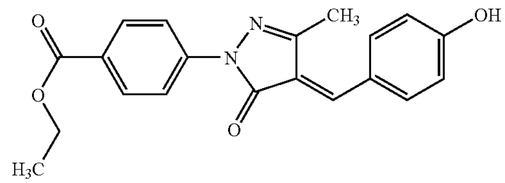 | — |
| 63 | 4-[4-(4-hydroxy-benzylidene)-5-oxo-3-trifluoromethyl-4,5-dihydro-pyrazol-1-yl]-benzoic acid-ethyl ester | 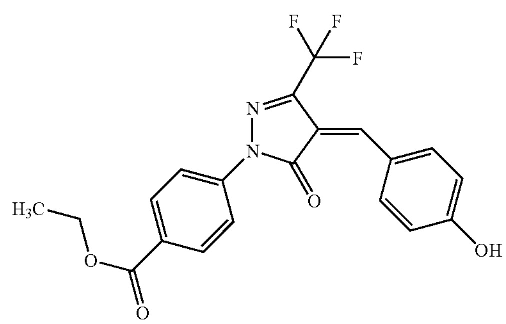 | — |
| 64 | 4-[4-(4-hydroxy-benzylidene)-3-methyl-5-oxo-4,5-dihydro-pyrazol-1-yl]-benzoic acid | 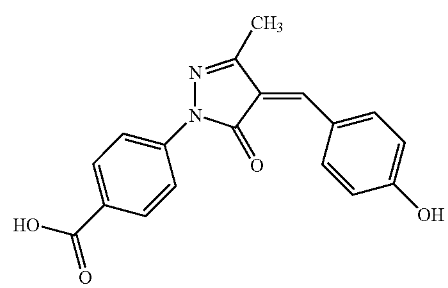 | — |
| 65 | 4-dimethylaminomethylene-5-methyl-2-phenyl-2,4-dihydro-pyrazol-3-one | 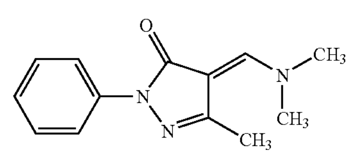 | 62.43 |
| 66 | 4-(5-hydroxy-3-methyl-1-phenyl-1H-pyrazol-4-yl-methylene)-5-methyl-2-phenyl-2,4-dihydro-pyrazol-3-one | 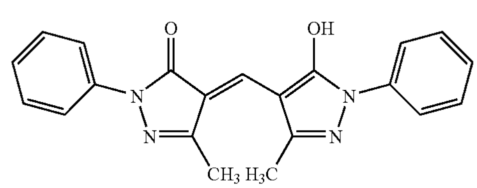 | 15.17 |
| 67 | 4-(4-chloro-benzylidene)-5-methyl-2-phenyl-2,4-dihydro-pyrazol-3-one | 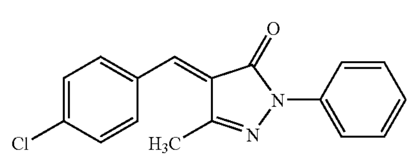 | 9.09 |

TABLE 1-continued

| NO | Chemical name | Chemical structure | Pentosidine production rate in 5 mM of medicament (%) |
|----|---------------|--------------------|----|
| 68 | 1-(5-hydroxy-3-methyl-1-phenyl-1H-pyrazol-4-yl)-6-methyl-1,3-dihydro-furo[3,4-c]pyridin-7-ol | 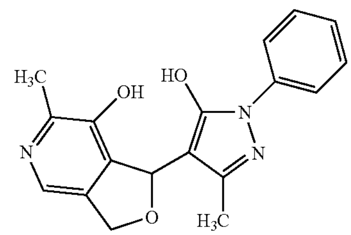 | 2.82 |
| 69 | 1-(5-hydroxy-3-methyl-1-phenyl-1H-pyrazol-4-yl)-6-methyl-1,3-dihydro-furo[3,4-c]pyridin-7-ol (hydrochloric acid salt) | 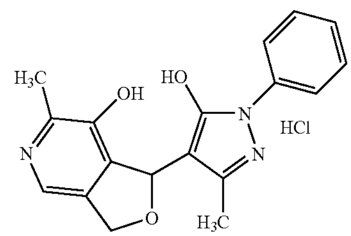 | 2.94 |
| 70 | 4-(4-hydroxy-benzylidene)-5-methyl-2-phenyl-2,4-dihydro-pyrazol-3-one | 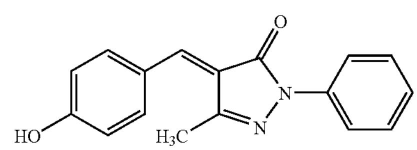 | 0.04 |
| 71 | 2-(3-chloro-phenyl)-4-(4-hydroxy-benzylidene)-5-methyl-2,4-dihydropyrazol-3-one | 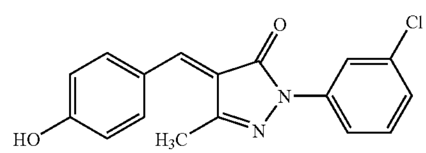 | 4.63 |
| 72 | 4-(4-benzyloxy-benzylidene)-5-methyl-2-phenyl-2,4-dihydropyrazol-3-one | 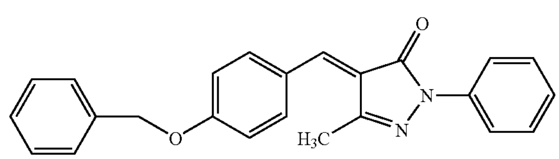 | 7.63 |
| 73 | 2-(3-chloro-phenyl)-5-methyl-2H-pyrazol-3,4-dione 4-oxym | 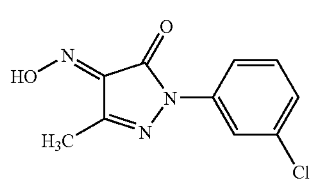 | 66.42 |
| 74 | 5-(5-oxo-1,3-diphenyl-1,5-dihydro-pyrazol-4-ylidene)-4-phenyl-4,5-dihydro-[1,3,4]thiazole-2-carboxilic acid-ethyl este | 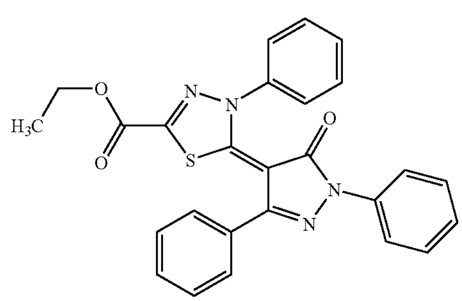 | 87.24 |

TABLE 1-continued

| NO | Chemical name | Chemical structure | Pentosidine production rate in 5 mM of medicament (%) |
|----|---------------|--------------------|-----|
| 75 | 4-[1,3]dithioran-2-ylidene-5-methyl-2-phenyl-2,4-dihydro-pyrazol-3-one | 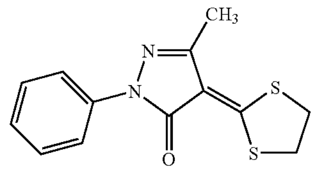 | — |
| 76 | 5-(4-chloro-phenylsulfanilmethyl)-2-phenyl-4-[N'-(3-trifluoromethyl-phenyl)-hydrozino]-2,4-dihydro-pyrazol-3-on | 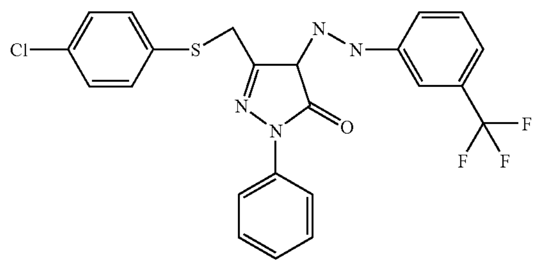 | — |
| 77 | 4-(5-benzoyl-3-phenyl-3H-[1,3,4]thiadiazol-2-ylidene)-2,5-diphenyl-2,4-dihydro-pyrazol-3-one | 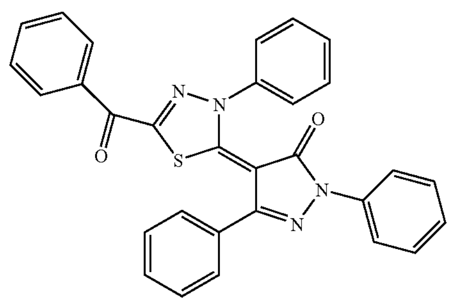 | — |
| 78 | phosphoric acid mono-[5-hydroxy-6-methyl-4-(3-methyl-5-oxo-1-phenyl-1,5-dihydro-pyrazol-4-ylidene-methyl)-pyridin-3-yl-methyl]ester | 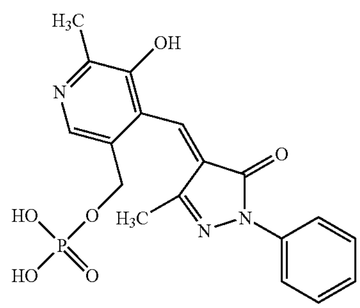 | — |

Test Example 5

Examination with Balloon Injury Model vascular endothelial thickening inhibiting effect in rat carotid balloon injury model, which is post-vasodilatory operation restenosis model.

TM-2002 was suspended in sodium carboxymethylcellulose aqueous solution (CMC) (0.5%) using mortar and prepared to the concentration of 12.5 mg/mL using measuring cylinder.

Aminoguanidine hydrochloride (Sigma) was used as positive control, suspended in CMC aqueous solution (0.5%) using mortar in the same manner, and prepare to the concentration of 11.25 mg/mL using measuring cylinder. Each preparation was formed when use it to administer orally coercively using disposable injection and oral sonde with suspending.

The vehicle group (n=10) were administered CMC aqueous solution (0.5%) of 4 mL/kg/once, twice a daily (8 mL/kg/day). TM-2002 (test compound) group (n=10) were orally administered 50mg/kg/once of 1-(5-hydroxy-3-methyl-1-phenyl-1H-pyrazol-4-yl)-6-methyl-1,3-dihydro-furo[3,4-c]pyridin-7-ol hydrochloride, twice a daily (100 mg/kg/day). The aminoguanidine group (n=10) were orally administered 45 mg/kg/once of aminoguanidine hydrochloride, twice a daily (90 mg/kg/day).

The administration was started the day before balloon injury, and carried out 15 days (from injury day as 1 day to 14 day), morning and evening, twice a daily, with more than 6 hours intervals (15 day after balloon injury, dissection was carried out; no administration on 15 day).

9 weeks aged (when balloon injury, 10 weeks aged) SD line male rats (Japan SLC) were used. When we got the test animals, the health condition of each animals were checked by the naked eye and healthy animals were caged. After 6 days from coming as preparative breeding, good health individuals were subjected to the examination. 1 group involves 10 rats, and the rats were divided into 3 groups, i.e. vehicle, test compound, aminoguanidine group, depending on their body weight before administration.

The neck and femoral region of rats were incised under anesthesia by pentobarbital sodium (40 mg/kg, i.p.), left carotid and arteria femoralis were exposed the arteria femoralis was incised and inserted balloon catheter (2Fr, fogaty catheter; Baxter), and then the tip was leaded to internal-external carotid branch of left carotid. The appearance of balloon catheter in the carotid was confirmed by the naked eye, then the balloon puffed by injection of air (0.3 mL). While puffing the balloon, the balloon catheter was drawn forth to aortic arches. This operation was continued third and injured intima of the vessel. After drown of balloon catheter, arteria femoralis was tied up. The incision site was sutured and the wound was mundified using iodine solution. The right carotid without injury was used as control of each individuals.

While testing, the alive and the condition of wound were observed everyday. The body weight was measured once a day from the day before injury to 14 day after balloon injury. The dose of each individuals were calculated by their body weight.

The blood samples were obtained from abdomen vena cava under anesthesia by ether on 15 day after balloon injury. After blood collection, left carotid was removed and divided 3 sections. The 5 mm slice from each sections was obtained, right carotid was removed and picked out about 5 mm slice from its center area, and each of them were fixed with 10% neutral buffered formalin. The fixed samples were prepared to paraffin block, followed by thin slice and sustained with HE. The area of intravascular lumen, the area surrounded by internal elastic lamina and the area surrounded by external elastic lamina was calculated using image analyzer (VM-30, Olympus photology).

For each sections (3 region), the area of neointimal, media and neointimal/media rate of blood vessel was calculated from the measured area. The intimal thickening was estimated using the average of 3 region from each individuals. The result is shown in FIG. 5 (A, B and C). It is understood from this result that TM-2002 group represents intimal thickening inhibiting effect equal to aminoguanidine group as positive control.

Test Example 6

Reactivity with Vitamin B6

Vitamin B6 (pyridoxal-5'-phosphate) (50µM) and TM-2002 (0.5 µM) was incubated in phosphate buffered saline (PBS), at 37° C. . The concentration of residual pyridoxal-5'-phosphate was determined with HPLC to measure the kinetics between 0 to 20 hours in the following manner: after a designed period of time, the reaction mixture (10 µL) was injected onto HPLC, separation was made with Purecil C18 column (4.6×250 mm, 5 µm: Waters) and detection was effected using a fluorescence detector (RF-10A; Shimazu Seisakusho; excitation wavelength, 300 nm and fluorescence wavelength, 400 nm). In the mobile phase, the flow rate was 0.6 ml/L and the concentration of buffer B was varied from 0% to 3% in 25 minutes (buffer A: 0.10% trifluoroacetic acid; buffer B: 80% acetonitrile containing 0.08% trifluoroacetic acid). Aminoguanidine, which is known its vitamin B6 capturing effect was used as control.

After 20 hours, while pyridoxal-5'-phosphate residual rate of TM-2002 group was 97%, pyridoxal-5'-phosphate residual rate of aminoguanidine as control was only 0.2%. Accordingly, it is shown that TM-2002 does not react with vitamin B6.

In addition, another compounds (I) and (II) showed the same result as TM-2002.

Test Example 7

Vitamin B6 Deficiency Inhibiting Effect

TM-2002 was administered to normal rat (WKY rat: Japan SLC) to examine the presence of vitamin B6 deficiency. Aminoguanidine, which is known its vitamin B6 capturing effect was used as control. Each group involves 10 rats. 13 mg/kg/rat/once of TM-2002 or aminoguanidine suspended in carboxymethyl cellulose (0.5%) was respectively administered coercively using sonde twice a daily. Administration term was 20 weeks. The conventional diet (CRF1: Oriental yeast) was used.

After 20 weeks, the appearance of WKY rat was observed. In TM-2002 group, condition caused by vitamin B6 deficiency such as angular cheilitis, mouth inflammation, glossitis, chelitis, acute and chronic eczema, contact dermatitis, peripheral neuritis, anemia, hypolymphemia and nerve disorder were not observed. On the other hand, in aminoguanidine group, skin inflammation, epilepsy and convulsion caused by cerebral disorder were observed.

In addition, another compounds (I) and (II) showed the same result as TM-2002.

Test Example 8

Renal Protecting Effect in SHR/NDmcr-cp Rat and Wistar Kyoto Rat

Renal protecting effect was observed using SHR/NDmcr-cp (Disease Model Cooperative Research Association) rat, which had been known their high blood pressure, hyperglycemia, hyperlipemia, obesity and hyperinsulinemia and renal function disorder while aging.

SHR/NDmcr-cp rat and Wistar Kyoto rat (Disease Model Cooperative Research Association) of 9 weeks aged were conformed for 3 weeks and measured their body weight and blood collection before administration. One group contain five rats (body weight 440 g±32 g). After division, excipient (negative control), positive control compound and test compound were administered 20 weeks. Carboxymethylcellulose (carboxymethyl cellulose Na/ Wako) solution as excipient and olmesartane, which is one of the angiotensin II receptor antagonist and has renal protective effect, as positive control compound were used to examine the effect of TM-2002 (test compound). The dosage of olmesartane was 3 mg per 1 kg of body weight and that of TM-2002 was 50 mg per 1 kg of body weight. Olmesartane was prepared by suspending or solving the designed amount in 1.0 ml of 0.5% carboxymethylcellulose solution or purified water, and TM-2002 was prepared by mixing the designed amount in 30 g of diet (for one day). Since the increase of body weight of test animals was remarkable, the amount of positive control compound and test compound was modified depending on the result of body weight measuring (every week). The dosage route was oral administration of 1 ml of 0.5% carboxymethylcellulose solution of excipients in case negative control, and of designed amount of olmesartane in 0.5% carboxymethylcellulose solution in positive control respectively, using sonde. The dosage route of test compound group is diet with mixed designed amount of TM-2002. The amount of diet is 30 g per daily for every group (excipient group as negative control, positive control compound group and test compound group). While administration period, body weight was measured every week, and blood collection, urine collection and blood pressure measuring were done every 2 weeks before 4 weeks aged and every 4 weeks after 5 weeks aged. Blood collection was carried out after warming to 38° C. by warming plate from caudal vein for 800 μl (heparin treatment: the amount of heparin was determined by ratio 15 μl to 1 ml of blood). The urinary sample was collected using urine metabolizing cage (Japan Clea). The volume of daily urine was measured when urine was collected. The blood pressure was determined with by the tail-cuff method blood pressure measure (Softron).

The blood samples were used to determine glucose level, the concentration of triglyceride, total cholesterol, hemoglobin A1c insulin. The urine samples were used to determine the amount of urinary protein, creatinine and urinary nitrogen. Such examination was asked to Japan SRL and carried out.

The result of such examination for urine protective effect in 33 weeks aged represents that negative control represents high blood pressure, high urinary protein and renal function disorder. In positive control group, since olmesartane is hypotensor, blood pressure lowering, urinary protein suppressing and renal function improving is shown. On the other hand, in test compound group, urinary protein is suppressed remarkably without blood pressure lowering comparing to negative control, and inhibiting effect is stronger than that of positive control, thus, excellent renal protective effect is show. The present invention is expected to the treatment for renal disease without hyper tension, the treatment for renal disease combined with hypotensor without renal protective effect, and synergetic effect together with hypotensor with renal protective affect, thus is useful for medicament for renal disease. The result is represented in FIGS. 7 and 8.

Test Example 9

Renal Protective Effect on Thy-1 Nephritis Model Rat 1.2 mg/kg of OX-7, anti Thy-1 antibody, was administered to wistar rat (male, body weight 150 g, 6 weeks aged) in caudal vein to prepare typical glomerulonephritis model with mesangial nephritis. After the administration of anti Thy-1 antibody, test compound (TM-2002, 50 mg/kg body weight, twice a daily) was suspended in 0.5% carboxymethylcellulose, was coercively administered 5 days continuously using sonde, on sixth day sampled, kidney was obtained, and analysed pathologically (count the number of glomerular cells). In particular, cells were stained by PAS according to conventional method, the stained image was captured by 3CCD camera (Olympus), and then analyzed using softwares, Image Graver PCI (FUJI shashin film) and Mac Aspect (Mitani kabushiki kaisha). Also, biochemical analysis of blood and urine was carried out (contract clinical analysis organization: SRL). As the result, urinary protein and BUN value were improved in TM-2002 group, and the number of glomerular cells, which increase along with disorder, was significantly suppressed (p<0.0001) and the renal protective effect was indicated. The results are indicated in FIGS. 8 to 10.

Test Example 10

Renal Protective Effect on Ischemia-Reperfusion Renal Failure Model Rat

This condition model is typical acute renal failure model. To prepare the model, operated on wistar rats (male, body weight 150 g, 6 weeks aged) to remove right kidney, and on the following day, renal artery of remaining left kidney was apply a ligature with clip under general anesthesia. After the clipping, the rats were on warming plate not to reduce the body temperature and was observed for 45 minutes (ischemia), and then removes the clip to allow re-perfusion. After preparing the ischemia-reperfusion model, test compound (TM-2002, 50 mg/kg body weight, twice a daily) was suspended in 0.5% carboxymethylcellulose. The suspension was coercively administered 2 days continuously using sonde, on third day kidney was obtained, and analysed pathologically (renal tubular stromal disorder score). In particular, the kidney was stained by PAS according to conventional method and the renal tubular stromal disorder was estimated for the presence or absence of renal tubular necrosis, renal tubular hypertrophy, renal tubular atrophia, renal tubular basal lamina thickening and cast in the sustained image of kidney. As well as biochemical analysis of blood was carried out (contract clinical analysis organization: SRL). As the result, urinary protein and BUN value were improved in TM-2002 group, and the number of glomerular cells, which increase along with disorder, was significantly suppressed (p<0.0001) and the renal protective effect was indicated. The results were indicated in FIGS. 11 to 13.

Test Example 11

Cerebroprotective Action in Middle Cerebral Artery Ischemia-Reperfusion Model

CD(SD)IGS male rats (Japan Charles river Kabushiki kaisha, Hino farm, room No. 22, specific product) (8 rats per one group) having body weight 270 to 350 g were anesthetized by 2% isoflurane (mixed bas comprising of 70% $N_2O$ (laughter gas) and 30% $O_2$) to immobilize, and then the rats were put on warming plate to keep the rectal and brain temperature 37 to 38° C. After that, to observe the stability in the examination, cannula which was made by polyethylene (PE-50, Becton Dickinson) was inserted and left in caudal artery of said animal, and this made blood drawing and blood pressure determining to monitor the biochemical parameter such as blood sugar level, hematocrit, $CO_2$ concentration, oxygen partial pressure, pH, blood pressure and etc. In addition, cerebral blood flow in cortex was determined by laser doppler fluorometry (Neuroscience.inc: OMEGA FLOW (FLO-C1)), putting the detection site directly on cranium on the point left 4 mm from bregma. Left neck of such animal was incised, and from internal and external carotid fork of common carotid artery to upstream of internal carotid, nylon surgical thread (length 16 mm, diameter 0.2 to 0.3 mm, with silicon coating on its tip 3 mm) was passed and left, middle cerebral artery was obstructed for 2 hours. After that, the thread was removed to release the middle cerebral artery, and blood was reperfused for 21 hours. To each animals, 3.0 mg/kg of edaravone (control) and 5.58 mg/kg of TM-2002 were respectively administered twice by cannula which is left in caudal artery 5 minutes and 5 hours after middle cerebral artery occlusion. After said operation, the brain was removed from said animal, and after preparing 7 brain slices with 2 mm thickness, to TTC stain (0.8 g of 2,3,5-triphenyltetrazolium chloride (Sigma)

dissolved in 40 ml of saline) were soaked at 37° C. for 15 minutes to stain, the area of infarction and fixed by 10% neutral formalin liquid to prepare specimen. Such specimens were created the image by CCD camera respectively, and analysed according to method of Swanson et al. (J Cereb Blood Flow Metab 10:290-293; 1994). As the result, cerebral infarction nest was significantly reduced by control agent edaravone and test agent TM-2002 comparing to excipient single administration. The result is indicated in FIG. 13. In addition, nervous condition was estimated in the operated rat on horizontal table by grading system according to the method of Bederson et al. (Stroke 17:472-476, 1990) by 4 grades: Grade 0, when push from the side they walk normally without palsy; Grade 1, when push from the side they resist and walk straight to the front with forelimb flexion; Grade 2, when push from the side they do not resist and walk straight to the front; Grade 3, when push from the side they do not resist and cannot walk straight (spin or fall). Furthermore, function recovering was estimated before and after the operation by rotor rod test that estimates how much they can walk on rotating rotor. As the result, improvement for nervous condition and recovering the function were remarkably shown in edaravone (control drug) and TM-2002 (test compound) comparing to excipient single administration. The result is indicated in Table 2.

tion kept clear solution, pH 7.0, pH 8.0 solutions were, however, observed precipitate. In particular, the change of color was shown in pH 7.0 and pH 8.0 solutions. As the result, stable TM-2002 injectable formulation in its solubility may be prepared by keeping acidic condition using inorganic acid such as hydrochloride, sulfuric acid, or various organic acid, or by using TM-2002 hydrochloride or sulfate as material which is made from said acids.

Test Example 13

Examination of Stabilizing Agent

Several kind of stabilizing agent was usually used to stabilize the medicament and the effective manner is addition of antioxidant. Particularly, the material having lower oxidation-reduction potential is effective to stabilize highly oxidized compound. Accordingly, for sodium acid sulfite ($NaHSO_3$) and L-cystein ($C_3H_7O_2S.HCl$), which are usually used in injection, the stability was examined by adding such materials to TM-2002 hydrochloride aqueous solution.

The solving state of TM-2002 hydrochloride solution added sodium acid sulfite was examined in following manner; 1 ml of purified water, sodium acid sulfite (0.5 mg) and

TABLE 2

| Test Name | | Diluent single administration | | Edaravone | | TM-3001 | |
|---|---|---|---|---|---|---|---|
| | | Ave | SD | Ave | SD | Ave | SD |
| Nervous condition estimation test* | | | | | | | |
| after occlusion | 10 min | 2.9 | 0.3 | 2.8 | 0.4 | 2.8 | 0.7 |
| after occlusion | 2 hrs | 2.9 | 0.3 | 2.7 | 0.5 | 2.6 | 1.1 |
| after reperfusion | 10 min | 2.4 | 1.1 | 2.2 | 1.0 | 1.5 | 1.6 |
| after reperfusion | 3 hrs | 2.3 | 1.1 | 2.1 | 1.0 | 1.3 | 1.5 |
| after reperfusion | 4 hrs | 2.3 | 1.1 | 2.0 | 1.2 | 2.0 | 1.4 |
| after reperfusion | 22 hrs | 1.6 | 1.4 | 1.5 | 1.2 | 2.0 | 1.4 |
| rotor rod test** | | | | | | | |
| before occlusion | | 202.7 | 123.0 | 197.0 | 123.4 | 183.4 | 138.0 |
| reperfusion | | 67.1 | 70.5 | 153.1 | 132.5 | 160.6 | 128.6 |
| ratio to before occlusion (%) | | 81.4 | 131.8 | 160.4 | 190.0 | 78.1 | 30.6 |

*Numerics in nervous condition estimation test is calculated by grading system of Bederson et al.
**Numerics in rotor rod test is reading value of count from rotor rod machine.
Abbreviations:
min: minute(s),
hrs: hours,
Ave: average, and
SD: standard deviation Test Example 12

Solvility Test

TM-2002 was added in purified water to be 10 mg per 1 ml and added hydrochloride to adjust to pH 2.0 and solved. Then, this solution was adjusted to pH 7.0, 8.0 and 2,0 (unadjust) by 1N sodium hydrate to prepare 3 solutions. These solutions were put on warming, dark cold place and after 24 hours, conditions of the solutions were observed. The pH 2.0 solusodium acid sulfite (1 mg) solution was prepared respectively; to these solutions, there was added 63 mg of TM-2002 hydrochloride, stirred and solved; the solutions allowed to warm to room temperature to observe the solving state. As the result, crystal precipitates were deposited according time in the solutions added 0.5 mg and 1 mg of sodium acid sulfite and after 24 hours, remarkable precipitates were observed. On the contrary, pH was 2 to 2.5 in the solution solved in only purified water, after 24 hours, no change was observed in its solving state and significant suppress of TM-2002 degradation was observed. Accordingly, the stability of TM-2002 itself will increase by using hydrochloride.

Instead of sodium acid sulfite, sodium sulfite ($Na_2SO_3$), sodium pyrosulfite ($Na_2S_2O_5$) were used and carried out experiment in the same manner as above, crystal precipitate was deposited in all of the solutions added these stabilizing agent.

The solving state of TM-2002 hydrochloride solution added L-cystein hydrochloride was examined in following manner; 1 mg and 2 mg of L-cystein hydrochloride were dissolved in 1 ml of purified water respectively; pH was adjusted to 6.5; to these solutions, there was added 63 mg of TM-2002 hydrochloride, stirred and solved; the solutions allowed to warm to room temperature to observe the solving state. As the result, no precipitates and deposits was observed in each solutions, and after 24 hours, no change was observed in solving state. In addition, the degradability was observed by thin layer chromatography (TLC/Silica-gel 60F254 (Merck Japan)/developing solvent: chloroform:methanol=9:1/detection:UV=254 nm). The compound was degraded very slowly in left over 24 hours at room temperature, however, it was significantly stabilized by addition of L-cystein. Under preservation at −20° C., this solution was stable after one week. Accordingly, the present invention provides lyophilized formulation comprising L-cystein by treating TM-2002 hydrochloride solution at low temperature and lyophilizing.

Preparation of TM-2002 Injectable Lyophilized Formulation

L-cystein hydrochloride (160 mg) was added to 80 ml of purified water, stirred and solved. The solution was adjust at pH 6.7 with 1N NaOH aqueous solution. Then 1 g of TM-2002 hydrochloride was added, stirred and solved, and the solution diluted with purified water to 100 ml with measuring flask. Such solution was divided into vial container of 50 ml by 6.3 ml each, frozen immediately with dry ice, and then stored at −80° C. to freeze completely. This was subjected to lyophilized for 3 days using lyophilizer. After lyophilizing, covered by rubber cap and sealed by aluminum cap using fastener, TM-2002 injectable lyophilized formulation was prepared.

The Solubility and Stability of TM-2002 Injectable Lyophilized Formulation

To TM-2002 injectable lyophilized formulation prepared above, there was added 20 ml of purified water per 1 vial. The lyophilized material solved immediately and be pale yellow, clear solution. 1.5 ml of saline was added to this solution (1 ml), and while keeping at room temperature, the solubility and stability was observed at 3 hours, 6 hours and 10 hours after solving. TLC (Kiezel gel 60F254/developing solvent: $CHCl_3$:MeOH=9:1/detection:UV=254 nm) was carried out to examine the change of ingredient. As the result, there was no precipitate, crystals or insoluble materials at 10 hours from dissolution and noticeable change of color was not observed. For the stability of ingredients, while decomposition products were observed in the control solution of TM-2002 hydrochloride at 10 hours, no decomposition product was observed in the present injectable formulation. The result of TLC is represented in FIG. 16. When the solution was further diluted with saline, the stability was as same. In addition, for said injectable lyophilized formulation which was left at room temperature for 30 days, the solubility and stability were observed in the same manner and there was no difference from that soon after preparing. The formulation is suitable for injectable lyophilized formulation which is prepared before use, and stable and usable.

Test Example 14

Examination of in Vivo Endoplasmic Reticula Stress (ER Stress) Alleviation Effect by TM-2002

Endoplasmic reticula stress alleviation effect by TM-2002 was examined using SHR/NDmcr-cp (Disease Model Cooperative Research Association) rats, which have been known their high blood pressure, hyperglycemia, hyperlipemia, obesity and hyperinsulinemia and renal function disorder while aging, and immunostained utilizing anti-ORP150 antibody. The stained section samples which were used for staining were prepared as following manner; SHR/NDmcr-cp rats which were administered the desired amount of test compound TM-2002 (dose: 100 mg/1 kg body weight) by diet (30 g daily), the rats which were administered no drug and SHR (hypertension) rats and Wistar Kyoto rats (control); kidney tissues of each rat were obtained after the end of drug administration period (33 weeks aged); all of tissues were fixed by Carnoy and embedded in paraffin. The staining of each samples was carried out by Catalyzed Sifnal Amplification (CSA) System (DAKO) according to their protocol. Briefly, deparaffinization was carried out by Histo-Clear (pational diagnostics) for 5 minutes 3 times, by 100% ethanol for 3 minutes 3 times and fitted in distilled water for 5 minutes; the samples were put into 10 mM sodium citrate aqueous solution (pH. 6.0) and heated with microwave for 5 minutes with boiling to activate the antibody; the samples were cooled to room temperature, and washed by TBS-T (0.05M Tris-HCl pH 7.6, 0.3M NaCl, 0.1% Tween 20) for 4 minutes 3 times; the samples were rinsed in 3% hydrogen peroxide solution (DACO) for 3 minutes to block endogenous peroxydase; the samples were treated with PROTEIN BLOCK (DACO) to inhibit nonspecific reaction of the antibody, reacted for 15 minutes with anti-ORP150 antibody (primary antibody) which was diluted with 1.5% goat serum to 400 folds, washed by TBS-T for 4 minutes 3 times; reacted with biotin-labeled goat anti-leporine antibody (200 folds; secondary antibody) for 15 minutes and washed by TBS-T for 4 minutes 3 times: reacted with Streptavidin-Biotin Complex (DACO) for 15 minutes and washed by TBS-T for 4 minutes 3 times; reacted with Amplification Reagent (DACO) for 15 minutes and washed with TBS-T for 4 minutes 3 times; reacted with Streptavidin-peroxidase (DACO) for 15 minutes and washed by TBS-T for 4 minutes 3 times; DAB coloring was carried out by Substrate-Chromogen Solution, washed by distilled water, anhydration was carried out by 100% ethanol for 3 minutes 3 times and by Histo-Clear (pational diagnostics) for 5 minutes 3 times, and embedded to complete the sample. The samples were observed by microscopic visualization with optical microscope (Olympus) and analyzed the result. As the result, there was no ORP150 positive staining site in Wistar Kyoto rats (control) and SHR rats (hypertension model) and was positive staining site in SHR/NDmcr-cp rats (Type II diabetes hypertension model). The enhancing of ER stress was observed in SHR/NDmcr-cp rats. There was decrease of positive staining site and suppressing ER stress in SHR/NDmcr-cp rats administered TM-2002 (cf. FIG. 17).

Test Example 15

Examination of Drug Efficiency on the Variation in Expression of ER Stress Inducing Molecules of TM-2002

Rat pancreatic β cell line (RIN-5F) was seeded in 6 well culture plate to $1.0 \times 10^5$ cells/well, and after 24 hours, TM-2002 in DMSO (200 mM, 50 mM) were added to be final concentration 200 μM, 50 μM. After another 1 hour, 0.2 μl of tunicamycin (Sigma) in methanol(1 mg/ml) was added. After culturing 8 hours, the cells were washed 2 ml of PBS(+) twice, and the cells were dissolved in 100 μl of lysate (50 mM Tris-HCl (pH 7.5), 150 mM NaCl, 100 mM NaF, 100 mM sodium phosphate (pH 7.4), 2 mM $Na_3VO_4$, 0.1% protease inhibitor cocktail (Sigma), 1% Triton X-100). To remove the insoluble fraction of this lysate, centrifuged at 12,000×g for 10 minutes and obtained the supernatant to give cell extract. The extract was quantified its protein concentration using DC protein assay kit (Bio Rad), and each samples (1 μg) was electrophoresed by SDS-PAGE and transferred to PVDF membrane. The membrane was blocked with 5% skimmed milk/0.1% Tween20-TBS for 1 hour at room temperature, and reacted with anti-ORP150 antibody in 5% skimmed milk/0.1% Tween20-TBS (2000 folds: specific antibody), anti-GRP78 antibody (Santa Cruz) in 5% skimmed milk/0.1% Tween20-TBS (100 folds) and anti-actin antibody (Sigma) in 5% skimmed milk/0.1% Tween20-TBS (200 folds) for 2 hours. Washed with 0.1% Tween20-TBS for 10 minutes 3 times, and for the detection of ORP150 and actin, HRP-labeled anti-leporine antibody (BIO-Rad; secondary antibody) in 5% skimmed milk/0.1% Tween20-TBS (2000 folds), for the detection of GRP78 alkalisphosphatase-labeled anti-goat antibody in 5% skimmed milk/0.1% Tween20-TBS (5000 folds) was used respectively, and reacted at room temperature for 1 hour. After washing with 0.1% Tween20-TBS for 10 minutes 3 times, the detection was carried out using ECL western blotting detection reagent (Amersham Bioscience). The detected signal was analyzed by Lane analyzer (ATTO) and calculated the signal strength. As the result, in tunicamycin added samples, ORP150 and GRP78 expression were enhanced respectively 1.88 folds and 1.46 fords comparing to that of control sample, and this indicate that ER stress was caused. In the TM-2002 and tunicamycin co-added sample, hyperexpression of ORP150 and GRP78 was suppressed by tunicamycin, and it is indicated that ER stress caused by tunicamycin is reduced (cf. FIGS. 18 and 19).

BRIEF DESCRIPTION OF THE DRAWINGS

FIG. 17 is a chart showing the reduction of positive staining site of SHR/NDmcr-cp with TM-2002.

Figure 1:
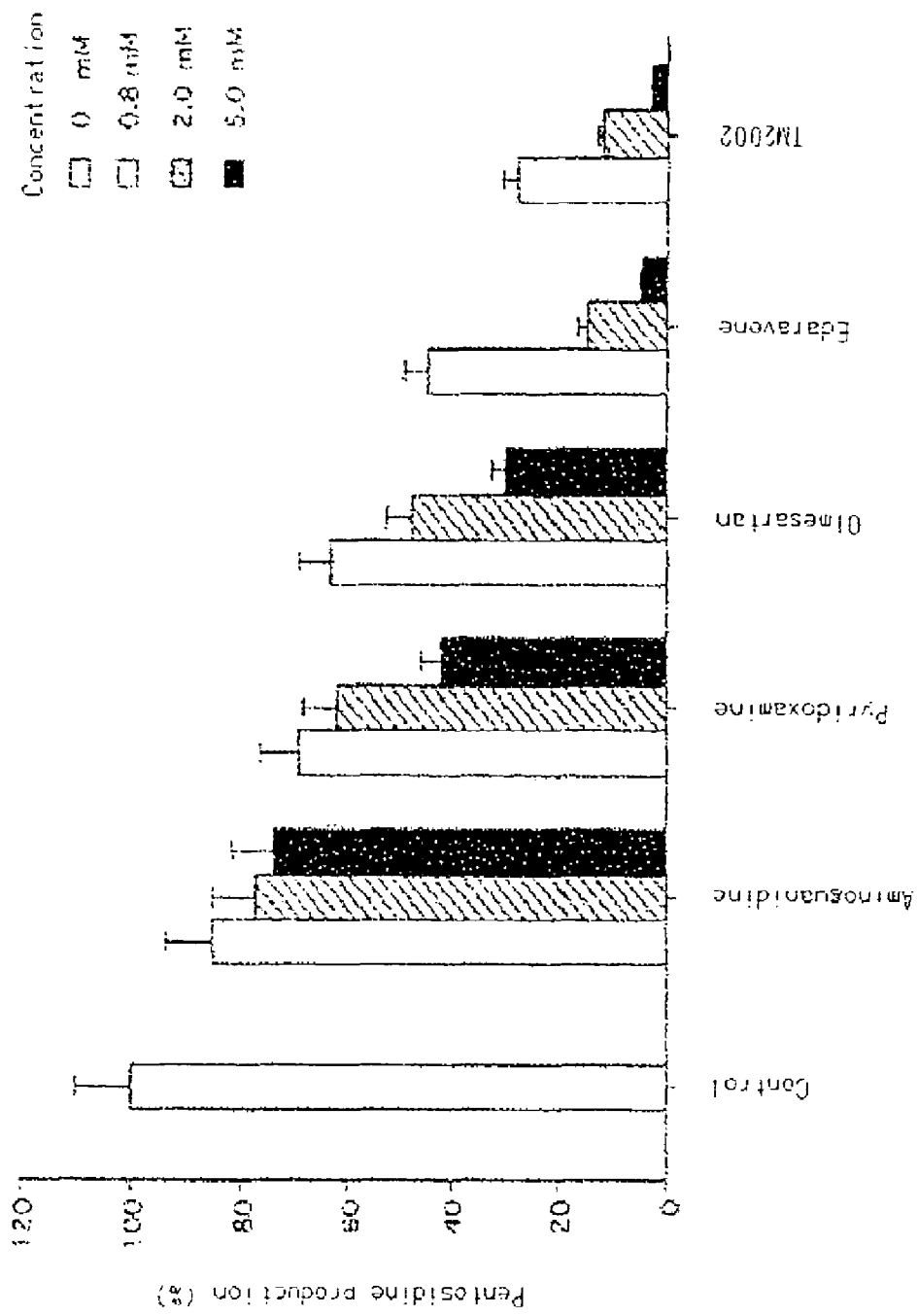
FIG. 1 is a chart showing the inhibiting effect of TM-2002 on pentosidine production.
Figure 2:
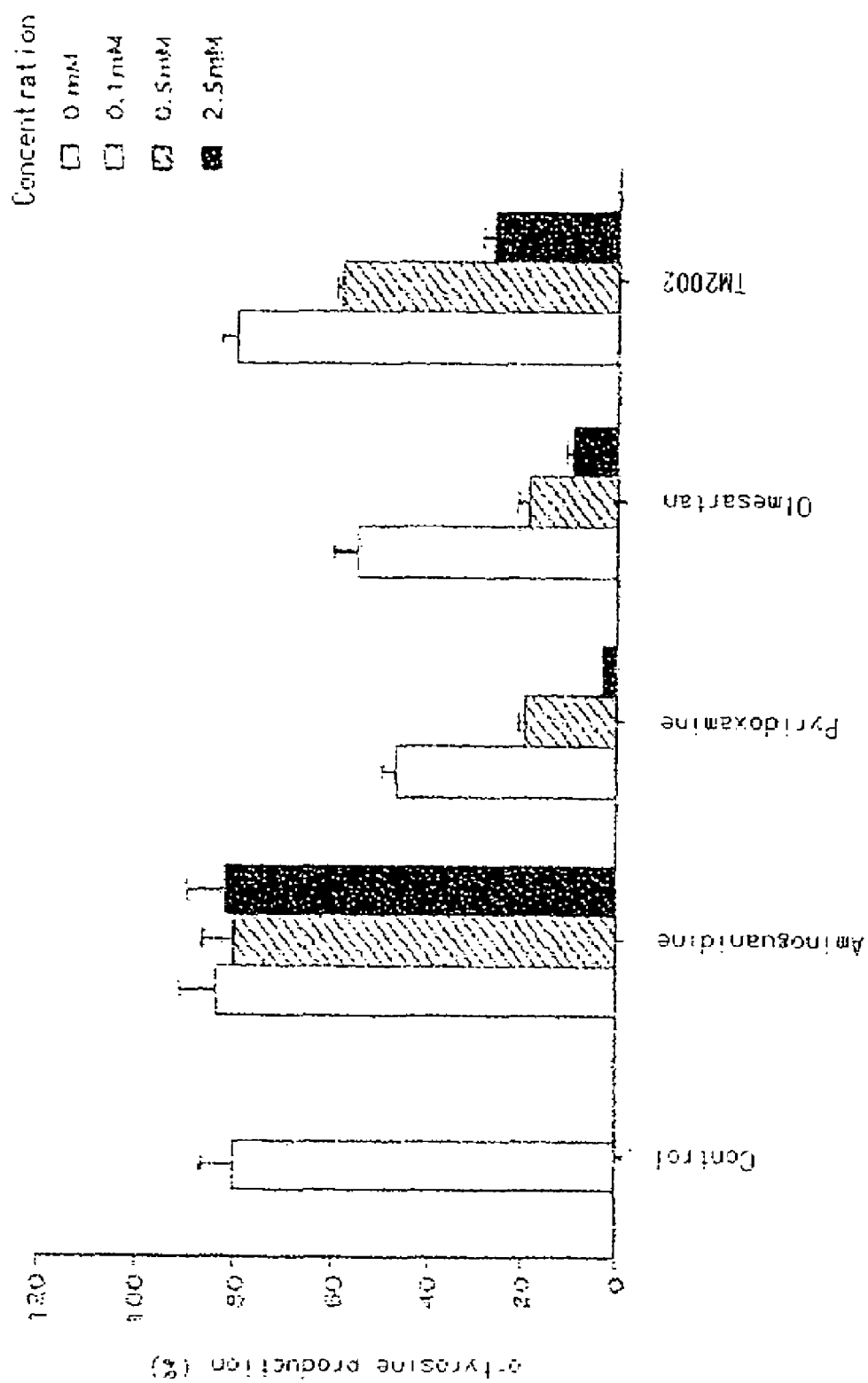
FIG. 2 is a chart showing the inhibiting effect of TM-2002 on hydroxylation of phenylalanine by hydroxy radical (o-tyrosine production inhibiting is used as an index).
Figure 3:
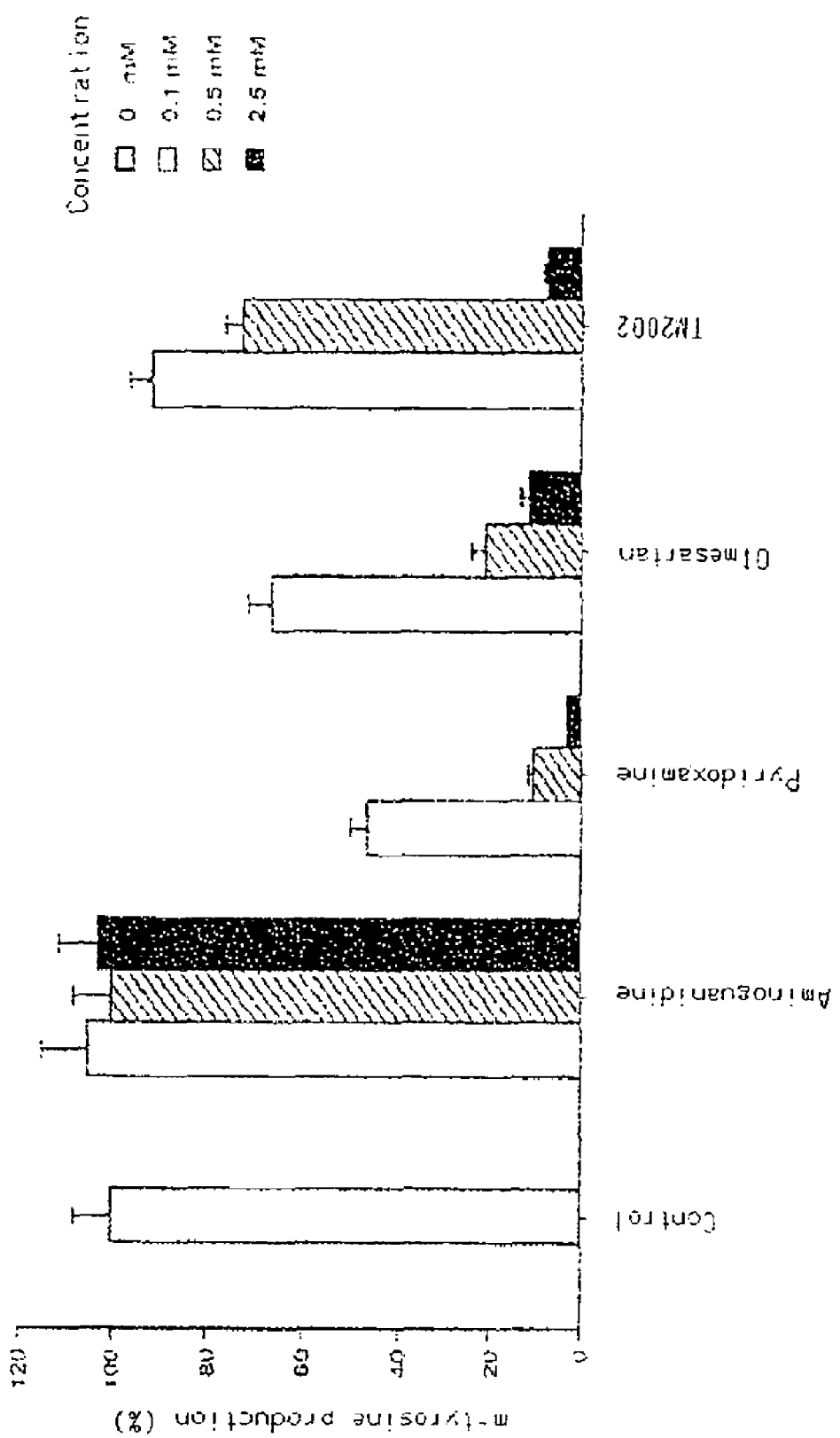
FIG. 3 is a chart showing the inhibiting effect of TM-2002 on hydroxylation of phenylalanine by hydroxy radical (m-tyrosine production inhibiting is used as an index).
Figure 4:
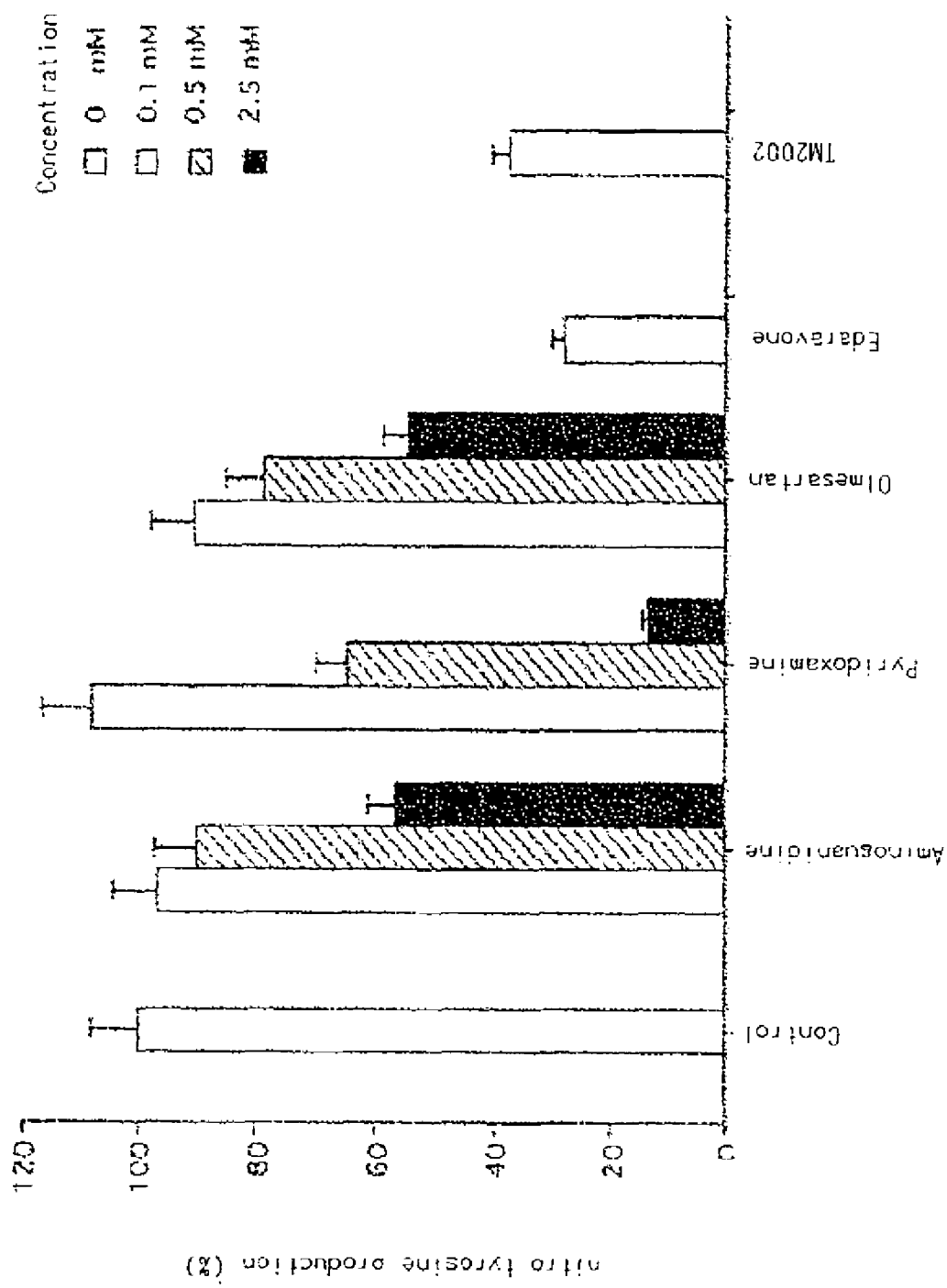
FIG. 4 is a chart showing the inhibiting effect of TM-2002 on nitration of tyrosine by peroxynitrite.
Figure 5:
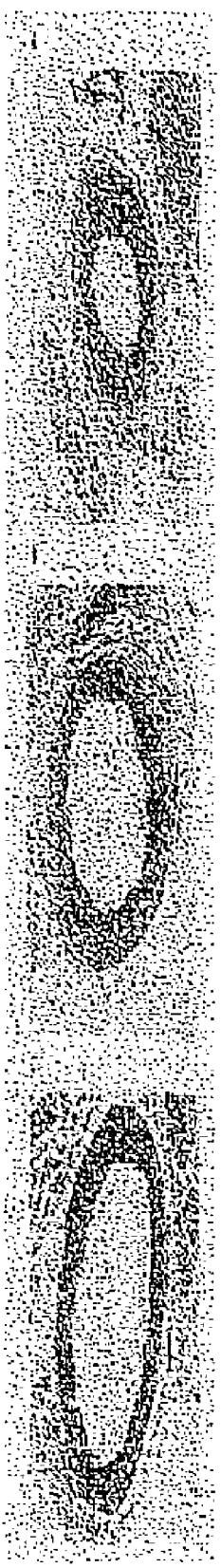
FIG. 5 is a photograph showing the vascular endothelial thickening inhibiting effect in rat carotid balloon injury model test (A is control; B is 50 mg/kg of TM-2002 administration; C is 45 mg/kg of aminoguanidine administration).
Figure 6:
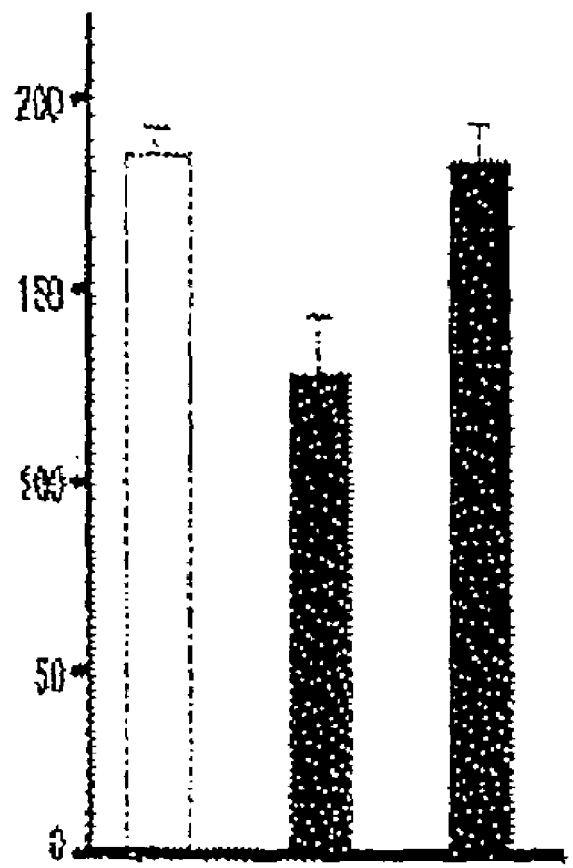
FIG. 6 is a chart showing the absence of blood pressure-lowering effect in TM-2002.
Figure 7:
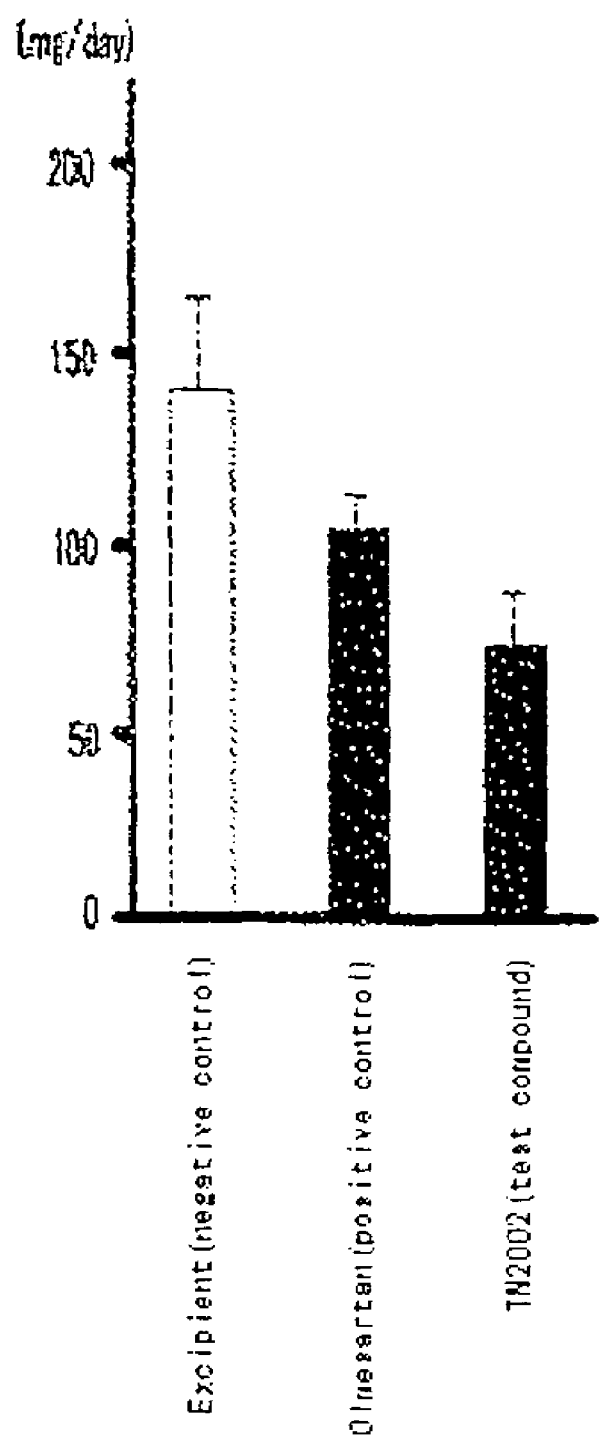
FIG. 7 is a chart showing the urinary protein inhibiting effect of TM-2002
Figure 8:
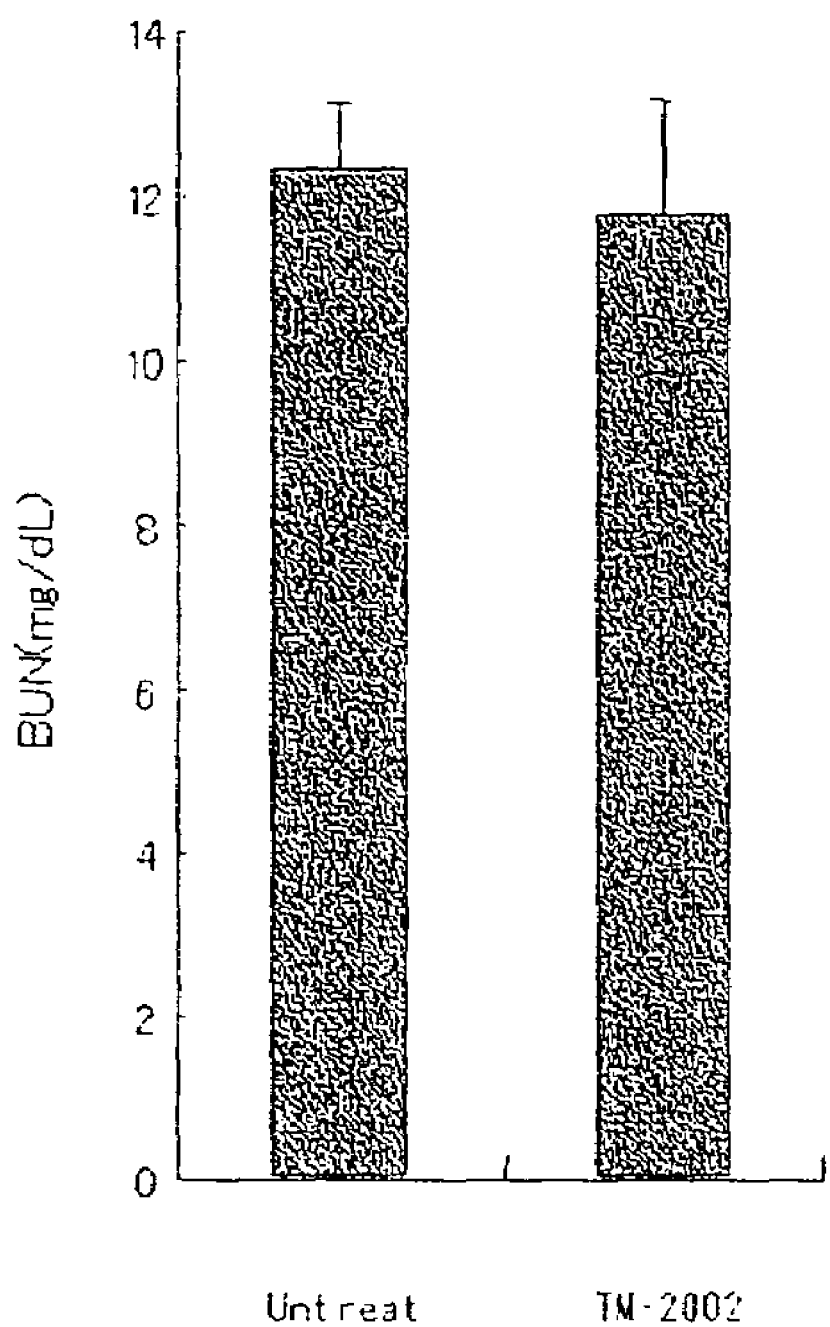
FIG. 8 is a chart showing the BUN reducing effect of TM-2002 in Thy-1 nephritis model.
Figure 9:
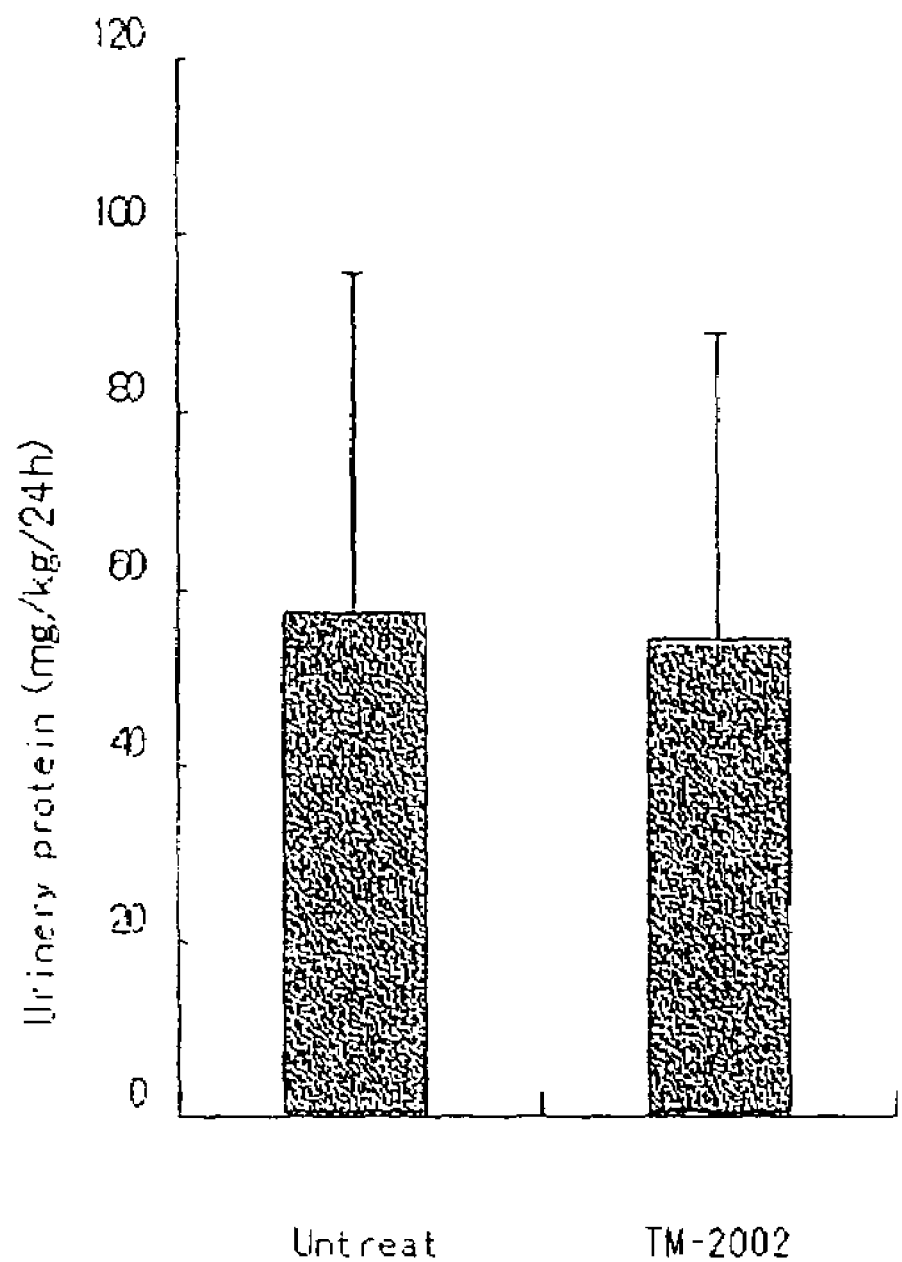
FIG. 9 is a chart showing the urinary protein reducing effect of TM-2002 in Thy-1 nephritis model.
Figure 10:
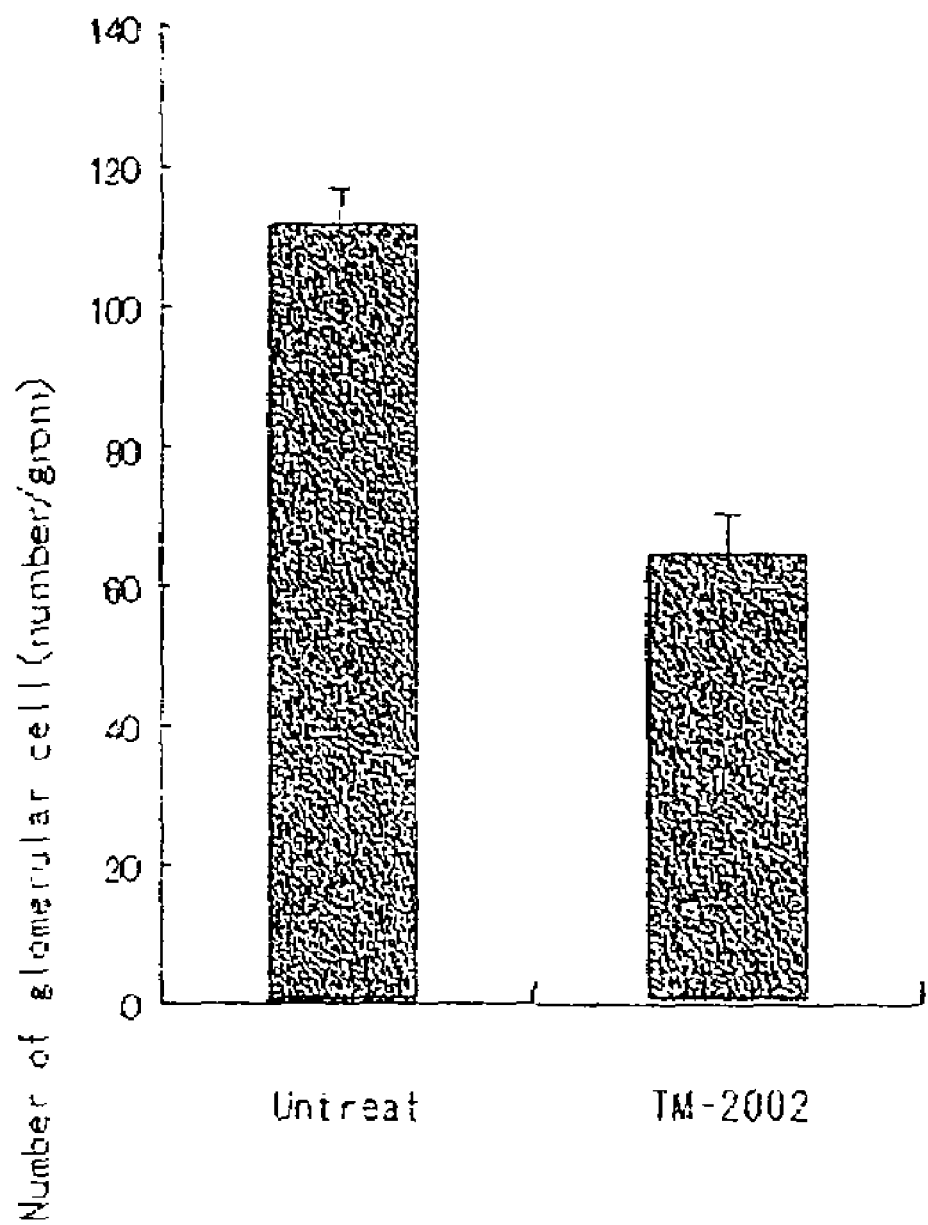
FIG. 10 is a chart showing the number of glomerular cells reducing effect of TM-2002 in Thy-1 nephritis model.
Figure 11:
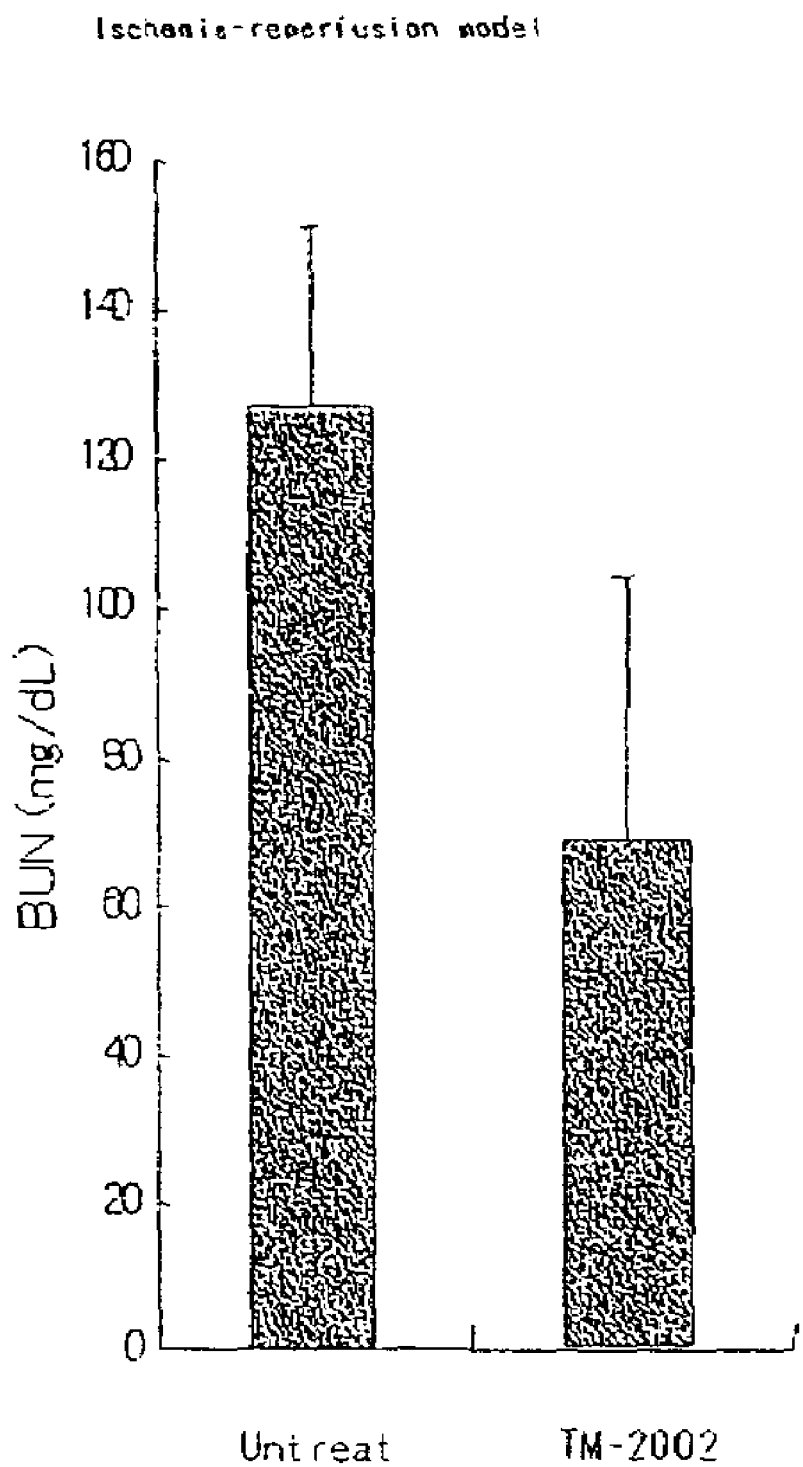
FIG. 11 is a chart showing the BUN reducing effect of TM-2002 in ischemia-reperfusion model.
Figure 12:
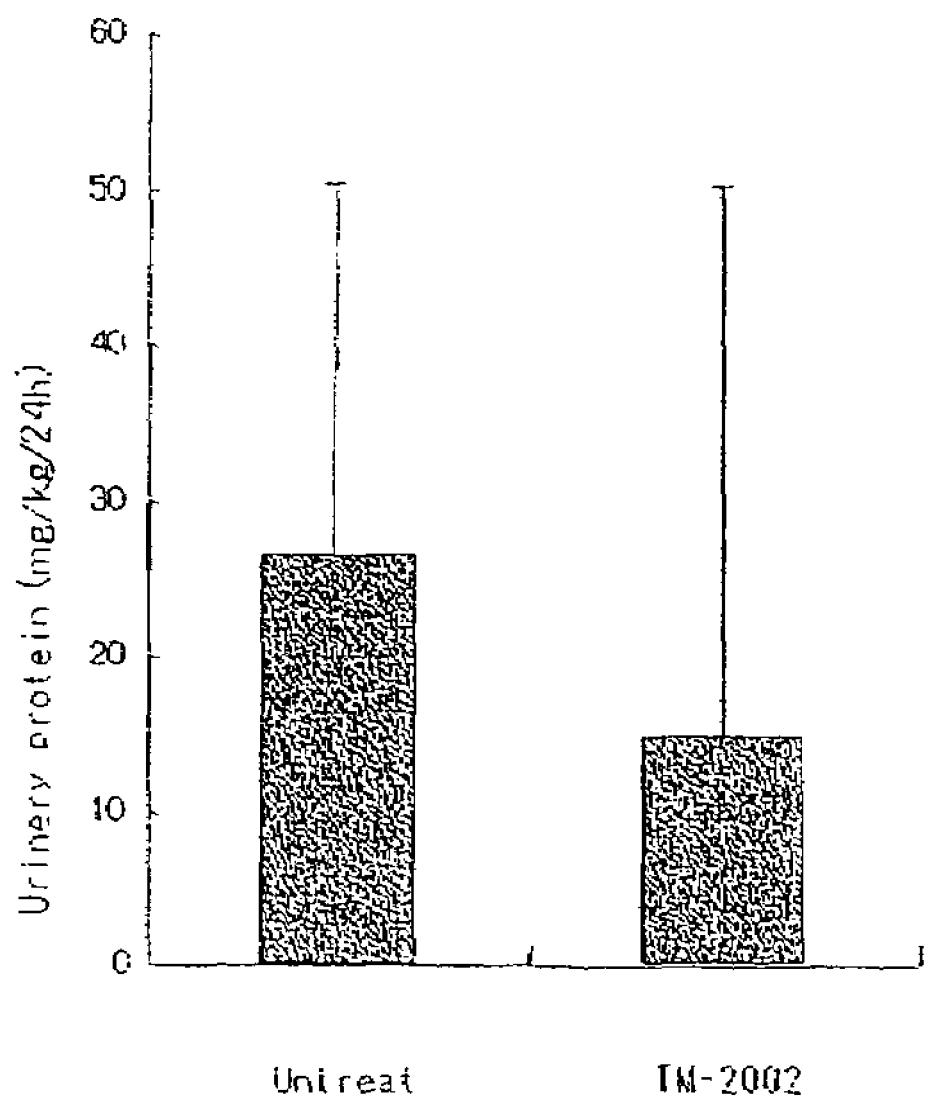
FIG. 12 is a chart showing the urinary protein reducing effect of TM-2002 in ischemia-reperfusion model.
Figure 13:
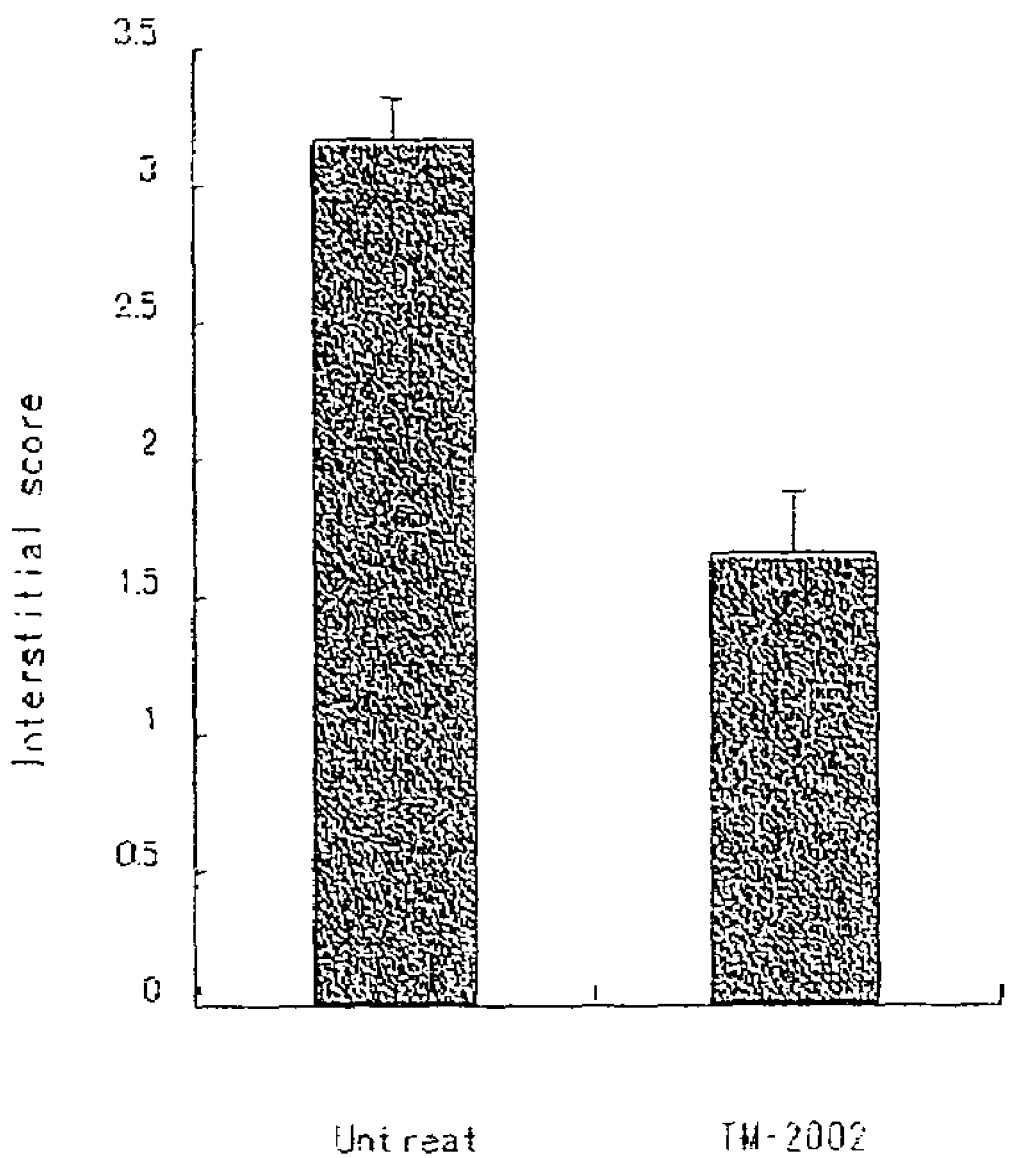
FIG. 13 is a chart showing the stromal disorder score of TM-2002 in ischemia-reperfusion model.
Figure 14:
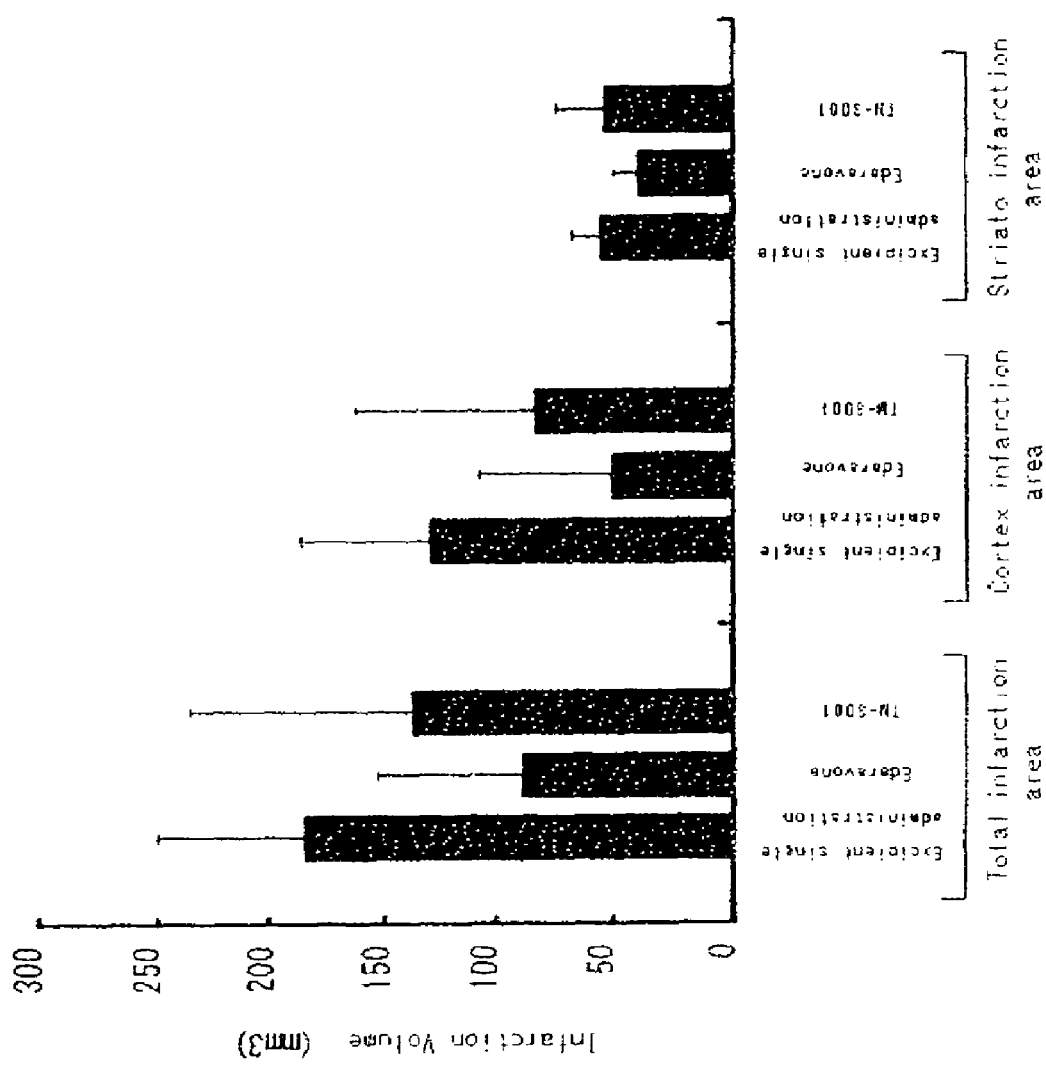
FIG. 14 is a chart showing the reduction of the cerebral infarction nest with TM-2002.
Figure 15:
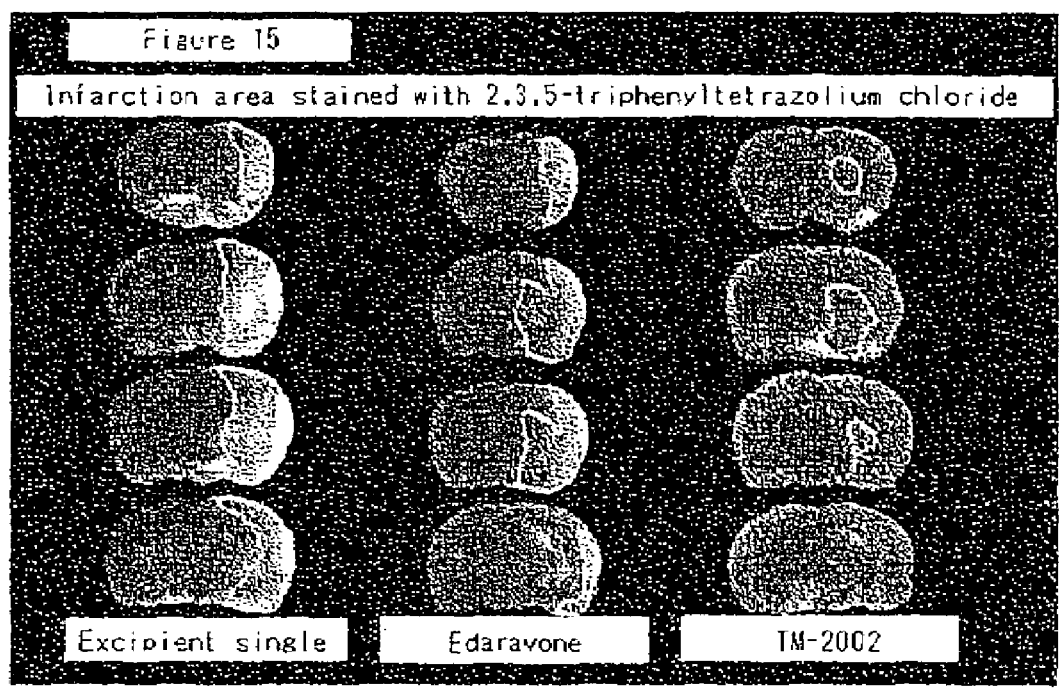
FIG. 15 is a chart showing the reduction of the cerebral infarction nest with TM-2002.
Figure 16:
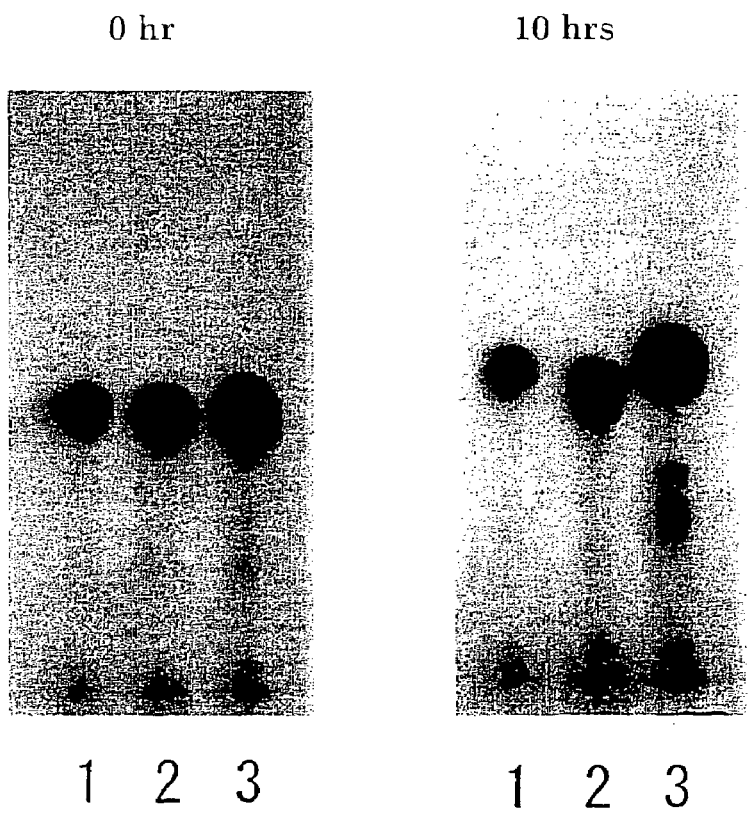
FIG. 16 is a chart showing the stability of the solution of TM-2002 injectable lyophilized formulation.
Figure 18:
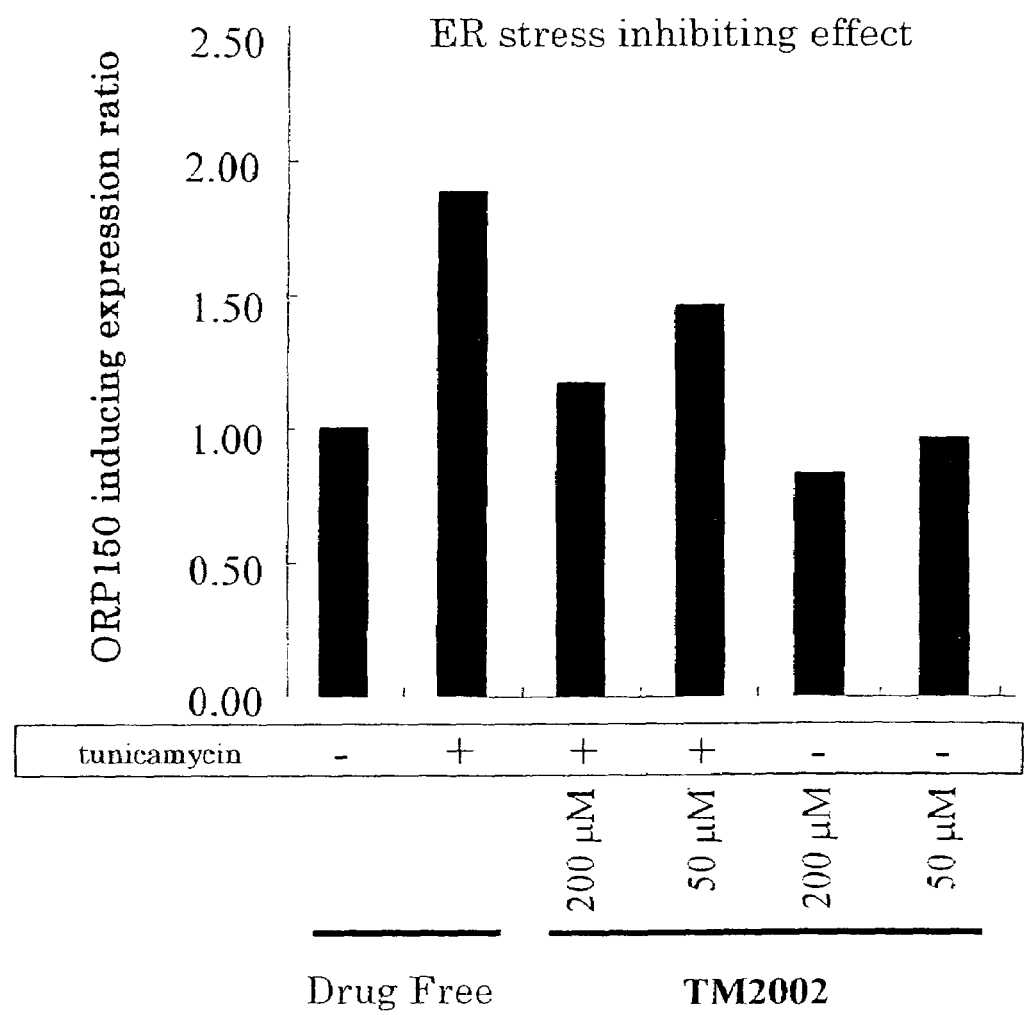
FIG. 18 is a chart showing the OPR150 hyperexpression inhibiting effect of TM-2002 with tunicamycin.
Figure 19:
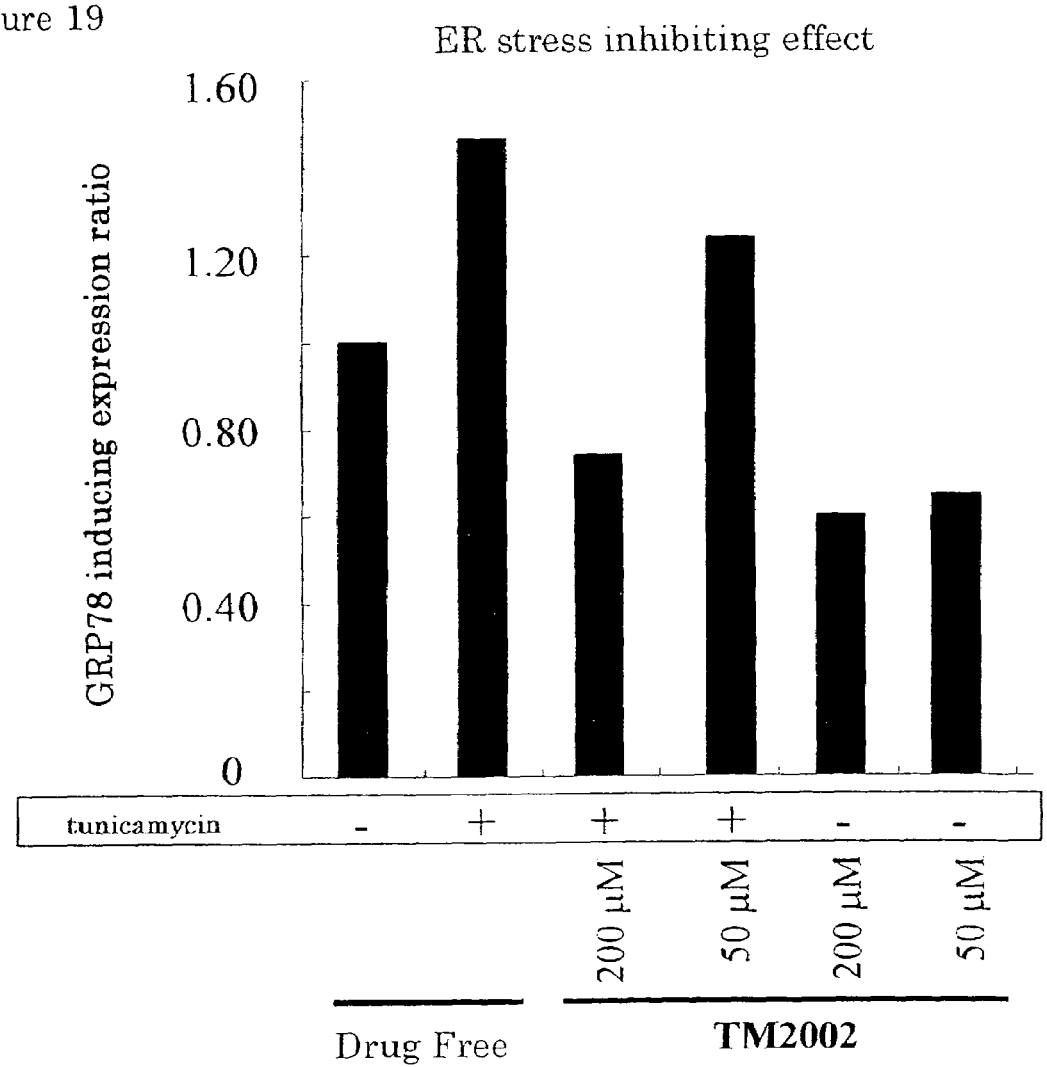
FIG. 19 is a chart showing the GRP78 hyperexpression inhibiting effect of TM-2002 with tunicamycin.

What is claimed is:

1. A compound of formula (II)

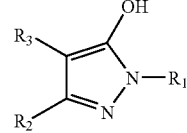

wherein R1 is a phenyl group, R2 is a methyl group, and R3 is a 6-methyl-1,3-dihydrofuro-[3,4-c]-pyridin-7-ol group, in free or salt form.

2. A compound of formula (I)

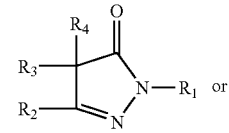

or

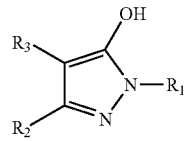

formula (II)

wherein R4 is a hydrogen atom and wherein R1 is a phenyl group, R2 is a methyl group, and R3 is a 6-methyl-1,3-dihydrofuro-[3,4-c]-pyridin-7-ol group, in free or salt form.

* * * * *